United States Patent
Li et al.

(10) Patent No.: US 9,248,173 B2
(45) Date of Patent: Feb. 2, 2016

(54) WT1 ANTIGEN PEPTIDE CONJUGATE VACCINE

(71) Applicants: SUMITOMO DAINIPPON PHARMA CO., LTD., Osaka-shi (JP); INTERNATIONAL INSTITUTE OF CANCER IMMUNOLOGY, INC., Suita-shi (JP)

(72) Inventors: Chiang Jia Li, Cambridge, MA (US); Hitoshi Ban, Osaka (JP); Yukihiro Nishio, Osaka (JP); Masashi Goto, Osaka (JP); Toshio Nishihara, Osaka (JP); Yosuke Takanashi, Osaka (JP)

(73) Assignees: SUMITOMO DAINIPPON PHARMA CO., LTD., Osaka-shi (JP); INTERNATIONAL INSTITUTE OF CANCER IMMUNOLOGY, INC., Suita-shi (JP)

( * ) Notice: Subject to any disclaimer, the term of this patent is extended or adjusted under 35 U.S.C. 154(b) by 0 days.

(21) Appl. No.: 14/706,772

(22) Filed: May 7, 2015

(65) Prior Publication Data

US 2015/0238587 A1    Aug. 27, 2015

Related U.S. Application Data

(60) Division of application No. 14/549,091, filed on Nov. 20, 2014, which is a continuation of application No. PCT/JP2014/059336, filed on Mar. 28, 2014.

(30) Foreign Application Priority Data

Mar. 29, 2013  (JP) .................................. 2013-072173
Jul. 31, 2013   (JP) .................................. 2013-158383

(51) Int. Cl.
*A61K 38/00*  (2006.01)
*A61K 38/16*  (2006.01)
*A61K 39/00*  (2006.01)
(Continued)

(52) U.S. Cl.
CPC ............. *A61K 39/0011* (2013.01); *A61K 39/00* (2013.01); *A61K 47/4833* (2013.01); *C07K 7/06* (2013.01); *C07K 7/08* (2013.01); *C07K 14/00* (2013.01); *C07K 14/4748* (2013.01); *A61K 2039/55* (2013.01); *A61K 2039/55566* (2013.01); *A61K 2039/572* (2013.01); *A61K 2039/64* (2013.01); *A61K 2039/70* (2013.01)

(58) Field of Classification Search
CPC ................................... C07K 7/06; C07K 7/08
See application file for complete search history.

(56) References Cited

U.S. PATENT DOCUMENTS

| | | | |
|---|---|---|---|
| 7,030,212 B1 | 4/2006 | Sugiyama et al. | |
| 7,326,767 B1 | 2/2008 | Stauss et al. | |

(Continued)

FOREIGN PATENT DOCUMENTS

| | | |
|---|---|---|
| CA | 2757764 | 10/2010 |
| JP | 2002-525099 | 8/2002 |

(Continued)

OTHER PUBLICATIONS

Interference No. 105987—Sugiyama Motion 1 (Mar. 26, 2014).
(Continued)

*Primary Examiner* — Marcela M Cordero Garcia
*Assistant Examiner* — Kaipeen Yang
(74) *Attorney, Agent, or Firm* — Oblon, McClelland, Maier & Neustadt, L.L.P.

(57) ABSTRACT

A compound represented by the formula (1):

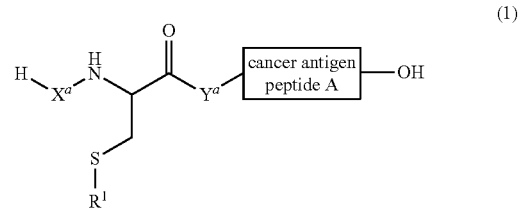

wherein $X^a$ and $Y^a$ are each a single bond and the like, cancer antigen peptide A is an MHC class I-restricted WT1 peptide consisting of 7-30 amino acid residues, $R^1$ is a hydrogen atom, a group represented by the formula (2):

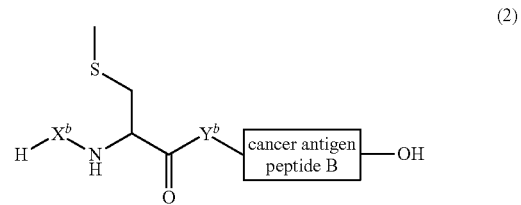

wherein $X^b$ and $Y^b$ are each a single bond and the like, cancer antigen peptide B has a sequence different from that of the cancer antigen peptide A, and is an MHC class I-restricted WT1 peptide consisting of 7-30 amino acid residues, or cancer antigen peptide C, and cancer antigen peptide C has a sequence different from that of the cancer antigen peptide A, and is an MHC class I-restricted WT1 peptide or an MHC class II-restricted WT1 peptide, consisting of 7-30 amino acid residues containing one cysteine residue, or a salt thereof, and the like.

28 Claims, 14 Drawing Sheets

(51) Int. Cl.
C07K 7/06 (2006.01)
C07K 7/08 (2006.01)
C07K 14/00 (2006.01)
C07K 14/47 (2006.01)
A61K 47/48 (2006.01)

(56) References Cited

U.S. PATENT DOCUMENTS

| 7,608,685 | B1 | 10/2009 | Sugiyama et al. |
| 2005/0266014 | A1 | 12/2005 | Sugiyama et al. |
| 2006/0093615 | A1 | 5/2006 | Sugiyama et al. |
| 2006/0217297 | A1 | 9/2006 | Sugiyama et al. |
| 2008/0070835 | A1 | 3/2008 | Sugiyama |
| 2008/0159993 | A1 | 7/2008 | Stauss et al. |
| 2009/0143291 | A1 | 6/2009 | Sugiyama et al. |
| 2009/0281043 | A1 | 11/2009 | Sugiyama et al. |
| 2010/0062010 | A1 | 3/2010 | Nishihara et al. |
| 2011/0098233 | A1 | 4/2011 | Sugiyama |
| 2012/0301492 | A1 | 11/2012 | Gaiger et al. |

FOREIGN PATENT DOCUMENTS

| WO | WO 00/06602 | 2/2000 |
| WO | WO 00/18795 | 4/2000 |
| WO | WO 2004/063217 | 7/2004 |
| WO | WO 2005/045027 | 5/2005 |
| WO | WO 2007/047764 | 4/2007 |
| WO | WO 2007/063903 | 6/2007 |
| WO | WO 2007/120673 | 10/2007 |
| WO | WO 2008/081701 | 7/2008 |

OTHER PUBLICATIONS

Interference No. 105987—Stauss Motion 1 (May 15, 2014).
Interference No. 105987—Stauss Motion 2 (May 15, 2014).
Interference No. 105987—Stauss Motion 3 (May 15, 2014).
Interference No. 105987—Sugiyama Substantive Motion 1 (May 15, 2014).
Interference No. 105987—Sugiyama Responsive Motion 2 (Jun. 5, 2014).
Interference No. 105987—Stauss Opposition 1 (Jul. 17, 2014).
Interference No. 105987—Stauss Opposition 2 (Jul. 17, 2014).
Interference No. 105987—Sugiyama Opposition to Stauss Motion 1 (Jul. 17, 2014).
Interference No. 105987—Sugiyama Oppiosition to Stauss Motion 2 (Jul. 17, 2014).
Interference No. 105987—Sugiyama Opposition to Stauss Motion 3 (Jul. 17, 2014).
Interference No. 105987—Sugiyama Reply 1 (Aug. 28, 2014).
Interference No. 105987—Sugiyama Reply 2 (Aug. 28, 2014).
Interference No. 105987—Stauss Reply 1 (Aug. 28, 2014).
Interference No. 105987—Stauss Reply 2 (Aug. 28, 2014).
Interference No. 105987—Stauss Reply 3 (Aug. 28, 2014).
Interference No. 105987—Decision on Motions BD.R. 125(a) (Feb. 20, 2015).
Interference No. 105987—Exhibit 1001—Amendment for entry in Sugiyama U.S. Appl. No. 12/181,938.
Interference No. 105987—Exhibit 1002—U.S. Pat. No. 7,030,212 B1, Apr. 18, 2006.
Interference No. 105987—Exhibit 1003—Terminal Disclaimer filed and approved in Sugiyama U.S. Appl. No. 12/181,938, filed Dec. 4, 2013.
Interference No. 105987—Exhibit 1004—The original specification of Sugiyama U.S. Appl. No. 12/181,938, filed Jul. 29, 2008.
Interference No. 105987—Exhibit 1005—The original specification of U.S. Appl. No. 11/196,452, filed Aug. 4, 2005, issued as U.S. Pat. No. 7,608,685.
Interference No. 105987—Exhibit 1006—The original specification of U.S. Appl. No. 09/744,815, filed Jan. 30, 2001, issued as U.S. Pat. No. 7,030,212.
Interference No. 105987—Exhibit 1007—WO 00/06602 which is a publication of International Application PCT/JP99/04130, filed Jul. 30, 1999.
Interference No. 105987—Exhibit 1008—The original and the certified translation of Japanese Application JP 10-218093, filed Jul. 31, 1998.
Interference No. 105987—Exhibit 1009—The USPTO Communication mailed Jan. 9, 2014, in Sugiyama U.S. Appl. No. 12/181,938.
Interference No. 105987—Exhibit 1010—U.S. Pat. No. 7,326,767 B2, B1, Feb. 5, 2008.
Interference No. 105987—Exhibit 1011—U.S. Pat. No. 8,529,904 B2, Sep. 10, 2013.
Interference No. 105987—Exhibit 1012—Certified Copy of UK 9823897.5, filed Nov. 2, 1998, which was filed in the USPTO Apr. 12, 2002.
Interference No. 105987—Exhibit 1013—Sugiyama U.S. Appl. No. 12/181,938, published as U.S. 2009/0143291 A1.
Interference No. 105987—Exhibit 1014—PCT/GB99/03572, filed on Nov. 2, 1999, published as WO 00/26249 on May 11, 2000.
Interference No. 105987—Exhibit 1015—Non-Final Office Action mailed May 5, 2003, in Stauss U.S. Appl. No. 09/625,963.
Interference No. 105987—Exhibit 1016—Non-Final Office Action mailed Jan. 30, 2004, in Stauss U.S. Appl. No. 09/625,963.
Interference No. 105987—Exhibit 1017—Stauss Response filed Apr. 26, 2013, in Stauss U.S. Appl. No. 11/825,578.
Interference No. 105987—Exhibit 1018—Stauss Response filed Nov. 5, 2003, in Stauss U.S. Appl. No. 09/625,963.
Interference No. 105987—Exhibit 1019—Oka et al., J. Immunol. 164(4): 1873-1880, 2000.
Interference No. 105987—Exhibit 1020—Stauss Response filed Jul. 30, 2004, in Stauss U.S. Appl. No. 09/625,963.
Interference No. 105987—Exhibit 1021—Gaiger et al., Blood 96(4): 1480-1489, 2000.
Interference No. 105987—Exhibit 1022—Mailander et al., Leukemia 18: 165-166, 2004.
Interference No. 105987—Exhibit 1023—Non-Final Office Action mailed Apr. 29, 2010, in Stauss U.S. Appl. No. 11/825,578.
Interference No. 105987—Exhibit 1024—Final Office Action mailed Oct. 26, 2010, in Stauss U.S. Appl. No. 11/825,578.
Interference No. 105987—Exhibit 1025—Janeway et al., Immunobiology, 1997 4th Edition Garland Press 1999 pp. 121, 551 and 569 and Figures 4.3, 4.5 and 4.7.
Interference No. 105987—Exhibit 1026—Srivastava, P., Nature Immunology 1(5): 363-366, 2000.
Interference No. 105987—Exhibit 1027—Gaiger et al., Clin. Cancer Res. 7: 761s-765s, 2001.
Interference No. 105987—Exhibit 1028—Guidance for Industry—Preclinical Assessment of Investigational Cellular and Gene Therapy Products, U.S. Department of Health and Human Services Food and Drug Administration Center for Biologics Evaluation and Research, Nov. 2013.
Interference No. 105987—Exhibit 1029—U.S. Pat. No. 7,063,854.
Interference No. 105987—Exhibit 1031—Amendment for entry in Sugiyama U.S. Appl. No. 12/181,938.
Interference No. 105987—Exhibit 1032—Terminal Disclaimer over U.S. Pat. No. 7,030,212 filed on Feb. 4, 2010 in U.S. Appl. No. 12/366,200.
Interference No. 105987—Exhibit 1033—USPTO notice of Mar. 10, 2010, showing the approval of the Terminal Disclaimer filed on Feb. 4, 2010.
Interference No. 105987—Exhibit 1034—Amendment filed Sep. 17, 2004, in U.S. Appl. No. 09/744,815.
Interference No. 105987—Exhibit 1035—Preliminary Amendment filed Jul. 2, 2009, in Sugiyama U.S. Appl. No. 12/181,938.
Interference No. 105987—Exhibit 1036—U.S. Patent Application Publication US 2008/0159993, published Jul. 3, 2008.
Interference No. 105987—Exhibit 1038—Response to Formalities Letter and Preliminary Amendment filed Mar. 31, 2014 in Stauss U.S. Appl. No. 13/966,454.
Interference No. 105987—Exhibit 1039—Chart comparing Sugiyama current claims with pre-critical date claims in Sugiyama U.S. Appl. No. 12/181,938 and U.S. Appl. No. 09/744,815.

(56) References Cited

OTHER PUBLICATIONS

Interference No. 105987—Exhibit 1040—the Preliminary Amendment filed on Jul. 29, 2008, in Sugiyama U.S. Appl. No. 12/181,938.
Interference No. 105987—Exhibit 1041—Preliminary Amendment filed on Feb. 2, 2009, in Sugiyama U.S. Appl. No. 12/181,938.
Interference No. 105987—Exhibit 1042—Preliminary Amendment filed on Aug. 4, 2005, in U.S. Appl. No. 11/196,452.
Interference No. 105987—Exhibit 1043—Amendment filed on Mar. 20, 2008, in U.S. Appl. No. 11/196,452.
Interference No. 105987—Exhibit 1044—Preliminary Amendment filed on Jan. 30, 2001, in U.S. Appl. No. 09/744,815.
Interference No. 105987—Exhibit 1045—Amendment filed on Aug. 1, 2005, in U.S. Appl. No. 09/744,815.
Interference No. 105987—Exhibit 1046—Amendment filed on Jun. 29, 2011, in Sugiyama U.S. Appl. No. 12/181,938.
Interference No. 105987—Exhibit 1047—Office Action mailed Dec. 29, 2010, in Sugiyama U.S. Appl. No. 12/181,938.
Interference No. 105987—Exhibit 1048—Amendment filed on Dec. 4, 2013, in Sugiyama U.S. Appl. No. 12/181,938.
Interference No. 105987—Exhibit 1049—Amendment filed on Nov. 9, 2012, in Sugiyama U.S. Appl. No. 12/181,938.
Interference No. 105987—Exhibit 1050—Deposition Transcript of Dr. Özlem Türeci taken Jun. 30, 2014.
Interference No. 105987—Exhibit 1051—Keilholz, Leukemia, (2004) 18, 165-166.
Interference No. 105987—Exhibit 1052—Oka et al, Proc. Natl. Acad. Sci., (2004) 101, 13885-13890.
Interference No. 105987—Exhibit 1053—Amendment filed Mar. 14, 2006, in Stauss U.S. Appl. No. 09/625,963.
Interference No. 105987—Exhibit 1054—Appeal Brief filed Nov. 22, 2006, in Stauss U.S. Appl. No. 09/625,963.
Interference No. 105987—Exhibit 1055—Amendment filed Aug. 27, 2010, in Stauss U.S. Appl. No. 11/825,578.
Interference No. 105987—Exhibit 1057—Declaration for Utility or Design Patent Application filed on Jul. 6, 2007 during examination of the '904 patent.
Interference No. 105987—Exhibit 1058—Sugiyama's Objections to Stauss's Exhibits.
Interference No. 105987—Exhibit 2001—U.S. Pat. No. 7,326,767 (Stauss '767).
Interference No. 105987—Exhibit 2002—Sugiyama Preliminary Amendment dated Jul. 29, 2008 to U.S. Appl. No. 12/181,938, cancelling claims 1-7, adding new claims 8-19.
Interference No. 105987—Exhibit 2003—Sugiyama Preliminary Amendment dated Feb. 2, 2009 to U.S. Appl. No. 12/181,938, cancelling claims 1-19, adding new claims 20-23.
Interference No. 105987—Exhibit 2004—Sugiyama Preliminary Amendment dated Jul. 2, 2009 to U.S. Appl. No. 12/181,938, amending claims 21, 22, adding new claims 24-67.
Interference No. 105987—Exhibit 2005—Office Action dated Dec. 29, 2010 rejecting Sugiyama claims 20-24, and 27-28 as unpatentable under 35 USC § 112 and for nonstatutory double patenting over claims 1-5 of U.S. Pat. No. 7,030,212 and claims 1-5 of U.S. Pat. No. 7,608,685.
Interference No. 105987—Exhibit 2006—U.S. Pat. No. 7,608,685 (Sugiyama '685).
Interference No. 105987—Exhibit 2007—Sugiyama Amendment dated Jun. 29, 2011 amending the numeric range and size 14 limitations of the amino acids in claims 20, and 21.
Interference No. 105987—Exhibit 2008—Final Office Action dated Oct. 7, 2011 rejecting Sugiyama claim 28 as unpatentable under 35 USC §112 and claims 20-24, and 27-28 as unpatentable for nonstatutory double patenting over claims 1-5 of U.S. Pat. No. 7,030,212 and claims 1-5 of U.S. Pat. No. 7,608,685.
Interference No. 105987—Exhibit 2009—Sugiyama Amendment dated Nov. 9, 2012 adding involved new claims 68-75.
Interference No. 105987—Exhibit 2010—Office Action dated Jul. 24, 2013 rejecting Sugiyama claims 20-24, 27-28, 72-73 as being unpatentable for nonstatutory obviousness-type double patenting over claims 1-5 of U.S. Pat. No. 7,030,212 and claims 1-5 of U.S. Pat. No. 7,608,685.
Interference No. 105987—Exhibit 2011—Sugiyama Amendment dated Dec. 4, 2013 amending limitations of claims 27-28.
Interference No. 105987—Exhibit 2012—Application Data Sheet from file history of the '938 application filed on Jul. 29, 2008.
Interference No. 105987—Exhibit 2013—Declaration of Dr. Özlem Türeci.
Interference No. 105987—Exhibit 2014—Chart of Sugiyama's Pre- and Post-critical Date Claims.
Interference No. 105987—Exhibit 2015—Kakugawa et al "Efficient Induction of Peptide-specific Cytotoxic T Lymphocytes by LPS-Activated Spleen Cells", Microbiol. Immunnol., vol. 44(2), pp. 123-133, (2000).
Interference No. 105987—Exhibit 2016—The Decision dated Jan. 17, 2014 of the Board of Patent Appeals of the European Patent Office rendered in Case No. T1457/09-3.3.04, entitled "Immunotherapeutic methods using epitopes of WT-1 and GATA-1", Patent Proprietor: Ganymed Pharmaceuticals AG and Opponent Dainippon Sumitomo Pharma Co., Ltd., issued Mar. 6, 2014.
Interference No. 105987—Exhibit 2017—Transcript of Deposition of Dr. Türeci taken on Jun. 30, 2014.
Interference No. 105987—Exhibit 2018—Supplemental Application Data Sheet filed Mar. 31, 2014 in Response to Formalities Letter and Preliminary Amendment to U.S. Appl. No. 13/966,454 (the '454 application).
Interference No. 105987—Exhibit 2019—Office Action dated Sep. 14, 2012 from the file history of involved Stauss U.S. Pat. No. 8,529,904.
Interference No. 105987—Exhibit 2020—the Notice of Allowability dated May 6, 2013 from the file history of involved Stauss U.S. Pat. No. 8,529,904.
Interference No. 105987—Exhibit 2022—Title page and pp. 551 to 554 of Janeway et al., Immunobiology, 1997 4th Edition Garland Press 1999.
Gaiger et al., Blood 96(4), 1480-1489, 2000.
Mailander et al., Leukemia 18, 165-166, 2004.
Janeway et al., Immunobiology 1997 $4^{th}$ Edition Garland Press 1999, pp. 121, 551 and 569 and Figures 4.3, 4.5 and 4.7.
Srivastava, Nature Immun. 1(5), 363-366, 2000.
Gaiger et al., Clin. Cancer Clin. Cancer Res. 7, 761s-765s, 2001.
Guidance for Industry—Preclinical Assessment of Investigational Cellular and Gene Therapy Products, U.S. Department of Health and Human Services Food and Drug Administration Cancer for Biologics Evaluation and research, Nov. 2013, 35 pages.
Keilholz, Leukemia (2004) 18, 165-166.
Oka et al., National Acad. Sci (2004), 101,13885-13890.
Kakugawa et al., Efficient Induction of Peptide-specific Cytotoxic T Lymphocytes by LPS-Activated Spleen Cells, Microbiol. Immunol., vol. 44(2), pp. 123-133, 2000.
Title page and pp. 551-554 of Janeway et al., Immunobiology, 1997 4th Edition Garland Press, 1999.
Yoshihiro Oka, et al., "Cancer Immunotherapy Targeting Wilms' Tumor Gene WT1 Product", The Journal of Immunology, 164(4), 2000, 1873-1880.
Ann Van Driessche, et al., "Active Specific Immunotherapy Targeting the Wilms' Tumor Protein 1 (WT1) for Patients with Hematological Malignancies and Solid Tumors: Lessons from Early Clinical Trials", The Oncologist, 17(2), 2012, pp. 250-259.
Craig L. Slingluff Jr., "The Present and Future of Peptide Vaccines for Cancer: Single or Multiple, Long or Short, Alone or in Combination?", NIH Public Access Author Manuscript, Cancer Journal, 17(5), 2011, pp. 343-350.
Peter G. Maslak, et al., "Vaccination with synthetic analog peptides derived from WT1 oncoprotein induces T-cell responses in patients with complete remission from acute myeloid leukemia", Clinical Trials and Observations, Blood, 116(2), 2010, pp. 171-179.
Paul H. Naylor, et al., "Peptide Based Vaccine Approaches for Cancer—A Novel Approach Using a WT-1 Synthetic Long Peptide and the IRX-2 Immunomodulatory Regimen", Cancers, 3, 2011, pp. 3991-4009.

(56) References Cited

OTHER PUBLICATIONS

Shih-Chuung Chang, et al., "The ER aminopeptidase, ERAP1, trims precursors to lengths of MHC class I peptides by a 'molecular ruler' mechanism", Proceedings of the National Academy of Science of United States of America, 102(47), 2005, pp. 17107-17112.

Arron Hearn, et al., "The Specificity of Trimming of MHC Class I-Presented Peptides in the Endoplasmic Reticulum", The Journal of Immunology, 189(9), 2009, pp. 5526-5536.

Arron Hearn, et al., "Characterizing the Specificity and Cooperation of Aminopeptidases in the Cytosol and Endoplasmic Reticulum during MHC Class I Antigen Presentation", The Journal of Immunology, 184(9), 2010, pp. 4725-4732.

Norihiko Takahashi, et al., "First clinical trial of cancer vaccine therapy with artificially synthesized helper/killer-hybrid epitope long peptide of MAGE-A4 cancer antigen", Cancer Science, 103, 2012, pp. 150-153.

Francesca Di Modugno, et al, "MHC-Peptide Binding: Dimers of Cysteine-Containing Nonapeptides Bind with High Affinity to HLA-A2.1 Class I Molecules", Journal of Immunotherapy, 20(6), 1997, pp. 431-436.

Anthony W. Purcell, et al., "More than one reason to rethink the use of peptides in vaccine design", Nature Reviews Drug Discovery, 6(5), 2007, pp. 404-414.

Katherine M. Call, "Isolation and Characterization of a Zinc Finger Polypeptide Gene at the Human Chromosone 11 Wilms' Tumor Locus", Cell, 60(3), 1990, pp. 509-520.

Akihiro Tsuboi, et al., "Cytotoxic T-Lymphocyte Responses Elicited to Wilms' Tumor Gene WT1 Product by DNA Vaccination", Journal of Clinical Immunology, 20(3), 2000, pp. 195-202.

Kenneth L. Rock, et al., "Post-proteasomal antigen processing for major histocompatibility complex class I presentation", Nature Immunology, 5(7), 2004, pp. 670-677.

Sonia A. Perez, et al., "A New Era in Anticancer Peptide Vaccines", Cancer, 116(9), 2010, pp. 2071-2080.

Lee M. Krug, et al., "WT1 peptide vaccinations induce CD4 and CD8 T cell immune responses in patients with mesothelioma and non-small cell lung cancer", Cancer Immunol Immunother, 59, 2010, pp. 1467-1479.

Grazyna Kochan, et al., "Crystal structures of the endoplasmic reticulum aminopeptidase-1 (ERAP1) reveal the molecular basis for N-terminal peptide trimming", Proceedings of the National Academy of Science of United States of America, 108(19), 2011, pp. 7745-7750.

Tomo Saric, et al., "An IFN-γ-induced aminopeptidase in the ER, ERAP I, trims precursors to MHC class I-presented peptides", Nature Immunology, 3(12), 2002, pp. 1169-1176.

Ian A. York, et al., "The ER aminopeptidase ERAP I enhances or limits antigen presentation by trimming epitopes to 8-9 residues", Nature Immunology, 3(12), 2002, pp. 1177-1184.

Irini Evnouchidou, et al., "The Internal Sequence of the Peptide-Substrate Determines Its N-Terminus Trimming by ERAP1", PLoS One, 3(11), 2008, e3658, pp. 1-12.

Efthalia Zervoudi, et al., "Probing the S1 specificity pocket of the aminopeptidases that generate antigenic peptides", Biochemical Journal, 435, 2011, pp. 411-420.

Ian E. Gentle et al., "Direct Production of Proteins with N-Terminal Cysteine for Site-Specific Conjugation", Bioconjugate Chem., vol. 15, No. 3, 2004, pp. 658-663.

WT1 ANTIGEN PEPTIDE CONJUGATE VACCINE

CROSS-REFERENCE TO RELATED APPLICATIONS

This is a divisional of and claims the benefits of priority to U.S. Ser. No. 14/549,091, filed Nov. 20, 2014, which is a continuation of International Application No. PCT/JP2014/059336, filed Mar. 28, 2014, which claims the benefits of priority to Japanese Application No. 2013-072173, filed Mar. 29, 2013 and Japanese Application No. 2013-158383, filed Jul. 31, 2013. The entire contents of all of the above applications are incorporated herein by reference.

TECHNICAL FIELD OF THE INVENTION

1. Technical Field

The present invention belongs to the field of cancer immunotherapy, and relates to a conjugate vaccine that can be subjected to trimming by peptidase ERAP1, is obtained by conjugating peptide precursors derived from WT1 antigen protein via a sulfur-sulfur covalent bond, and efficiently induces cytotoxic T cells.

2. Background Art

For eradication of cancer cells in the body, cellular immunity, particularly cytotoxic T cell (cytotoxic T-lymphocyte, Cytotoxic T-cell, hereinafter to be referred to as CTL) mainly plays an important role. CTL is produced by differentiation and proliferation of a precursor T cell that recognized a complex formed by an antigen peptide derived from a cancer antigen protein (cancer antigen peptide) and an MHC class I molecule, and attacks cancer cells.

A cancer suppressor gene of Wilms tumor, WT1 (WT1 gene) is considered a new cancer antigen protein for leukemia and solid tumor (see non-patent document 1).

As for WT1 protein, for example, the following cancer antigen peptides that are bound to and presented by MHC class I have been reported (see patent documents 1, 2).

$WT1_{126-134}$ peptide: RMFPNAPYL (Arg-Met-Phe-Pro-Asn-Ala-Pro-Tyr-Leu) (SEQ ID NO: 2),
$WT1_{235-243}$ peptide: CMTWNQMNL (Cys-Met-Thr-Trp-Asn-Gln-Met-Asn-Leu) (SEQ ID NO: 3),
$WT1_{10-18}$ peptide: ALLPAVPSL (Ala-Leu-Leu-Pro-Ala-Val-Pro-Ser-Leu) (SEQ ID NO: 5),
$WT1_{187-195}$ peptide: SLGEQQYSV (Ser-Leu-Gly-Glu-Gln-Gln-Tyr-Ser-Val) (SEQ ID NO: 6),
$WT1_{302-310}$ peptide: RVPGVAPTL (Arg-Val-Pro-Gly-Val-Ala-Pro-Thr-Leu) (SEQ ID NO: 7) and the like.

In cancer immunotherapy, activation of helper T cell is also important for activating other T cells including CTL. In general, an antigen protein is degraded by intracellular lysosome, a part of peptide fragments constituted by a peptide consisting of about 13-17 amino acid residues binds as an antigen peptide to MHC class II molecule and is presented to helper T cell-TCR•CD3 complex to activate helper T cell. As for WT1 protein, for example, the following cancer antigen peptides that are presented by binding to MHC class II have been reported (see patent documents 3-5).
$WT1_{332-347}$ peptide: KRYFKLSHLQMHSRKH (Lys-Arg-Tyr-Phe-Lys-Leu-Ser-His-Leu-Gln-Met-His-Ser-Arg-Lys-His) (SEQ ID NO: 8), $WT1_{328-349}$ peptide: PGCNKRY-FKLSHLQMHSRKHTG (Pro-Gly-Cys-Asn-Lys-Arg-Tyr-Phe-Lys-Leu-Ser-His-Leu-Gln-Met-His-Ser-Arg-Lys-His-Thr-Gly) (SEQ ID NO: 10),
$WT1_{122-140}$ peptide: SGQARMFPNAPYLPSCLES (Ser-Gly-Gln-Ala-Arg-Met-Phe-Pro-Asn-Ala-Pro-Tyr-Leu-Pro-Ser-Cys-Leu-Glu-Ser) (SEQ ID NO: 11) and the like.

As a vaccine antigen of WT1, an antigen protein itself or the aforementioned antigen protein-derived antigen peptide is mainly used (see non-patent document 2). Since a cancer vaccine using a protein generally contains various cancer antigen peptides, it can simultaneously induce a plurality of CTLs and helper T cells. On the other hand, since the cancer protein vaccine possesses problems in stable supply and quality control, peptides that facilitate production and quality control are widely used as cancer antigen of WT1. Generally, however, since conventional peptide vaccines are mainly constituted by a single MHC class I-presented peptide antigen, it has been pointed out in recent years that efficient induction of CTL requires further improvement (see non-patent document 3).

One of the solving means is a multivalent antigen peptide presenting WT1 peptide cancer vaccine. As such peptide cancer vaccine, a cocktail vaccine containing a mixture of a plurality of peptide antigens presented by MHC class I and class II (see non-patent document 4), a long chain peptide vaccine containing peptide antigens presented by MHC class I and class II, which are bound by an amide bond, and the like have been reported (see non-patent document 5). In the case of a cocktail vaccine, however, since each peptide antigen composed of various amino acids shows various properties, the development of an optimal formulation capable of efficiently inducing CTL corresponding thereto is often problematic. In the case of a long chain peptide vaccine, the production thereof sometimes poses problems, like protein. Furthermore, since peptide antigens presented by class I and class II are bonded via any peptide spacer in a long chain peptide vaccine, control and prediction of the cleavage sites by intracellular enzyme are difficult. In the meantime, a peptide dimer wherein two peptide monomers are mutually bonded by a disulfide bond has been reported (see patent document 6). Different from cocktail vaccine, two single peptides are bonded, and therefore, they have single physical property and can be produced conveniently. On the other hand, to form a conjugate, WT1 cancer antigen peptides are required to contain cysteine in the amino acid sequence thereof, and therefore, applicable ones are limited. Furthermore, an altered compound obtained by condensing the N-terminal cysteine of cancer antigen peptide with cysteine, glutathione or thioglycolic acid by a disulfide bond has also been reported (see patent document 7).

The process of cancer antigen peptide presentation on MHC class I involves a plurality of peptidases. Of such peptidases, Endoplasmic reticulum aminopeptidase 1 (hereinafter to be referred to as ERAP1) is one of the trimming enzymes in the endoplasmic reticulum (hereinafter to be referred to as ER), and has been reported to recognize a particular antigen peptide sequence and the peptide length, and cleaves the cancer antigen peptide precursor from the N-terminal to control the length to be optimal for binding to MHC class I (see non-patent documents 6-8). However, there is no report to date on a WT1 peptide cancer antigen precursor containing cysteine, that is controlled in its length from the N-terminal, by the trimming function of ERAP1.

DOCUMENT LIST

Patent Documents patent document 1: WO 00/06602
patent document 2: WO 00/18795 patent document 3: WO 2005/045027
patent document 4: WO 2007/047764
patent document 5: WO 2007/120673
patent document 6: WO 2004/063217
patent document 7: WO 2007/063903

Non-Patent Documents non-patent document 1: The Journal of Immunology, 2000; 164(4); 1873-1880
non-patent document 2: The Oncologist, 2012; 17(2); 250-259
non-patent document 3: Cancer Journal, 2011; 17(5); 343-350
non-patent document 4: Blood, 2010; 166(2); 171-179
non-patent document 5: Cancers, 2011; 3; 3991-4009
non-patent document 6: Proceedings of the National Academy of Sciences of United States of America, 2005; 102 (47); 17107-17112
non-patent document 7: The Journal of Immunology, 2009; 183; 5526-5536
non-patent document 8: The Journal of Immunology, 2010; 184; 4725-4732

SUMMARY OF THE INVENTION

Problems to be Solved by the Invention

The problem to be solved by the present invention is to provide a WT1 conjugate vaccine that induces CTL efficiently.

Means of Solving the Problems

The present inventors have conducted intensive studies in an attempt to solve the aforementioned problem, and conceived, when considering adopting conjugate vaccine, an idea of adding cysteine in WT1 cancer antigen peptide, and further confirmed that the results of pharmacological tests and the like using in vivo animal model strongly suggest that ERAP1 cleaves cysteine from the N-terminal of a WT1 cancer antigen peptide precursor that is generated by intracellular reductive cleavage of disulfide bond, to efficiently convert the same to a cancer antigen peptide, which in turn led to the finding of a polyvalent antigen peptide presenting conjugate vaccine capable of inducing CTL in the body, and the completion of the present invention.

To be specific, during the process of studying the solving means to the above-mentioned problem, they have obtained an idea of a method for introducing cysteine, which is necessary for forming a conjugate of two different WT1 cancer antigen peptides, into any position of the N-terminal or C-terminal, without influencing the antigen presentation by MHC class I. As a result of further study, they have created a peptide by introducing 0-5 amino acids containing cysteine into the N terminal of a WT1 cancer antigen peptide, and a conjugate of the peptides containing a disulfide bond via cysteine. Furthermore, the present inventors have confirmed for the first time that said peptide and the conjugate are susceptible to trimming by ERAP1 in vitro and/or in vivo, which in turn results in the formation of a cancer antigen peptide, and thereby, completed the present invention.

While the development of a novel multivalent WT1 antigen peptide presenting peptide cancer vaccine, which can be produced easily, is applicable to various ones, and induces CTL with high efficiency, has been desired, the conjugate invented by the present inventors has enabled the development of a WT1 conjugate vaccine that induces CTL efficiently, is superior in physicochemical properties, can be produced easily, facilitates production management, and is applicable to various ones.

Accordingly, the present invention relates to the following.

1. First Embodiment

1. A compound represented by the formula (1):

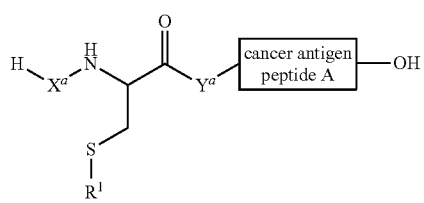

wherein $X^a$ and $Y^a$ are each independently a single bond or a divalent peptide group consisting of 1-4 amino acid residues, and a total of the amino acid residue number for $X^a$ and the amino acid residue number for $Y^a$ is an integer of 0-4, cancer antigen peptide A is an MHC class I-restricted WT1 peptide consisting of 7-30 amino acid residues, an amino group of an N-terminal amino acid of the cancer antigen peptide A binds to $Y^a$ in the formula (1), and a carbonyl group of a C-terminal amino acid of the cancer antigen peptide A binds to a hydroxyl group in the formula (1),
$R^1$ is a hydrogen atom, a group represented by the formula (2):

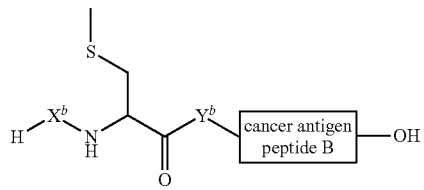

wherein $X^b$ and $Y^b$ are each independently a single bond or a divalent peptide group consisting of 1-4 amino acid residues, and a total of the amino acid residue number for $X^b$ and the amino acid residue number for $Y^b$ is an integer of 0-4, cancer antigen peptide B has a sequence different from that of the cancer antigen peptide A, and is an MHC class I-restricted WT1 peptide consisting of 7-30 amino acid residues, an amino group of an N-terminal amino acid of the cancer antigen peptide B binds to $Y^b$ in the formula (2), and a carbonyl group of a C-terminal amino acid of the cancer antigen peptide B binds to a hydroxyl group in the formula (2), and
a thioether group in the formula (2) binds to a thioether group in the formula (1),
or cancer antigen peptide C,
wherein the cancer antigen peptide C has a sequence different from that of the cancer antigen peptide A, and is an MHC class I-restricted WT1 peptide consisting of 7-30 amino acid residues containing one cysteine residue or an MHC class II-restricted WT1 peptide consisting of 7-30 amino acid residues containing one cysteine residue, and a thioether group of the cysteine residue of the cancer antigen peptide C binds to a thioether group in the formula (1), provided when $R^1$ is a hydrogen atom, the sequence of a compound represented by the formula (1) is not the same as the partial sequence of a WT1 protein,
or a pharmaceutically acceptable salt thereof;

2. the compound according to 1, wherein $X^a$ is a divalent peptide group consisting of 2 amino acid residues and $Y^a$ is a single bond, or $X^a$ and $Y^a$ are each independently a divalent peptide group consisting of 1 amino acid residue, or $X^a$ is a single bond and Y" is a divalent peptide group consisting of 2 amino acid residues, or $X^a$ is a divalent peptide group consisting of 1 amino acid residue and $Y^a$ is a single bond, or $X^a$ is a single bond and $Y^a$ is a divalent peptide group consisting of 1 amino acid residue, or $X^a$ and $Y^a$ are each a single bond, or a pharmaceutically acceptable salt thereof;

3. the compound according to 1 or 2, wherein $X^a$ is a single bond, and $Y^a$ is a single bond, an alanine residue, a leucine residue or a methionine residue, or a pharmaceutically acceptable salt thereof;

4. the compound according to 1 or 2, wherein $X^a$ is a single bond or a divalent peptide group consisting of 1 amino acid residue, and $Y^a$ is a single bond, or a pharmaceutically acceptable salt thereof;

5. the compound according to any one of 1-4, wherein $X^a$ and $Y^a$ are each a single bond, or a pharmaceutically acceptable salt thereof;

6. the compound according to any one of 1-5, wherein the cancer antigen peptide A is an MHC class I-restricted WT1 peptide consisting of 7-15 amino acid residues, or a pharmaceutically acceptable salt thereof;

7. the compound according to any one of 1-6, wherein the cancer antigen peptide A is a peptide comprising any amino acid sequence selected from the following amino acid sequences:

| | |
|---|---|
| RMFPNAPYL, | (SEQ ID NO: 2) |
| CMTWNQMNL, | (SEQ ID NO: 3) |
| ALLPAVPSL, | (SEQ ID NO: 5) |
| SLGEQQYSV and | (SEQ ID NO: 6) |
| RVPGVAPTL, | (SEQ ID NO: 7) | or a peptide comprising an altered amino acid sequence, which is any amino acid sequence selected from SEQ ID NOs: 2, 3, 5, 6 and 7 but containing alteration of amino acid residue(s), and having a CTL induction activity, or a pharmaceutically acceptable salt thereof;

8. the compound according to any one of 1-7, wherein the cancer antigen peptide A is a peptide consisting of any amino acid sequence selected from the following amino acid sequences:

| | |
|---|---|
| RMFPNAPYL, | (SEQ ID NO: 2) |
| CMTWNQMNL, | (SEQ ID NO: 3) |
| CYTWNQMNL, | (SEQ ID NO: 4) |
| ALLPAVPSL, | (SEQ ID NO: 5) |
| SLGEQQYSV and | (SEQ ID NO: 6) |
| RVPGVAPTL, | (SEQ ID NO: 7) | or a pharmaceutically acceptable salt thereof;

9. the compound according to any one of 1-8, wherein $R^1$ is a hydrogen atom, or a pharmaceutically acceptable salt thereof;

10. the compound according to any one of 1-9, wherein the compound represented by the formula (1) is a peptide consisting of any amino acid sequence selected from the following amino acid sequences:

| | |
|---|---|
| CRMFPNAPYL, | (SEQ ID NO: 13) |
| CCMTWNQMNL, | (SEQ ID NO: 14) |
| CCYTWNQMNL, | (SEQ ID NO: 15) |
| CALLPAVPSL, | (SEQ ID NO: 16) |
| CSLGEQQYSV and | (SEQ ID NO: 17) |
| CRVPGVAPTL, | (SEQ ID NO: 18) | or a pharmaceutically acceptable salt thereof;

11. the compound according to any one of 1-8, wherein $R^1$ is a group represented by the formula (2), or a pharmaceutically acceptable salt thereof;

12. the compound according to any one of 1-8 and 11, wherein $X^b$ is a divalent peptide group consisting of 2 amino acid residues and $Y^b$ is a single bond, or $X^b$ and $Y^b$ are each independently a divalent peptide group consisting of 1 amino acid residue, or $X^b$ is a single bond and $Y^b$ is a divalent peptide group consisting of 2 amino acid residues, or $X^b$ is a divalent peptide group consisting of 1 amino acid residue and $Y^b$ is a single bond, or $X^b$ is a single bond and $Y^b$ is a divalent peptide group consisting of 1 amino acid residue, or $X^b$ and $Y^b$ are each a single bond, or a pharmaceutically acceptable salt thereof;

13. the compound according to any one of 1-8 and 11-12, wherein $X^b$ is a single bond, and $Y^b$ is a single bond, an alanine residue, a leucine residue or a methionine residue, or a pharmaceutically acceptable salt thereof;

14. the compound according to any one of 1-8 and 11-12, wherein $X^b$ is a single bond or a divalent peptide group consisting of 1 amino acid residue, and $Y^b$ is a single bond, or a pharmaceutically acceptable salt thereof;

15. the compound according to any one of 1-8 and 11-14, wherein $X^b$ and $Y^b$ are each a single bond, or a pharmaceutically acceptable salt thereof;

16. the compound according to any one of 1-8 and 11-15, wherein the cancer antigen peptide B is an MHC class I-restricted WT1 peptide consisting of 7-15 amino acid residues, or a pharmaceutically acceptable salt thereof;

17. the compound according to any one of 1-8 and 11-16, wherein the cancer antigen peptide B is a peptide comprising any amino acid sequence selected from the following amino acid sequences:

| | |
|---|---|
| RMFPNAPYL, | (SEQ ID NO: 2) |
| CMTWNQMNL, | (SEQ ID NO: 3) |
| ALLPAVPSL, | (SEQ ID NO: 5) |
| SLGEQQYSV and | (SEQ ID NO: 6) |
| RVPGVAPTL, | (SEQ ID NO: 7) | or a peptide comprising an altered amino acid sequence, which is any amino acid sequence selected from SEQ ID NOs: 2, 3, 5, 6 and 7 but containing alteration of amino acid residue(s), and having a CTL induction activity, or a pharmaceutically acceptable salt thereof;

18. the compound according to any one of 1-8 and 11-17, wherein the cancer antigen peptide B is a peptide consisting of any amino acid sequence selected from the following amino acid sequences:

| | |
|---|---|
| RMFPNAPYL, | (SEQ ID NO: 2) |
| CMTWNQMNL, | (SEQ ID NO: 3) |
| CYTWNQMNL, | (SEQ ID NO: 4) |
| ALLPAVPSL, | (SEQ ID NO: 5) |
| SLGEQQYSV and | (SEQ ID NO: 6) |
| RVPGVAPTL, | (SEQ ID NO: 7) | or a pharmaceutically acceptable salt thereof;

19. the compound according to any one of 1-8 and 11-18, wherein the compound represented by the formula (1) is a compound represented by the formula (3):

$$\begin{array}{c} \text{CRMFPNAPYL} \\ | \\ \text{CSLGEQQYSV} \end{array} \quad (3)$$

wherein the bond between C and C is a disulfide bond, or a pharmaceutically acceptable salt thereof;

20. the compound according to any one of 1-8, wherein $R^1$ is cancer antigen peptide C, or a pharmaceutically acceptable salt thereof;

21. the compound according to any one of 1-8 and 20, wherein the cancer antigen peptide C is an MHC class I-restricted WT1 peptide consisting of 7-15 amino acid residues, or a pharmaceutically acceptable salt thereof;

22. the compound according to any one of 1-8 and 20-21, wherein the cancer antigen peptide C is a peptide comprising the following amino acid sequence:
CMTWNQMNL (SEQ ID NO: 3), or
a peptide comprising an altered amino acid sequence, which is the amino acid sequence of SEQ ID NO: 3 but containing alteration of amino acid residue(s), and having a CTL induction activity, or a pharmaceutically acceptable salt thereof;

23. the compound according to any one of 1-8 and 20-22, wherein the cancer antigen peptide C is a peptide consisting of any amino acid sequence selected from the following amino acid sequences:

| | |
|---|---|
| CMTWNQMNL and | (SEQ ID NO: 3) |
| CYTWNQMNL, | (SEQ ID NO: 4) | or a pharmaceutically acceptable salt thereof;

24. the compound according to any one of 1-8 and 20-23, wherein the compound represented by the formula (1) is a compound represented by the formula (4):

$$\begin{array}{c} \text{CRMFPNAPYL} \\ | \\ \text{CMTWNQMNL} \end{array} \quad (4)$$

wherein the bond between C and C is a disulfide bond, or a compound represented by the formula (5):

$$\begin{array}{c} \text{CRMFPNAPYL} \\ | \\ \text{CYTWNQMNL} \end{array} \quad (5)$$

wherein the bond between C and C is a disulfide bond, or a pharmaceutically acceptable salt thereof;

25. the compound according to any one of 1-8 and 20, wherein the cancer antigen peptide C is an MHC class II-restricted WT1 peptide consisting of 14-30 amino acid residues, or a pharmaceutically acceptable salt thereof;

26. the compound according to any one of 1-8, 20 and 25, wherein the cancer antigen peptide C is a peptide comprising any amino acid sequence selected from the following amino acid sequences:

| | |
|---|---|
| SGQARMFPNAPYLPSC, | (SEQ ID NO: 19) |
| SGQARMFPNAPYLPSCLES, | (SEQ ID NO: 11) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH and | (SEQ ID NO: 23) |
| CNKRYFKLSHLQMHSRKHTG, | (SEQ ID NO: 24) | or
a peptide comprising an altered amino acid sequence, which is any amino acid sequence selected from SEQ ID NOs: 10-11 and 19-24 but containing alteration of amino acid residue(s), and having a helper T cell induction activity, or a pharmaceutically acceptable salt thereof;

27. the compound according to any one of 1-8, 20 and 25-26, wherein the cancer antigen peptide C is a peptide consisting of an amino acid sequence selected from the following amino acid sequences:

| | |
|---|---|
| SGQARMFPNAPYLPSC, | (SEQ ID NO: 19) |
| SGQAYMFPNAPYLPSC, | (SEQ ID NO: 25) |
| SGQARMFPNAPYLPSCLES, | (SEQ ID NO: 11) |
| SGQAYMFPNAPYLPSCLES, | (SEQ ID NO: 12) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH and | (SEQ ID NO: 23) |
| CNKRYFKLSHLQMHSRKHTG, | (SEQ ID NO: 24) | or a pharmaceutically acceptable salt thereof;

28. the compound according to any one of 1-8, 20 and 25-27, wherein the compound represented by the formula (1) is a compound represented by the formula (6):

 (6)

wherein the bond between C and C is a disulfide bond, a compound represented by the formula (7):

 (7)

wherein the bond between C and C is a disulfide bond, a compound represented by the formula (8):

 (8)

wherein the bond between C and C is a disulfide bond, or a compound represented by the formula (9):

 (9)

wherein the bond between C and C is a disulfide bond,
or a pharmaceutically acceptable salt thereof;
29. a pharmaceutical composition comprising the compound according to any one of 1-28, or a pharmaceutically acceptable salt thereof, and a pharmaceutically acceptable carrier;
30. the pharmaceutical composition according to 29, which is used as a cancer vaccine;
31. use of the compound according to any one of 1-28 or a pharmaceutically acceptable salt thereof for the production of a cancer vaccine;
32. a method of treating or preventing cancer, comprising administering a therapeutically or prophylactically effective amount of the compound according to any one of 1-28 or a pharmaceutically acceptable salt thereof to a WT1 positive cancer patient in need thereof; and
33. a method of obtaining two different MHC class I-restricted epitopes, or an MHC class I-restricted epitope and an MHC class II-restricted epitope, comprising reacting the compound according to any one of 1-28 or a pharmaceutically acceptable salt thereof with ERAP1.

2. Second embodiment

1. A compound represented by the formula (1):

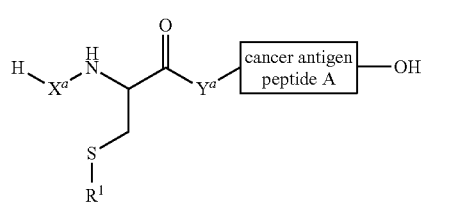 (1)

wherein $X^a$ and $Y^a$ are each independently a single bond or a divalent peptide group consisting of 1-4 amino acid residues, and a total of the amino acid residue number for $X^a$ and the amino acid residue number for $Y^a$ is an integer of 0-4, cancer antigen peptide A is an MHC class I-restricted WT1 peptide consisting of 7-30 amino acid residues, an amino group of an N-terminal amino acid of the cancer antigen peptide A binds to $Y^a$ in the formula (1), and a carbonyl group of a C-terminal amino acid of the cancer antigen peptide A binds to a hydroxyl group in the formula (1),
$R^1$ is a hydrogen atom, a group represented by the formula (2):

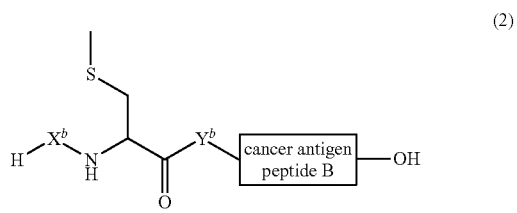 (2)

wherein $X^b$ and $Y^b$ are each independently a single bond or a divalent peptide group consisting of 1-4 amino acid residues, and a total of the amino acid residue number for $X^b$ and the amino acid residue number for $Y^b$ is an integer of 0-4, cancer antigen peptide B has a sequence different from that of the cancer antigen peptide A in the sequence and is an MHC class I-restricted WT1 peptide consisting of 7-30 amino acid residues, an amino group of an N-terminal amino acid of the cancer antigen peptide B binds to $Y^b$ in the formula (2), and a carbonyl group of a C-terminal amino acid of the cancer antigen peptide B binds to a hydroxyl group in the formula (2), and a thioether group in the formula (2) binds to a thioether group in the formula (1),
or cancer antigen peptide C,
wherein the cancer antigen peptide C is an MHC class I-restricted WT1 peptide different from the cancer antigen peptide A in the sequence and consisting of 7-30 amino acid residues containing one cysteine residue or an MHC class II-restricted WT1 peptide consisting of 7-30 amino acid residues containing one cysteine residue, and a thioether group of the cysteine residue of the cancer antigen peptide C binds to a thioether group in the formula (1),
provided when $R^1$ is a hydrogen atom, the sequence of the compound represented by the formula (1) is not the same as the partial sequence of a WT1 protein,
or a pharmaceutically acceptable salt thereof;
2. the compound according to 1, wherein $X^a$ is a divalent peptide group consisting of 2 amino acid residues and $Y^a$ is a single bond, or $X^a$ and $Y^a$ are each independently a divalent peptide group consisting of 1 amino acid residue, or $X^a$ is a single bond and $Y^a$ is a divalent peptide group consisting of 2 amino acid residues, or $X^a$ is a divalent peptide group consisting of 1 amino acid residue and $Y^a$ is a single bond, or $X^a$ is a single bond and $Y^a$ is a divalent peptide group consisting of 1 amino acid residue, or $X^a$ and $Y^a$ are each a single bond, or a pharmaceutically acceptable salt thereof;
3. the compound according to 1 or 2, wherein $X^a$ is a single bond, and $Y^a$ is a single bond, an alanine residue, a leucine residue or a methionine residue, or a pharmaceutically acceptable salt thereof;
4. the compound according to 1 or 2, wherein $X^a$ is a single bond or a divalent peptide group consisting of 1 amino acid residue, and $Y^a$ is a single bond, or a pharmaceutically acceptable salt thereof;
5. the compound according to any one of 1-4, wherein $X^a$ and $Y^a$ are each a single bond, or a pharmaceutically acceptable salt thereof;
6. the compound according to any one of 1-5, wherein the cancer antigen peptide A is an MHC class I-restricted WT1 peptide consisting of 7-15 amino acid residues, or a pharmaceutically acceptable salt thereof;

7. the compound according to any one of 1-6, wherein the cancer antigen peptide A is a peptide comprising any amino acid sequence selected from the following amino acid sequences:

```
RMFPNAPYL,       (SEQ ID NO: 2)

CMTWNQMNL,       (SEQ ID NO: 3)

ALLPAVPSL,       (SEQ ID NO: 5)

SLGEQQYSV        (SEQ ID NO: 6)
and

RVPGVAPTL,       (SEQ ID NO: 7)
```
or
a peptide comprising an altered amino acid sequence, which is any amino acid sequence selected from SEQ ID NOs: 2, 3, 5, 6 and 7 but containing alteration of amino acid residue(s), and having a CTL induction activity, or a pharmaceutically acceptable salt thereof;
8. the compound according to any one of 1-7, wherein the cancer antigen peptide A is a peptide consisting of any amino acid sequence selected from the following amino acid sequences:

```
RMFPNAPYL,       (SEQ ID NO: 2)

CMTWNQMNL,       (SEQ ID NO: 3)

CYTWNQMNL,       (SEQ ID NO: 4)

ALLPAVPSL,       (SEQ ID NO: 5)

SLGEQQYSV        (SEQ ID NO: 6)
and

RVPGVAPTL,       (SEQ ID NO: 7)
```
or a pharmaceutically acceptable salt thereof;
9. the compound according to any one of 1-8, wherein $R^1$ is a hydrogen atom, or a pharmaceutically acceptable salt thereof;
10. the compound according to any one of 1-9, wherein the compound represented by the formula (1) is a peptide consisting of any amino acid sequence selected from the following amino acid sequences:

```
CRMFPNAPYL,      (SEQ ID NO: 13)

CCMTWNQMNL,      (SEQ ID NO: 14)

CCYTWNQMNL,      (SEQ ID NO: 15)

CALLPAVPSL,      (SEQ ID NO: 16)

CSLGEQQYSV       (SEQ ID NO: 17)
and

CRVPGVAPTL,      (SEQ ID NO: 18)
```
or a pharmaceutically acceptable salt thereof;
11. the compound according to any one of 1-8, wherein Fe is a group represented by the formula (2), or a pharmaceutically acceptable salt thereof;
12. the compound according to any one of 1-8 and 11, wherein $X^b$ is a divalent peptide group consisting of 2 amino acid residues and $Y^b$ is a single bond, or $X^b$ and $Y^b$ are each independently a divalent peptide group consisting of 1 amino acid residue, or $X^b$ is a single bond and $Y^b$ is a divalent peptide group consisting of 2 amino acid residues, or $X^b$ is a divalent peptide group consisting of 1 amino acid residue and $Y^b$ is a single bond, or $X^b$ is a single bond and $Y^b$ is a divalent peptide group consisting of 1 amino acid residue, or $X^b$ and $Y^b$ are each a single bond, or a pharmaceutically acceptable salt thereof;
13. the compound according to any one of 1-8 and 11-12, wherein $X^b$ is a single bond, and $Y^b$ is a single bond, an alanine residue, a leucine residue or a methionine residue, or a pharmaceutically acceptable salt thereof;
14. the compound according to any one of 1-8 and 11-12, wherein $X^b$ is a single bond or a divalent peptide group consisting of 1 amino acid residue, and $Y^b$ is a single bond, or a pharmaceutically acceptable salt thereof;
15. the compound according to any one of 1-8 and 11-14, wherein $X^b$ and $Y^b$ are each a single bond, or a pharmaceutically acceptable salt thereof;
16. the compound according to any one of 1-8 and 11-15, wherein the cancer antigen peptide B is an MHC class I-restricted WT1 peptide consisting of 7-15 amino acid residues, or a pharmaceutically acceptable salt thereof;
17. the compound according to any one of 1-8 and 11-16, wherein the cancer antigen peptide B is a peptide comprising any amino acid sequence selected from the following amino acid sequences:

```
RMFPNAPYL,       (SEQ ID NO: 2)

CMTWNQMNL,       (SEQ ID NO: 3)

ALLPAVPSL,       (SEQ ID NO: 5)

SLGEQQYSV        (SEQ ID NO: 6)
and

RVPGVAPTL,       (SEQ ID NO: 7)
```
or
a peptide comprising an altered amino acid sequence, which is any amino acid sequence selected from SEQ ID NOs: 2, 3, 5, 6 and 7 but containing alteration of amino acid residue(s), and having a CTL induction activity, or a pharmaceutically acceptable salt thereof;
18. the compound according to any one of 1-8 and 11-17, wherein the cancer antigen peptide B is a peptide consisting of any amino acid sequence selected from the following amino acid sequences:

```
RMFPNAPYL,       (SEQ ID NO: 2)

CMTWNQMNL,       (SEQ ID NO: 3)

CYTWNQMNL,       (SEQ ID NO: 4)

ALLPAVPSL,       (SEQ ID NO: 5)

SLGEQQYSV        (SEQ ID NO: 6)
and

RVPGVAPTL,       (SEQ ID NO: 7)
```
or a pharmaceutically acceptable salt thereof;
19. the compound according to any one of 1-8 and 11-18, wherein the compound represented by the formula (1) is a compound represented by the formula (3):

$$\begin{array}{l} \text{CRMFPNAPYL} \\ | \\ \text{CSLGEQQYSV} \end{array} \quad (3)$$

wherein the bond between C and C is a disulfide bond, or a pharmaceutically acceptable salt thereof;

20. the compound according to 13, wherein $Y^b$ is an alanine residue, or a pharmaceutically acceptable salt thereof;

21. the compound according to any one of 1-8 and 11-13 and 20, wherein, when the cancer antigen peptide B is an MHC class I-restricted WT1 peptide containing one cysteine residue, the thioether group in the cancer antigen peptide B is bonded to the thioether group in the formula (16):

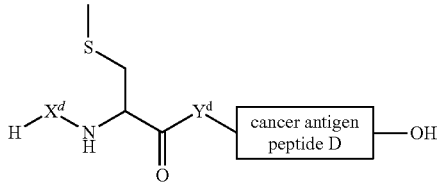

(16)

wherein $X^d$ and $Y^d$ are each independently a single bond or a divalent peptide group consisting of 1-4 amino acid residues, and a total of the amino acid residue number for $X^d$ and the amino acid residue number for $Y^d$ is an integer of 0-4, cancer antigen peptide D is an MHC class II-restricted WT1 peptide consisting of 7-30 amino acid residues, an amino group of an N-terminal amino acid of the cancer antigen peptide D binds to $Y^d$ in the formula (16), and a carbonyl group of a C-terminal amino acid of the cancer antigen peptide D binds to a hydroxyl group in the formula (16), or to the thioether group of the cysteine residue of the cancer antigen peptide E, which is an MHC class II-restricted WT1 peptide consisting of 7-30 amino acid residues containing one cysteine residue, or a pharmaceutically acceptable salt thereof;

22. the compound according to 21, wherein the cancer antigen peptide B is an MHC class I-restricted WT1 peptide consisting of 7-15 amino acid residues, or a pharmaceutically acceptable salt thereof;

23. the compound according to any one of 21-22, wherein the cancer antigen peptide B is a peptide consisting of any amino acid sequence selected from the following amino acid sequences:

| CMTWNQMNL and | (SEQ ID NO: 3) |
|---|---|
| CYTWNQMNL, | (SEQ ID NO: 4) | or a pharmaceutically acceptable salt thereof;

24. the compound according to any one of 21-23, wherein $X^d$ is a divalent peptide group consisting of 2 amino acid residues and $Y^d$ is a single bond, or $X^d$ and $Y^d$ are each independently a divalent peptide group consisting of 1 amino acid residue, or $X^d$ is a single bond and $Y^d$ is a divalent peptide group consisting of 2 amino acid residues, or $X^d$ is a divalent peptide group consisting of 1 amino acid residue and $Y^d$ is a single bond, or $X^d$ is a single bond and $Y^d$ is a divalent peptide group consisting of 1 amino acid residue, or $X^d$ and $Y^d$ are each a single bond, or a pharmaceutically acceptable salt thereof;

25. the compound according to any one of 21-24, wherein $X^d$ is a single bond, $Y^d$ is a single bond, an alanine residue, a leucine residue or a methionine residue, or a pharmaceutically acceptable salt thereof;

26. the compound according to any one of 21-24, wherein $X^d$ is a single bond or a divalent peptide group consisting of one amino acid residue, and $Y^d$ is a single bond, or a pharmaceutically acceptable salt thereof;

27. the compound according to any one of 21-26, wherein $X^d$ and $Y^d$ are each a single bond, or a pharmaceutically acceptable salt thereof;

28. the compound according to any one of 21-27, wherein the cancer antigen peptide D is an MHC class II-restricted WT1 peptide consisting of 14-30 amino acid residues, or a pharmaceutically acceptable salt thereof;

29. the compound according to any one of 21-28, wherein the cancer antigen peptide D is a peptide consisting of any amino acid sequence selected from the following amino acid sequences:

| SGQARMFPNAPYLPSC, | (SEQ ID NO: 19) |
|---|---|
| SGQAYMFPNAPYLPSC, | (SEQ ID NO: 25) |
| SGQARMFPNAPYLPSCLES, | (SEQ ID NO: 11) |
| SGQAYMFPNAPYLPSCLES, | (SEQ ID NO: 12) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH, | (SEQ ID NO: 23) |
| CNKRYFKLSHLQMHSRKHTG and | (SEQ ID NO: 24) |
| WAPVLDFAPPGASAYGSL, | (SEQ ID NO: 244) | or a pharmaceutically acceptable salt thereof;

30. the compound according to any one of 1-8, 11-13 and 20-29, wherein the compound represented by the formula (1) is a compound represented by the formula (15):

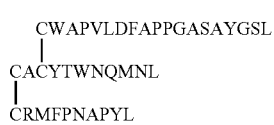

(15)

wherein the bond between C and C is a disulfide bond, or a pharmaceutically acceptable salt thereof;

31. the compound according to any one of 21-23, wherein the cancer antigen peptide E is an MHC class II-restricted WT1 peptide consisting of 14-30 amino acid residues, or a pharmaceutically acceptable salt thereof;

32. the compound according to any one of 21-23 and 31, wherein the cancer antigen peptide E is a peptide consisting of any amino acid sequence selected from the following amino acid sequences:

| SGQARMFPNAPYLPSC, | (SEQ ID NO: 19) |
|---|---|
| SGQAYMFPNAPYLPSC, | (SEQ ID NO: 25) |
| SGQARMFPNAPYLPSCLES, | (SEQ ID NO: 11) |
| SGQAYMFPNAPYLPSCLES, | (SEQ ID NO: 12) |
| PGCNKRYFKLSHLQMHSRK, | (SEQ ID NO: 20) |

```
PGCNKRYFKLSHLQMHSRKH,         (SEQ ID NO: 21)

PGCNKRYFKLSHLQMHSRKHTG,       (SEQ ID NO: 10)

CNKRYFKLSHLQMHSRK,            (SEQ ID NO: 22)

CNKRYFKLSHLQMHSRKH            (SEQ ID NO: 23)
and

CNKRYFKLSHLQMHSRKHTG,         (SEQ ID NO: 24)
``` or a pharmaceutically acceptable salt thereof;

33. the compound according to any one of 1-8, wherein $R^1$ is cancer antigen peptide C, or a pharmaceutically acceptable salt thereof;

34. the compound according to any one of 1-8 and 33, wherein the cancer antigen peptide C is an MHC class I-restricted WT1 peptide consisting of 7-15 amino acid residues, or a pharmaceutically acceptable salt thereof;

35. the compound according to any one of 1-8 and 33-34, wherein the cancer antigen peptide C is a peptide comprising the following amino acid sequence:

```
        CMTWNQMNL,            (SEQ ID NO: 3)
``` or a peptide comprising an altered amino acid sequence, which is the amino acid sequence of SEQ ID NO: 3 but containing alteration of amino acid residue(s), and having a CTL induction activity, or a pharmaceutically acceptable salt thereof;

36. the compound according to any one of 1-8 and 33-35, wherein the cancer antigen peptide C is a peptide consisting of any amino acid sequence selected from the following amino acid sequences:

```
        CMTWNQMNL             (SEQ ID NO: 3)
        and

CYTWNQMNL,            (SEQ ID NO: 4)
``` or a pharmaceutically acceptable salt thereof;

37. the compound according to any one of 1-8 and 33-36, wherein the compound represented by the formula (1) is a compound represented by the formula (4):

(4)

wherein the bond between C and C is a disulfide bond, or a compound represented by the formula (5):

(5)

wherein the bond between C and C is a disulfide bond, or a pharmaceutically acceptable salt thereof;

38. the compound according to any one of 1-8 and 33, wherein, when the peptide consisting of 1-4 amino acid residues containing one cysteine residue is further bonded to the N-terminal of the cancer antigen peptide C, the thioether group of the cysteine residue of the peptide bonded to the N-terminal of the cancer antigen peptide C is bonded to the thioether group in the formula (16):

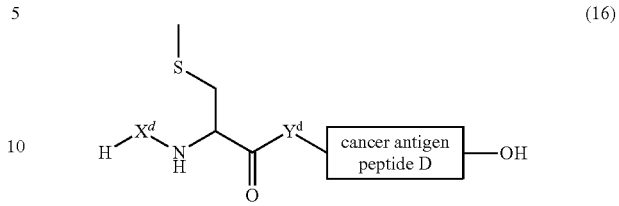

(16)

wherein $X^d$ and $Y^d$ are each independently a single bond or a divalent peptide group consisting of 1-4 amino acid residues, and a total of the amino acid residue number for $X^d$ and the amino acid residue number for $Y^d$ is an integer of 0-4, cancer antigen peptide D is an MHC class II-restricted WT1 peptide consisting of 7-30 amino acid residues, an amino group of an N-terminal amino acid of the cancer antigen peptide D binds to $Y^d$ in the formula (16), and a carbonyl group of a C-terminal amino acid of the cancer antigen peptide D binds to a hydroxyl group in the formula (16), or to the thioether group of the cysteine residue of the cancer antigen peptide E, which is an MHC class II-restricted WT1 peptide consisting of 7-30 amino acid residues containing one cysteine residue, or a pharmaceutically acceptable salt thereof;

39. the compound according to 38, wherein the peptide consisting of 1-4 amino acid residues containing one cysteine residue bonded to the N-terminal of the cancer antigen peptide C is a dipeptide consisting of CA, or a pharmaceutically acceptable salt thereof;

40. the compound according to any one of 38-39, wherein the cancer antigen peptide C is an MHC class I-restricted WT1 peptide consisting of 7-15 amino acid residues, or a pharmaceutically acceptable salt thereof;

41. the compound according to any one of 38-40, wherein the cancer antigen peptide C is a peptide consisting of any amino acid sequence selected from the following amino acid sequences:

```
        CMTWNQMNL             (SEQ ID NO: 3)
        and

CYTWNQMNL,            (SEQ ID NO: 4)
``` or a pharmaceutically acceptable salt thereof;

42. the compound according to any one of 38-41, wherein $X^d$ is a divalent peptide group consisting of 2 amino acid residues and $Y^d$ is a single bond, or $X^d$ and $Y^d$ are each independently a divalent peptide group consisting of 1 amino acid residue, or $X^d$ is a single bond and $Y^d$ is a divalent peptide group consisting of 2 amino acid residues, or $X^d$ is a divalent peptide group consisting of 1 amino acid residue and $Y^d$ is a single bond, or $X^d$ is a single bond and $Y^d$ is a divalent peptide group consisting of 1 amino acid residue, or $X^d$ and $Y^d$ are each a single bond, or a pharmaceutically acceptable salt thereof;

43. the compound according to any one of 38-42, wherein $X^d$ is a single bond, and $Y^d$ is a single bond, an alanine residue, a leucine residue or a methionine residue, or a pharmaceutically acceptable salt thereof;

44. the compound according to any one of 38-42, wherein $X^d$ is a single bond or a divalent peptide group consisting of 1 amino acid residue, and $Y^d$ is a single bond, or a pharmaceutically acceptable salt thereof;

45. the compound according to any one of 38-44, wherein $X^d$ and $Y^d$ are each a single bond, or a pharmaceutically acceptable salt thereof;

46. the compound according to any one of 38-45, wherein the cancer antigen peptide D is an MHC class II-restricted WT1 peptide consisting of 14-30 amino acid residues, or a pharmaceutically acceptable salt thereof;

47. the compound according to any one of 38-46, wherein the cancer antigen peptide D is a peptide consisting of any amino acid sequence selected from the following amino acid sequences:

| | |
|---|---|
| SGQARMFPNAPYLPSC, | (SEQ ID NO: 19) |
| SGQAYMFPNAPYLPSC, | (SEQ ID NO: 25) |
| SGQARMFPNAPYLPSCLES, | (SEQ ID NO: 11) |
| SGQAYMFPNAPYLPSCLES, | (SEQ ID NO: 12) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH, | (SEQ ID NO: 23) |
| CNKRYFKLSHLQMHSRKHTG and | (SEQ ID NO: 24) |
| WAPVLDFAPPGASAYGSL | (SEQ ID NO: 244) | or a pharmaceutically acceptable salt thereof;

48. the compound according to any one of 38-47, wherein the compound represented by the formula (1) is a compound represented by the formula (14):

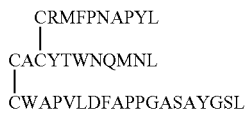
(14)

wherein the bond between C and C is a disulfide bond, or a pharmaceutically acceptable salt thereof;

49. the compound according to any one of 38-41 and 44, wherein the cancer antigen peptide E is a peptide consisting of any amino acid sequence selected from the following amino acid sequences:

| | |
|---|---|
| SGQARMFPNAPYLPSC, | (SEQ ID NO: 19) |
| SGQAYMFPNAPYLPSC, | (SEQ ID NO: 25) |
| SGQARMFPNAPYLPSCLES, | (SEQ ID NO: 11) |
| SGQAYMFPNAPYLPSCLES, | (SEQ ID NO: 12) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH and | (SEQ ID NO: 23) |
| CNKRYFKLSHLQMHSRKHTG | (SEQ ID NO: 24) | or a pharmaceutically acceptable salt thereof;

50. the compound according to any one of 38-41 and 49, wherein the compound represented by the formula (1) is a compound represented by the formula (12):

wherein the bond between C and C is a disulfide bond, or a pharmaceutically acceptable salt thereof;

51. the compound according to any one of 1-8 and 33, wherein the cancer antigen peptide C is an MHC class II-restricted WT1 peptide consisting of 14-30 amino acid residues, or a pharmaceutically acceptable salt thereof;

52. the compound according to any one of 1-8, 33 and 51, wherein the cancer antigen peptide C is a peptide comprising any amino acid sequence selected from the following amino acid sequences:

| | |
|---|---|
| SGQARMFPNAPYLPSC, | (SEQ ID NO: 19) |
| SGQARMFPNAPYLPSCLES, | (SEQ ID NO: 11) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH and | (SEQ ID NO: 23) |
| CNKRYFKLSHLQMHSRKHTG, | (SEQ ID NO: 24) | or
a peptide comprising an altered amino acid sequence, which is any amino acid sequence selected from SEQ ID NOs: 10-11 and 19-24 but containing alteration of amino acid residue(s), and having a helper T cell induction activity, or a pharmaceutically acceptable salt thereof;

53. the compound according to any one of 1-8, 33 and 51-52, wherein the cancer antigen peptide C is a peptide consisting of an amino acid sequence selected from the following amino acid sequences:

| | |
|---|---|
| SGQARMFPNAPYLPSC, | (SEQ ID NO: 19) |
| SGQAYMFPNAPYLPSC, | (SEQ ID NO: 25) |
| SGQARMFPNAPYLPSCLES, | (SEQ ID NO: 11) |
| SGQAYMFPNAPYLPSCLES, | (SEQ ID NO: 12) |
| PGCNKRYFKLSHLQMHSRK, | (SEQ ID NO: 20) |
| PGCNKRYFKLSHLQMHSRKH, | (SEQ ID NO: 21) |
| PGCNKRYFKLSHLQMHSRKHTG, | (SEQ ID NO: 10) |
| CNKRYFKLSHLQMHSRK, | (SEQ ID NO: 22) |
| CNKRYFKLSHLQMHSRKH and | (SEQ ID NO: 23) |
| CNKRYFKLSHLQMHSRKHTG | (SEQ ID NO: 24) | or a pharmaceutically acceptable salt thereof;

54. the compound according to any one of 1-8, 33 and 51-53, wherein the compound represented by the formula (1) is a compound represented by the formula (6):

$$\begin{array}{r}\text{CRMFPNAPYL}\\|\\\text{CNKRYFKLSHLQMHSRKHTG}\end{array} \quad (6)$$

wherein the bond between C and C is a disulfide bond, a compound represented by the formula (7):

$$\begin{array}{r}\text{CRMFPNAPYL}\\|\\\text{CNKRYFKLSHLQMHSRKH}\end{array} \quad (7)$$

wherein the bond between C and C is a disulfide bond, a compound represented by the formula (8):

$$\begin{array}{r}\text{CRMFPNAPYL}\\|\\\text{CNKRYFKLSHLQMHSRK}\end{array} \quad (8)$$

wherein the bond between C and C is a disulfide bond, or a compound represented by the formula (9):

$$\begin{array}{r}\text{CALLPAVPSL}\\|\\\text{CNKRYFKLSHLQMHSRKHTG}\end{array} \quad (9)$$

wherein the bond between C and C is a disulfide bond, or a pharmaceutically acceptable salt thereof;
55. an altered form of an MHC class II-restricted WT1 peptide consisting of 7-30 amino acid residues;
56. the altered form according to 55, which is the following amino acid sequence:

| CWAPVLDFAPPGASAYGSL | (SEQ ID NO: 242) |
| or | |
| WAPVLDFAPPGASAYGSLC; | (SEQ ID NO: 243) |

57. a compound represented by the formula (10):

$$\begin{array}{r}\text{CRMFPNAPYL}\\|\\\text{CWAPVLDFAPPGASAYGSL}\end{array} \quad (10)$$

wherein the bond between C and C is a disulfide bond, or a pharmaceutically acceptable salt thereof;
58. a composition comprising a compound selected from the group consisting of a compound represented by the formula (3):

$$\begin{array}{r}\text{CRMFPNAPYL}\\|\\\text{CSLGEQQYSV}\end{array} \quad (3)$$

wherein the bond between C and C is a disulfide bond, a compound represented by the formula (4):

$$\begin{array}{r}\text{CRMFPNAPYL}\\|\\\text{CMTWNQMNL}\end{array} \quad (4)$$

wherein the bond between C and C is a disulfide bond, and a compound represented by the formula (5):

$$\begin{array}{r}\text{CRMFPNAPYL}\\|\\\text{CYTWNQMNL}\end{array} \quad (5)$$

wherein the bond between C and C is a disulfide bond, and a peptide consisting of an amino acid sequence selected from the group consisting of the following amino acid sequences:

| CNKRYFKLSHLQMHSRK, | (SEQ ID NO: 22) |
| CNKRYFKLSHLQMHSRKH, | (SEQ ID NO: 23) |
| CNKRYFKLSHLQMHSRKHTG, | (SEQ ID NO: 24) |
| WAPVLDFAPPGASAYGSL, | (SEQ ID NO: 244) |
| CWAPVLDFAPPGASAYGSL and | (SEQ ID NO: 242) |
| WAPVLDFAPPGASAYGSLC; | (SEQ ID NO: 243) |

59. a pharmaceutical composition comprising the compound according to any one of 1-54 and 57, or a pharmaceutically acceptable salt thereof, or the composition according to 58 and a pharmaceutically acceptable carrier;
60. the pharmaceutical composition according to 59, which is used as a cancer vaccine;
61. use of the compound according to any one of 1-54 and 57, or a pharmaceutically acceptable salt thereof, or the composition according to 58 for the production of a cancer vaccine;
62. a method of treating or preventing cancer, comprising administering a therapeutically or prophylactically effective amount of the compound according to any one of 1-54 and 57 or a pharmaceutically acceptable salt thereof or the composition according to 58 to a WT1 positive cancer patient in need thereof;
63. a method of obtaining two different MHC class I-restricted epitopes, or an MHC class I-restricted epitope and an MHC class II-restricted epitope, comprising reacting the compound according to any one of 1-54 and 57 or a pharmaceutically acceptable salt thereof with ERAP1; and
64. a method of synthesizing a compound, comprising the following steps:
(1) a step of synthesizing, by using Fmoc-C(Mmt)A-SBn and cancer antigen peptide C, a peptide wherein a carbonyl group of the C-terminal amino acid of C(Mmt)A and the N-terminal amino group of the cancer antigen peptide C are bonded, wherein the antigen peptide C is an MHC class I-restricted WT1 peptide consisting of 7-30 amino acid residues containing one cysteine residue or an MHC class II-restricted WT1 peptide consisting of 7-30 amino acid residues containing one cysteine residue,
(2) a step of synthesizing, by using the peptide obtained in the aforementioned step (1) and cancer antigen peptide A wherein one cysteine residue protected by Npys group is bonded to the N-terminal, a peptide wherein a thioether group of the cysteine residue of the cancer antigen peptide C in the peptide obtained in the aforementioned step (1) and a thioether group of the cysteine residue bonded to the N-terminal of cancer antigen peptide A are bonded, wherein the cancer antigen peptide A is an MHC class I-restricted WT1 peptide consisting of 7-30 amino acid residues, and
(3) a step of synthesizing, by using the peptide obtained in the aforementioned step (2) and cancer antigen peptide D containing a cysteine residue protected by Spy group, a peptide wherein a thioether group of the cysteine residue bonded to the N-terminal of the cancer antigen peptide A in the peptide obtained in the aforementioned step (2), and a thioether group of the cysteine residue of the cancer antigen peptide D are bonded, wherein the cancer antigen peptide D is an MHC class II-restricted WT1 peptide consisting of 7-30 amino acid residues containing one cysteine residue bonded to the N terminal or an MHC class II-restricted WT1 peptide consisting of 7-30 amino acid residues containing one cysteine residue,

3. Third Embodiment

1. A compound represented by the formula (1)

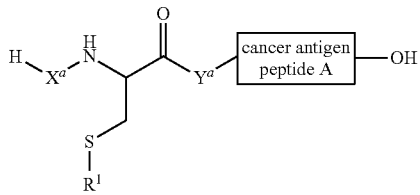
(1)

wherein $X^a$ and $Y^a$ are each a single bond, cancer antigen peptide A is a peptide consisting of any amino acid sequence selected from the following amino acid sequences:

```
RMFPNAPYL,      (SEQ ID NO: 2)
ALLPAVPSL,      (SEQ ID NO: 5)
SLGEQQYSV       (SEQ ID NO: 6)
and
RVPGVAPTL,      (SEQ ID NO: 7)
``` an amino group of an N-terminal amino acid of the cancer antigen peptide A binds to $Y^a$ in the formula (1), and a carbonyl group of a C-terminal amino acid of the cancer antigen peptide A binds to a hydroxyl group in the formula (1),
$R^1$ is a cancer antigen peptide C,
the cancer antigen peptide C has a sequence different from that of the cancer antigen peptide A, which is a peptide consisting of any amino acid sequence selected from the following amino acid sequences:

```
CMTWNQMNL       (SEQ ID NO: 3)
and

CYTWNQMNL,      (SEQ ID NO: 4)
``` residue of the cancer antigen peptide C is bonded to the thioether group in the formula (1),
or a pharmaceutically acceptable salt thereof;
2. the compound according to 1, wherein the compound represented by the formula (1) is a compound represented by the formula (4):

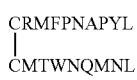
(4)

wherein the bond between C and C is a disulfide bond, or a pharmaceutically acceptable salt thereof;

3. the compound according to 1, wherein the compound represented by the formula (1) is a compound represented by the formula (5):

(5)

wherein the bond between C and C is a disulfide bond, or a pharmaceutically acceptable salt thereof;
4. a pharmaceutical composition comprising the compound according to any one of 1-3, or a pharmaceutically acceptable salt thereof, and a pharmaceutically acceptable carrier;
5. the pharmaceutical composition according to 4, comprising at least one peptide consisting of an amino acid sequence selected from the group consisting of the following amino acid sequences:

```
CNKRYFKLSHLQMHSRK,        (SEQ ID NO: 22)
CNKRYFKLSHLQMHSRKH,       (SEQ ID NO: 23)
CNKRYFKLSHLQMHSRKHTG,     (SEQ ID NO: 24)
WAPVLDFAPPGASAYGSL,       (SEQ ID NO: 244)
CWAPVLDFAPPGASAYGSL       (SEQ ID NO: 242)
and
WAPVLDFAPPGASAYGSLC;      (SEQ ID NO: 243)
``` and
6. a composition comprising a compound selected from the group consisting of a compound represented by the formula (4):

(4)

wherein the bond between C and C is a disulfide bond, and a compound represented by the formula (5):

(5)

wherein the bond between C and C is a disulfide bond, and at least one peptide consisting of an amino acid sequence selected from the group consisting of the following amino acid sequences:

```
CNKRYFKLSHLQMHSRK,        (SEQ ID NO: 22)
CNKRYFKLSHLQMHSRKH,       (SEQ ID NO: 23)
CNKRYFKLSHLQMHSRKHTG,     (SEQ ID NO: 24)
WAPVLDFAPPGASAYGSL,       (SEQ ID NO: 244)
CWAPVLDFAPPGASAYGSL       (SEQ ID NO: 242)
and
WAPVLDFAPPGASAYGSLC.      (SEQ ID NO: 243)
```

Effect of the Invention

According to the present invention, the aforementioned compound represented by the formula (1) useful as a cancer immunotherapeutic agent (hereinafter sometimes to be referred to as the compound of the present invention) can be provided. According to the compound of the present invention, cancer vaccines and cancer immunotherapeutic agents that efficiently induce CTL in vivo and in vitro can be provided. To be specific, according to the compound of the present invention, it is now possible to produce two MHC class I-restricted WT1 peptides having different sequences or two MHC class I-restricted WT1 epitopes having different sequences, an MHC class I-restricted WT1 peptide and an MHC class II-restricted WT1 peptide, an MHC class I-restricted WT1 epitope and an MHC class II-restricted WT1 epitope, two MHC class I-restricted WT1 peptide and MHC class II-restricted WT1 peptide having different sequences, or two MHC class I-restricted WT1 epitope and MHC class II-restricted WT1 epitope having different sequences in vivo and in vitro and efficiently induce CTL.

As for the HLA subtypes of two MHC class I-restricted WT1 peptides having different sequence, the compound of the present invention (conjugate) obtained by combining A02 type (A-0201, A0206 and the like) peptide and A24 type (A-2402 and the like) peptide is particularly preferable. In Europeans and Americans (Caucasian), the population of HLA-A0201 subtype or HLA-A0206 subtype is the highest and about 470, then HLA-A2402 subtype is about 13%, and the total of these subtypes occupies about 56%, excluding duplicates (i.e., duplicate calculation of humans having both subtypes) (Human Immunol. 62:1009; 2001). In Japanese people and the like, the population of HLA-A2402 is the highest and about 60%, then HLA-A0201 or HLA-A0206 is about 39%, and the total of these subtypes occupies about 81%, excluding duplicates (i.e., duplicate calculation of humans having both subtypes) (www.bmdc.irc.or.jp/GF-A.htm). Therefore, the advantages of the compound of the present invention are, specifically, that a larger population is covered by a single compound of the present invention, and selection of the HLA subtype of the patients before administration is not always essential and the like. In view of such advantages of the compound of the present invention, a compound represented by the formula (3), the formula (4) or the formula (5) is preferable, and a compound represented by the formula (5) is more preferable.

Moreover, according to the compound of the present invention, an active ingredient of a cancer vaccine superior in physicochemical properties and stability, and easily produced and easily controlled can be provided. As a result, formulation of cancer vaccine has been facilitated.

Specifically, examples of the physicochemical properties include solubility, viscosity of solution, easiness of purification resulting therefrom, easy handling after freeze-drying, easiness of purification resulting therefrom and the like. The stability includes stability after salt substitution, hygroscopicity, thermal stability, stability after emulsion formation and the like. The pharmacological activity includes efficacy as cancer vaccine, difference caused by API (Active Pharmaceutical Ingredient), interaction with additive in preparation and the like. Of these, the difference caused by API is a difference as a cancer vaccine due to API. Specifically, in two APIs having vastly different solubilities, API with smaller solubility is prone to precipitate, and it is easily expected that a sterilization treatment by filtration with a membrane filter, which is an essential requirement for pharmaceutical products, cannot be performed. Even if a sterilization treatment by filtration of API with small solubility is barely possible, it is considered that the amount of API contained in the filtrate markedly decreases and CTL induction ability essential for a cancer vaccine markedly decreases. Therefore, a demerit of markedly decreased production efficiency of API with small solubility is easily predictable.

DESCRIPTION OF EMBODIMENTS

Figure 1:
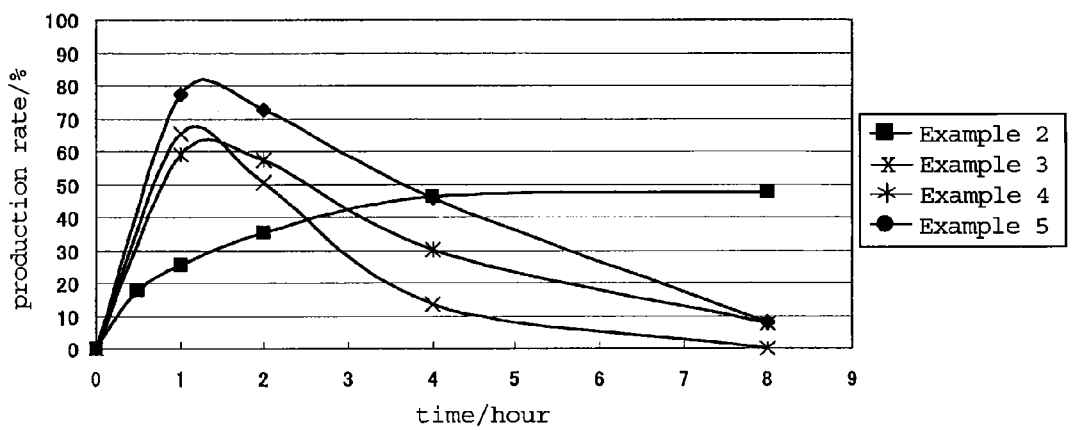
FIG. 1 is a Figure showing the test results of Experimental Example 1 as to the time-dependent change of N-terminal amino acid trimming by ERAP1 of each peptide of SEQ ID NOs: 13, 16, 17 and 18 synthesized in Examples 2-5.

The embodiment of the present invention is explained in detail in the following.

The "amino acid residue" in the present invention means a region corresponding to one unit of amino acid constituting a peptide or protein in a peptide or protein molecule. Examples of the "amino acid residue" include natural or non-natural α-amino acid residue, (3-amino acid residue, γ-amino acid residue or δ-amino acid residue. Specific examples thereof include natural α-amino acid residue, ornithine residue, homoserine residue, homocysteine residue, (3-alanine, γ-aminobutanoic acid or δ-aminopentanoic acid and the like. When the "amino acid residue" can be an optically active substance, it may be any of an L-form and a D-form, and an L-form is preferable.

When the "amino acid residue" in the present invention is shown in abbreviation, the following abbreviations are used.
Ala or A: alanine residue
Arg or R: arginine residue
Asn or N: asparagine residue
Asp or D: aspartic acid residue
Cys or C: cysteine residue
Gln or Q: glutamine residue
Glu or E: glutamic acid residue
Gly or G: glycine residue
His or H: histidine residue
Ile or I: isoleucine residue Leu or L: leucine residue
Lys or K: lysine residue
Met or M: methionine residue
Phe or F: phenylalanine residue
Pro or P: proline residue
Ser or S: serine residue
Thr or T: threonine residue
Trp or W: tryptophan residue
Tyr or Y: tyrosine residue
Val or V: valine residue
Abu: 2-aminobutyric acid residue (to be also referred to as α-aminobutyric acid residue)
Orn: ornithine residue
Cit: citrulline residue The amino acid sequence of the "peptide" in the present invention is described according to the conventional method, wherein the amino acid residue of the N-terminal amino acid is positioned on the left side, and the amino acid residue of the C-terminal amino acid is positioned on the right side. In the "peptide", unless particularly indicated, the amino group of the amino acid residue of the N-terminal amino acid is bonded to hydrogen atom, and the carbonyl group of the amino acid residue of the C-terminal amino acid is bonded to hydroxyl group. The divalent group of peptide means a group bonding via the amino group of the amino acid residue of the N-terminal amino acid and the carbonyl group of the amino acid residue of the C-terminal amino acid.

In the compound of the present invention, for example, in the compounds represented by the formulae (3)-(9) and as regards peptide, which is a partial structure thereof, unless particularly indicated, the amino group of the amino acid residue of the N-terminal amino acid is bonded to hydrogen atom, and the carbonyl group of the amino acid residue of the C-terminal amino acid is bonded to hydroxyl group.

"$X^a$" and "$Y^a$" in the present invention mean, independently, a single bond or a divalent group of peptides consisting of 1-4 amino acid residues. The sum of the amino acid residue number of $X^a$ and that of $Y^a$ is an integer of 0-4. For example, an integer of said sum being 0 means that $X^a$ and $Y^a$ are each a single bond. When the sum is an integer of 4, examples thereof include $X^a$ and $Y^a$ independently being divalent groups of peptide consisting of 2 amino acid residues, $X^a$ being a divalent group of peptide consisting of 3 amino acid residues and $Y^a$ being a divalent group of peptide consisting of 1 amino acid residue, $X^a$ being a divalent group of peptide consisting of 4 amino acid residues and $Y^a$ being a single bond and the like.

The integer of said sum is preferably 0-2, more preferably 0-1, most preferably 0. That is, $X^a$ and $Y^a$ are most preferably single bonds.

When the sum is an integer of 2, examples thereof include $X^a$ being a divalent group of peptide consisting of 2 amino acid residues and $Y^a$ being a single bond, $X^a$ and $Y^a$ independently being divalent groups of peptide consisting of 1 amino acid residue, or $X^a$ being a single bond and $Y^a$ being a divalent group of peptide consisting of 2 amino acid residues.

When the sum is an integer of 1, examples thereof include $X^a$ being a divalent group of peptide consisting of 1 amino acid residue and $Y^a$ being a single bond, and $X^a$ being a single bond and $Y^a$ being a divalent group of peptide consisting of 1 amino acid residue. Of these, preferred is $X^a$ being a single bond and $Y^a$ being an alanine residue, leucine residues or methionine residue.

The "cancer antigen peptide A" in the present invention is an MHC class I-restricted WT1 peptide consisting of 7-30 amino acid residues. In cancer antigen peptide A in the formula (1), the amino group of the N-terminal amino acid is bonded to $Y^a$ in the formula (1) and the carbonyl group of the C-terminal amino acid is bonded to the hydroxyl group in the formula (1).

The "MHC class I-restricted" in the present invention means the property to induce CTL by binding to an MHC class I molecule which is class I of the major histocompatibility complex (MHC).

MHC in human is called human leukocyte-type antigen (HLA). HLA corresponding to the MHC class I-molecule is classified into subtypes of HLA-A, B, Cw, F and G and the like. Preferable examples of the "MHC class I-restricted" include HLA-A-restricted, HLA-B-restricted and HLA-Cw-restricted.

Polymorphism (allele) of each subtype of HLA is known. Examples of the polymorphism of HLA-A include not less than 27 kinds such as HLA-A1, HLA-A0201, HLA-A24 and the like, examples of the polymorphism of HLA-B include not less than 59 kinds such as HLA-B7, HLA-B40, HLA-B4403 and the like, and examples of the polymorphism of HLA-Cw include not less than 10 kinds such as HLA-Cw0301, HLA-Cw0401, HLA-Cw0602 and the like. Among these polymorphisms, HLA-A0201 and HLA-A24 are preferable.

The "WT1 peptide" in the present invention is a partial peptide consisting of continuous 7-30 amino acid residues in the amino acid sequence of human WT1 described in SEQ ID NO: 1.

Therefore, the "MHC class I-restricted WT1 peptide" in the present invention is a peptide that binds to an MHC class I antigen in vitro and/or in vivo and is presented as a complex, and induces CTL as a result of recognition of the complex by precursor T cells. The number of the amino acid residues of the "MHC class I-restricted WT1 peptide" is 7-30, preferably 7-15, more preferably 8-12, further preferably 8-11, most preferably 8 or 9.

The "MHC class I-restricted WT1 peptide" consisting of 7-12 or preferably 9 amino acid residues is also called "an MHC class I-restricted WT1 epitope". The "MHC class I-restricted WT1 epitope" in the present invention means a peptide per se that binds to an MHC class I antigen and is presented as a complex. That is, "MHC class I-restricted WT1 peptide" produces "MHC class I-restricted WT1 epitope" in vitro and/or in vivo, by intracellular decomposition of the compound of the present invention by proteosome and/or protease such as Gamma-Interferon-inducible Lysosomal Thiol Reductase (GILT, GLT) and the like (proteolysis, reductive cleavage of disulfide bond), and/or cleavage into the optimal residue number (also called trimming) by Endoplasmic reticulum aminopeptidase 1 (ERAP1, ER-aminopeptidase 1). In this production, a production process wherein the C-terminal amino acid of the "MHC class I-restricted WT1 epitope" first results from the degradation by proteosome and/or protease, after which N-terminal amino acid of the "MHC class I-restricted WT1 epitope" results from trimming (cleavage) by ERAP1 is mainly considered. In this production, however, a process other than this production process is also possible. At present, ERAP1 is also referred to as ERAAP (ER aminopeptidase associated with antigen presentation), and used to be also called A-LAP, PILS-AP or ARTS-1.

Therefore, the "MHC class I-restricted WT1 peptide" is preferably a peptide consisting of 7-30 amino acid residues produced by adding 1-23 amino acid residues to the carbonyl group of the C-terminal amino acid of the "MHC class I-restricted WT1 epitope" consisting of 7-12 amino acid residues.

Examples of the "MHC class I-restricted WT1 peptide" include peptides described in Tables 1-44. In each Table, the "position" means a position in the amino acid sequence of human WT1 described in SEQ ID NO: 1.

TABLE 1

| position | amino acid sequence | sequence No. | HLA subtype |
|---|---|---|---|
| 2-10 | GSDVRDLNA | 26 | A1 |
| 3-11 | SDVRDLNAL | 27 | B40, B60, B61, B3701, B4403, Cw0301, Cw0602 |
| 4-12 | DVRDLNALL | 28 | A24, A68.1, A3302, B7, B8, B3501, B3701, Cw0401, Cw0602 |
| 6-14 | RDLNALLPA | 29 | B40, B61, B3701 |
| 7-15 | DLNALLPAV | 30 | A0201, B62, B5201 |
| 10-18 | ALLPAVPSL | 5 | A0201, A0205, A24, A3, B14, B7, B8, B3801, B3901, B3902, Cw0301, Cw0401, Cw0602 |

TABLE 2

| position | amino acid sequence | sequence No. | HLA subtype |
|---|---|---|---|
| 17-25 | SLGGGGGCA | 31 | B62 |
| 18-26 | LGGGGGCAL | 32 | B60, B7, B3801, B5101, B5102 |
| 20-28 | GGGGCALPV | 33 | B61, B5101, B5102, B5201 |

TABLE 3

| position | amino acid sequence | sequence No. | HLA subtype |
|---|---|---|---|
| 23-31 | GCALPVSGA | 34 | B40, B61 |
| 24-32 | CALPVSGAA | 35 | B40, B5102, Cw0301 |
| 26-34 | LPVSGAAQW | 36 | B40, B3501, B5801 |
| 29-37 | SGAAQWAPV | 37 | B5101, B5102, B5201, B61 |
| 30-38 | GAAQWAPVL | 38 | B40, B60, B7, B8, B3902, B5101, B5102, Cw0301, Cw0602 |

TABLE 4

| position | amino acid sequence | sequence No. | HLA subtype |
|---|---|---|---|
| 32-40 | AQWAPVLDF | 39 | A3, A3101, B62, B2702, B2705, B3902, B5201 |

TABLE 4-continued

| position | amino acid sequence | sequence No. | HLA subtype |
|---|---|---|---|
| 33-41 | QWAPVLDFA | 40 | Cw0702 |
| 37-45 | VLDFAPPGA | 41 | A1, A0201 |
| 38-46 | LDFAPPGAS | 42 | B40, B3701 |
| 39-47 | DFAPPGASA | 43 | Cw0401 |
| 40-48 | FAPPGASAY | 44 | A1, B62, B3501, B4403, B5801, Cw0702 |

TABLE 5

| position | amino acid sequence | sequence No. | HLA subtype |
|---|---|---|---|
| 47-55 | AYGSLGGPA | 45 | A24 |

TABLE 6

| position | amino acid sequence | sequence No. | HLA subtype |
|---|---|---|---|
| 63-71 | PPPPPPHSF | 46 | Cw0401 |
| 64-72 | PPPPPHSFI | 47 | B5101, B5102, B5201 |
| 65-73 | PPPPHSFIK | 48 | A1101 |
| 70-78 | SFIKQEPSW | 49 | Cw0401 |

TABLE 7

| position | amino acid sequence | sequence No. | HLA subtype |
|---|---|---|---|
| 73-81 | KQEPSWGGA | 50 | A1, A0205 |
| 80-88 | GAEPHEEQC | 51 | A1 |

TABLE 8

| position | amino acid sequence | sequence No. | HLA subtype |
|---|---|---|---|
| 81-89 | AEPHEEQCL | 52 | A0205, B40, B60, B61, B3701, B4403 |
| 82-90 | EPHEEQCLS | 53 | B3501, B5101 |
| 83-91 | PHEEQCLSA | 54 | B3801 |
| 84-92 | HEEQCLSAF | 55 | B40, B3701, B4403, Cw0702 |
| 85-93 | EEQCLSAFT | 56 | B40, B60, B61, B3701, B4403 |
| 86-94 | EQCLSAFTV | 57 | A0201, B62, B5201 |
| 88-96 | CLSAFTVHF | 58 | A3, B62 |

TABLE 9

| position | amino acid sequence | sequence No. | HLA subtype |
|---|---|---|---|
| 92-100 | FTVHFSGQF | 59 | B62, B5801, Cw0301 |
| 93-101 | TVHFSGQFT | 60 | A0201, A0205 |
| 96-104 | FSGQFTGTA | 61 | B5801, B4403 |
| 98-106 | GQFTGTAGA | 62 | A0205, B40, B62, B2702, B5201 |
| 99-107 | QFTGTAGAC | 63 | Cw0401 |
| 100-108 | FTGTAGACR | 64 | A68.1, A1101, A3101, A3302 |

TABLE 10

| position | amino acid sequence | sequence No. | HLA subtype |
|---|---|---|---|
| 101-109 | TGTAGACRY | 65 | B62, B4403, Cw0702 |
| 104-112 | AGACRYGPF | 66 | B4403, B5201 |
| 107-115 | CRYGPFGPP | 67 | B2702 |
| 110-118 | GPFGPPPPS | 68 | B5101, B5102 |

TABLE 11

| position | amino acid sequence | sequence No. | HLA subtype |
|---|---|---|---|
| 118-126 | SQASSGQAR | 69 | A68.1, A1101, A3101, A3302 |
| 119-127 | QASSGQARM | 70 | B3501, B5101, B5102 |
| 120-128 | ASSGQARMF | 71 | B3501, B3801, B4403, B5801 |

TABLE 12

| position | amino acid sequence | sequence No. | HLA subtype |
|---|---|---|---|
| 123-131 | GQARMFPNA | 72 | B62 |
| 125-133 | ARMFPNAPY | 73 | B14, B2702, B2705, Cw0702 |
| 126-134 | RMFPNAPYL | 2 | A0201, A0205, A24, A3, B14, B7, B2702, B2705, B3901, B3902, Cw0301 |
| 128-136 | FPNAPYLPS | 74 | B5101 |
| 130-138 | NAPYLPSCL | 75 | A24, B60, B7, B8, B3902, B5101, B5102, Cw0301, Cw0602, Cw0702 |

TABLE 13

| position | amino acid sequence | sequence No. | HLA subtype |
|---|---|---|---|
| 136-144 | SCLESQPAI | 76 | B8, B3901, B5102, Cw0301 |
| 137-145 | CLESQPAIR | 77 | A1, A3, A68.1, A1101, A3101, A3302 |
| 138-146 | LESQPAIRN | 78 | B60, B61 |
| 139-147 | ESQPAIRNQ | 79 | A3302 |

TABLE 14

| position | amino acid sequence | sequence No. | HLA subtype |
|---|---|---|---|
| 141-149 | QPAIRNQGY | 80 | B8, B3501, B4403, Cw0401, Cw0702 |
| 143-151 | AIRNQGYST | 81 | B7 |
| 144-152 | IRNQGYSTV | 82 | B14, B2702, B2705, B3901 |
| 146-154 | NQGYSTVTF | 83 | B62, B2702, B3902, B5201 |

TABLE 15

| position | amino acid sequence | sequence No. | HLA subtype |
|---|---|---|---|
| 152-160 | VTFDGTPSY | 84 | A1, A3, B62, B3501, B4403, B5801, Cw0702 |

TABLE 16

| position | amino acid sequence | sequence No. | HLA subtype |
|---|---|---|---|
| 161-169 | GHTPSHHAA | 85 | B3801 |
| 163-171 | TPSHHAAQF | 86 | B3501, B3801, Cw0401, Cw0702 |
| 165-173 | SHHAAQFPN | 87 | B3801 |
| 168-176 | AAQFPNHSF | 88 | B5801 |
| 169-177 | AQFPNHSFK | 89 | A3, A68.1, A1101, A3101, B2705 |

TABLE 17

| position | amino acid sequence | sequence No. | HLA subtype |
|---|---|---|---|
| 174-182 | HSFKHEDPM | 90 | B14, B3501, B5801 |
| 177-185 | KHEDPMGQQ | 91 | B3801 |
| 179-187 | EDPMGQQGS | 92 | B3701 |
| 180-188 | DPMGQQGSL | 93 | A24, B14, B60, B7, B8, B3501, B3801, B3901, B3902, B5101, B5102, Cw0301, Cw0401, Cw0602 |

TABLE 18

| position | amino acid sequence | sequence No. | HLA subtype |
|---|---|---|---|
| 185-193 | QGSLGEQQY | 94 | B4403, Cw0702 |
| 187-195 | SLGEQQYSV | 6 | A0201, A0205, A3, B62 |

TABLE 19

| position | amino acid sequence | sequence No. | HLA subtype |
|---|---|---|---|
| 191-199 | QQYSVPPPV | 95 | A0201, A0205, B61, B62, B2702, B2705, B5201 |
| 192-200 | QYSVPPPVY | 96 | A24, Cw0401, Cw0702 |
| 194-202 | SVPPPVYGC | 97 | A0205, A3 |

TABLE 20

| position | amino acid sequence | sequence No. | HLA subtype |
|---|---|---|---|
| 202-210 | CHTPTDSCT | 98 | B3801 |
| 204-212 | TPTDSCTGS | 99 | B5101 |
| 206-214 | TDSCTGSQA | 100 | B40, B61, B3701 |
| 207-215 | DSCTGSQAL | 101 | A24, A3302, B60, B7, B8, B3501, B3901, B3902, Cw0602 |
| 208-216 | SCTGSQALL | 102 | B60, B7, B8, B3701, B3801, B3901, B3902 |
| 209-217 | CTGSQALLL | 103 | B60, B7, B3701, B3902 |
| 210-218 | TGSQALLLR | 104 | A3302 |

TABLE 21

| position | amino acid sequence | sequence No. | HLA subtype |
|---|---|---|---|
| 211-219 | GSQALLLRT | 105 | B5801 |
| 213-221 | QALLLRTPY | 106 | A1, B3501, B4403, B5801, Cw0602, Cw0702 |
| 217-225 | LRTPYSSDN | 107 | B2702 |
| 218-226 | RTPYSSDNL | 108 | A24, B60, B7, B3902, B5801 |
| 219-227 | TPYSSDNLY | 109 | B3501, B5101, B5102, Cw0401, Cw0702 |

TABLE 22

| position | amino acid sequence | sequence No. | HLA subtype |
|---|---|---|---|
| 221-229 | YSSDNLYQM | 110 | B60, B3501 |
| 222-230 | SSDNLYQMT | 111 | A1, B5801 |
| 223-231 | SDNLYQMTS | 112 | B3701 |
| 225-233 | NLYQMTSQL | 113 | A0201, A0205, A24, B14, B7, B8, B3801, B3901, B3902, Cw0301, Cw0602 |
| 227-235 | YQMTSQLEC | 114 | A0201, A0205, B62 |
| 228-236 | QMTSQLECM | 115 | A0201 |
| 230-238 | TSQLECMTW | 116 | B5801 |

TABLE 23

| position | amino acid sequence | sequence No. | HLA subtype |
|---|---|---|---|
| 232-240 | QLECMTWNQ | 117 | A1 |
| 233-241 | LECMTWNQM | 118 | B40, B60, B61, B3701, B4403 |
| 235-243 | CMTWNQMNL | 3 | A0201, A0205, A24, A3, B7 |
| 239-247 | NQMNLGATL | 119 | A0201, A0205, A24, B14, B60, B62, B7, B2702, B2705, B3901, B3902, B5201, Cw0301, Cw0602 |
| 240-248 | QMNLGATLK | 120 | A24, A3, A1101, A3101 |

TABLE 24

| position | amino acid sequence | sequence No. | HLA subtype |
|---|---|---|---|
| 242-250 | NLGATLKGV | 121 | A0201, A0205, B62, Cw0602 |

TABLE 24-continued

| position | amino acid sequence | sequence No. | HLA subtype |
|---|---|---|---|
| 243-251 | LGATLKGVA | 122 | B5201 |
| 244-252 | GATLKGVAA | 123 | B61, B8 |
| 250-258 | VAAGSSSSV | 124 | B61, B5101, B5102 |

TABLE 25

| position | amino acid sequence | sequence No. | HLA subtype |
|---|---|---|---|
| 251-259 | AAGSSSSVK | 125 | A68.1, A1101 |
| 252-260 | AGSSSSVKW | 126 | B5801 |
| 260-268 | WTEGQSNHS | 127 | A1 |

TABLE 26

| position | amino acid sequence | sequence No. | HLA subtype |
|---|---|---|---|
| 261-269 | TEGQSNHST | 128 | B40, B60, B61, B4403 |
| 263-271 | GQSNHSTGY | 129 | A3, B62, B2702, Cw0702 |
| 269-277 | TGYESDNHT | 130 | B5102, B5201 |
| 270-278 | GYESDNHTT | 131 | A24 |

TABLE 27

| position | amino acid sequence | sequence No. | HLA subtype |
|---|---|---|---|
| 272-280 | ESDNHTTPI | 132 | A1, A3302, B5101 |
| 273-281 | SDNHTTPIL | 133 | B40, B60, B3701, B5201 |
| 276-284 | HTTPILCGA | 134 | B5801 |
| 278-286 | TPILCGAQY | 135 | B3501, B4403, Cw0401, Cw0702 |
| 279-287 | PILCGAQYR | 136 | A3101 |
| 280-288 | ILCGAQYRI | 137 | A0201, A0205, A3, B62, B5101 |

TABLE 28

| position | amino acid sequence | sequence No. | HLA subtype |
|---|---|---|---|
| 285-293 | QYRIHTHGV | 138 | A24, Cw0401 |
| 286-294 | YRIHTHGVF | 139 | B14, B2702, B2705, B5201, Cw0301 |
| 287-295 | RIHTHGVFR | 140 | A3, A1101, A3101, A3302 |
| 289-297 | HTHGVFRGI | 141 | B5801 |

TABLE 29

| position | amino acid sequence | sequence No. | HLA subtype |
|---|---|---|---|
| 292-300 | GVFRGIQDV | 142 | A0201, A0205, A3, A68.1, A1101, B3901, B5102, B5201, Cw0602 |
| 293-301 | VFRGIQDVR | 143 | A3101 |
| 294-302 | FRGIQDVRR | 144 | B2705 |
| 295-303 | RGIQDVRRV | 145 | B61, B5101, B5102, B5201, Cw0602 |
| 298-306 | QDVRRVPGV | 146 | B61, B3701 |
| 299-307 | DVRRVPGVA | 147 | A68.1, A3302, B7, B8 |

TABLE 30

| position | amino acid sequence | sequence No. | HLA subtype |
|---|---|---|---|
| 301-309 | RRVPGVAPT | 148 | B14, B2702, B2705, Cw0301 |
| 302-310 | RVPGVAPTL | 7 | A0205, A24, B7, B3701, B3801, B3901, B3902 |
| 303-311 | VPGVAPTLV | 149 | B7, B3501, B5102, B5201, Cw0401 |
| 306-314 | VAPTLVRSA | 150 | B4403 |
| 309-317 | TLVRSASET | 151 | A0201, A0205 |

TABLE 31

| position | amino acid sequence | sequence No. | HLA subtype |
|---|---|---|---|
| 312-320 | RSASETSEK | 152 | A68.1, A1101 |
| 313-321 | SASETSEKR | 153 | A3101, A3302 |
| 315-323 | SETSEKRPF | 154 | B40, B3701, B4403 |
| 316-324 | ETSEKRPFM | 155 | B8, B3501 |
| 317-325 | TSEKRPFMC | 156 | A1, B5801 |
| 318-326 | SEKRPFMCA | 157 | B40, B60, B61, B4403 |
| 319-327 | EKRPFMCAY | 158 | Cw0602, Cw0702 |

TABLE 32

| position | amino acid sequence | sequence No. | HLA subtype |
|---|---|---|---|
| 324-332 | MCAYPGCNK | 159 | A68.1, A1101 |
| 325-333 | CAYPGCNKR | 160 | A1, A68.1, A1101, A3101, A3302 |
| 326-334 | AYPGCNKRY | 161 | A24, Cw0401, Cw0702 |
| 327-335 | YPGCNKRYF | 162 | B3501, B3801, B5201, Cw0401, Cw0702 |
| 329-337 | GCNKRYFKL | 163 | A24, B14, B60, B7, B8, B3902, Cw0301 |

TABLE 33

| position | amino acid sequence | sequence No. | HLA subtype |
|---|---|---|---|
| 332-340 | KRYFKLSHL | 164 | B14, B8, B2702, B2705, B3901, B3902, Cw0301, Cw0602 |
| 334-342 | YFKLSHLQM | 165 | Cw0401 |
| 337-345 | LSHLQMHSR | 166 | A68.1, A3302 |
| 340-348 | LQMHSRKHT | 167 | A0201, A0205 |

TABLE 34

| position | amino acid sequence | sequence No. | HLA subtype |
|---|---|---|---|
| 343-351 | HSRKHTGEK | 168 | A68.1 |
| 345-353 | RKHTGEKPY | 169 | Cw0702 |
| 347-355 | HTGEKPYQC | 170 | B8, B5801 |
| 349-357 | GEKPYQCDF | 171 | B40, B3701, B4403 |

TABLE 35

| position | amino acid sequence | sequence No. | HLA subtype |
|---|---|---|---|
| 351-359 | KPYQCDFKD | 172 | B5102 |
| 354-362 | QCDFKDCER | 173 | A1, A68.1, A3101, A3302 |
| 356-364 | DFKDCERRF | 174 | A24, Cw0401 |
| 358-366 | KDCERRFSR | 175 | A3101 |

TABLE 36

| position | amino acid sequence | sequence No. | HLA subtype |
|---|---|---|---|
| 362-370 | RRFSRSDQL | 176 | B2702, B2705, B3901, Cw0301, Cw0602 |

TABLE 36-continued

| position | amino acid sequence | sequence No. | HLA subtype |
|---|---|---|---|
| 363-371 | RFSRSDQLK | 177 | A1101 |
| 364-372 | FSRSDQLKR | 178 | A68.1, A3302 |
| 366-374 | RSDQLKRHQ | 179 | A1 |
| 368-376 | DQLKRHQRR | 180 | A68.1, A3101, A3302 |

TABLE 37

| position | amino acid sequence | sequence No. | HLA subtype |
|---|---|---|---|
| 371-379 | KRHQRRHTG | 181 | B14 |
| 372-380 | RHQRRHTGV | 182 | B14, B3801, B3901 |
| 373-381 | HQRRHTGVK | 183 | A1101, A3101, B2705 |
| 375-383 | RRHTGVKPF | 184 | B2702, B2705, Cw0702 |
| 379-387 | GVKPFQCKT | 185 | A68.1 |

TABLE 38

| position | amino acid sequence | sequence No. | HLA subtype |
|---|---|---|---|
| 383-391 | FQCKTCQRK | 186 | A3, A1101, A3101, B2705 |
| 384-392 | QCKTCQRKF | 187 | B62, B8 |
| 386-394 | KTCQRKFSR | 188 | A1, A3, A68.1, A1101, A3101 |
| 387-395 | TCQRKFSRS | 189 | B8 |
| 389-397 | QRKFSRSDH | 190 | B2702, B2705 |
| 390-398 | RKFSRSDHL | 191 | B14, B3901, B3902, Cw0301 |

TABLE 39

| position | amino acid sequence | sequence No. | HLA subtype |
|---|---|---|---|
| 391-399 | KFSRSDHLK | 192 | A1101, A3101 |
| 394-402 | RSDHLKTHT | 193 | A1, B5801 |
| 396-404 | DHLKTHTRT | 194 | B3801, B3901 |

TABLE 40

| position | amino acid sequence | sequence No. | HLA subtype |
|---|---|---|---|
| 401-409 | HTRTHTGKT | 195 | B8 |
| 406-414 | TGKTSEKPF | 196 | B5201 |

TABLE 40-continued

| position | amino acid sequence | sequence No. | HLA subtype |
|---|---|---|---|
| 408-416 | KTSEKPFSC | 197 | A0201, B5801 |
| 409-417 | TSEKPFSCR | 198 | A1, A68.1, A3302 |
| 410-418 | SEKPFSCRW | 199 | B40, B4403 |

TABLE 41

| position | amino acid sequence | sequence No. | HLA subtype |
|---|---|---|---|
| 412-420 | KPFSCRWPS | 200 | B3501, B5102 |
| 415-423 | SCRWPSCQK | 201 | A1101 |
| 416-424 | CRWPSCQKK | 202 | B2702, B2705 |
| 417-425 | RWPSCQKKF | 203 | A24, B3801, Cw0401 |
| 418-426 | WPSCQKKFA | 204 | B5102 |
| 419-427 | PSCQKKFAR | 205 | A3302 |
| 420-428 | SCQKKFARS | 206 | B8 |

TABLE 42

| position | amino acid sequence | sequence No. | HLA subtype |
|---|---|---|---|
| 423-431 | KKFARSDEL | 207 | B14, B3901, B3902, Cw0301, Cw0602 |
| 424-432 | KFARSDELV | 208 | Cw0401 |
| 425-433 | FARSDELVR | 209 | A68.1, A1101, A3101, A3302 |
| 426-434 | ARSDELVRH | 210 | B2702, B2705 |
| 427-435 | RSDELVRHH | 211 | A1 |
| 428-436 | SDELVRHHN | 212 | B3701 |
| 429-437 | DELVRHHNM | 213 | B14, B40, B60, B61, B3701, B4403, Cw0301 |

TABLE 43

| position | amino acid sequence | sequence No. | HLA subtype |
|---|---|---|---|
| 432-440 | VRHHNMHQR | 214 | B2705 |
| 433-441 | RHHNMHQRN | 215 | B3801 |
| 434-442 | HHNMHQRNM | 216 | B3901 |
| 436-444 | NMHQRNMTK | 217 | A3, A1101, A3101 |
| 437-445 | MHQRNMTKL | 218 | B14, B3701, B3901, B3902, Cw0301 |

TABLE 43-continued

| position | amino acid sequence | sequence No. | HLA subtype |
|---|---|---|---|
| 439-447 | QRNMTKLQL | 220 | B14, B2702, B2705, B3901, Cw0602 |
| 440-448 | RNMTKLQLA | 221 | B61 |

TABLE 44

| position | amino acid sequence | sequence No. | HLA subtype |
|---|---|---|---|
| 441-449 | NMTKLQLAL | 222 | A0201, A0205, A24, A3, B7, B3902, Cw0602 |

Preferable examples of the "MHC class I-restricted WT1 peptide" include a peptide comprising any amino acid sequence selected from the following amino acid sequences:

```
RMFPNAPYL,      (SEQ ID NO: 2)

CMTWNQMNL,      (SEQ ID NO: 3)

ALLPAVPSL,      (SEQ ID NO: 5)

SLGEQQYSV       (SEQ ID NO: 6)
and

RVPGVAPTL,      (SEQ ID NO: 7)
``` and
a peptide comprising an altered amino acid sequence, which is any amino acid sequence selected from SEQ ID NOs: 2, 3, 5, 6 and 7 but containing alteration of amino acid residue(s), and having a CTL induction activity, more preferably a peptide of any of the amino acid sequences selected from SEQ ID NOs: 2, 3, 5, 6 and 7.

The "peptide comprising an amino acid sequence" in the present invention means, as usual, a peptide wherein a further amino acid is added to the N-terminal amino acid and/or C-terminal amino acid of the amino acid sequence. When the "MHC class I-restricted WT1 peptide" in the "cancer antigen peptide A" and "cancer antigen peptide B" is added, a peptide with addition to the C-terminal side is preferable. When the "MHC class I-restricted WT1 epitope" is added, addition to the C-terminal side is preferable.

The "peptide comprising an altered amino acid sequence that contains alteration of amino acid residue(s) in the amino acid sequence, and having a CTL induction activity" in the present invention is also called an "altered killer peptide". The altered killer peptide means a peptide that consists of an amino acid sequence wherein 1 to 3 amino acids are deleted, substituted and/or added and binds to MHC class I to induce CTL. The substitution position of the substituted amino acid includes the 1st-position (N-terminal), the 2nd-position, the 3rd-position or the 9th-position for a peptide consisting of 9 amino acid residues. The number of the amino acids to be added (also including insertion) is preferably 1 or 2, more preferably 1. A preferable addition position is the C-terminal. The number of the amino acids to be deleted is preferably 1. In the alteration, the amino acid to be added or amino acid to be substituted may be a non-natural amino acid other than the 20 kinds of amino acids encoded by the gene.

It is known that the amino acid sequence of a peptide bindable to HLA antigen has regularity (binding motif) for each polymorphism of HLA subtype. For example, as a binding motif of HLA-A24, a peptide consisting of 8-11 amino acid residues, wherein the 2nd-position amino acid is Tyr, Phe, Met or Trp, and the C-terminal amino acid is Phe, Leu, Ile, Trp or Met, is known (J. Immunol., 152, p 3913, 1994, J. Immunol., 155, p 4307, 1994, Immunogenetics, 41, p 178, 1995). Therefore, for example, in the case of a peptide consisting of 9 amino acid residues, the 2nd-position can be substituted by Tyr, Phe, Met or Trp and/or the 9th-position can be substituted by Phe, Leu, Ile, Trp or Met, and a peptide having such substitutions is preferable as an altered killer peptide. Similarly, a peptide consisting of 8-11 amino acid residues, wherein the 2nd-position amino acid is Leu or Met and the C-terminal amino acid is Val or Leu, is known as a binding motif of HLA-A0201. Therefore, for example, in the case of a peptide consisting of 9 amino acid residues, the 2nd-position can be substituted by Leu or Met and/or the 9th-position can be substituted by Val or Leu, and a peptide having such substitutions is preferable as an altered killer peptide.

Examples of the altered killer peptide include the following peptides.

```
RYFPNAPYL           (SEQ ID NO: 223)
(see WO03/106682),

FMFPNAPYL,          (SEQ ID NO: 224)

RLFPNAPYL,          (SEQ ID NO: 225)

RMMPNAPYL,          (SEQ ID NO: 226)

RMFPNAPYV           (SEQ ID NO: 227)
and

YMFPNAPYL           (SEQ ID NO: 228)
(see WO2009/072610),
``` which are altered killer peptides of RMFPNAPYL (SEQ ID NO: 2);
CYTWNQMNL (SEQ ID NO: 4) (see WO02/79253); Xaa-Met-Thr-Trp-Asn-Gln-Met-Asn-Leu (SEQ ID NO: 229) (wherein Xaa is Ser or Ala) and Xaa-Tyr-Thr-Trp-Asn-Gln-Met-Asn-Leu (SEQ ID NO: 230) (wherein Xaa is Ser, Ala, Abu, Arg, Lys, Orn, Cit, Leu, Phe or Asn) (see WO2004/026897), which are altered killer peptides of CMTWNQMNL (SEQ ID NO: 3);
AYLPAVPSL (SEQ ID NO: 231) (see WO2003/106682), which is an altered killer peptide of ALLPAVPSL (SEQ ID NO: 5);
FLGEQQYSV (SEQ ID NO: 232),
SMGEQQYSV (SEQ ID NO: 233) and
SLMEQQYSV (SEQ ID NO: 234) (WO2009/072610), which are altered killer peptides of SLGEQQYSV (SEQ ID NO: 6); and
RYPGVAPTL (SEQ ID NO: 235) (WO2003/106682), which is an altered killer peptide of RVPGVAPTL (SEQ ID NO: 7).

"$R^1$" in the present invention is a hydrogen atom, a group represented by the aforementioned formula (2) or cancer antigen peptide C, preferably a group represented by the aforementioned formula (2) or cancer antigen peptide C.

When $R^1$ is a hydrogen atom, the compound of the formula (1) is a compound represented by the formula (1-1):

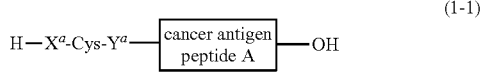

(1-1)

wherein $X^a$, $Y^a$ and cancer antigen peptide A are as defined in the above for the formula (1), and Cys is a cysteine residue, namely, a peptide.

The compound of the formula (1), wherein $R^1$ is a hydrogen atom, namely, a peptide represented by the formula (1-1), has a sequence different from a partial sequence of WT1 protein. The requirement of the formula (1), "has a sequence different from a partial sequence of WT1 protein" means that a peptide represented by the formula (1-1) is not a partial peptide consisting of continuous 8-35 amino acid residues in the amino acid sequence of human WT1 described in SEQ ID NO: 1.

That is, the compound of the formula (1), wherein $R^1$ is a hydrogen atom, is not a partial peptide consisting of continuous 8-35 amino acid residues in the amino acid sequence of human WT1 described in SEQ ID NO: 1. A specific explanation is given by taking a case when the cancer antigen peptide A is a $WT1_{138-146}$ peptide as an example. $WT1_{138-146}$ peptide is a partial peptide consisting of continuous 9 amino acid residues at the 138th-position-146th-position of the amino acid sequence of human WT1 described in SEQ ID NO: 1, and has an amino acid sequence of LESQPAIRN (SEQ ID NO: 78). In SEQ ID NO: 1, the 137th-position continuing from the N-terminal side of $WT1_{138-146}$ peptide is C. Therefore, $WT1_{137-146}$ peptide (CLESQPAIRN) (SEQ ID NO: 236) corresponds to a partial peptide consisting of continuous 10 amino acid residues of the amino acid sequence of human WT1 described in SEQ ID NO: 1. On the other hand, based on the requirement of the present invention, "the compound of the formula (1), wherein $R^1$ is a hydrogen atom, is not a partial peptide consisting of continuous 8-35 amino acid residues in the amino acid sequence of human WT1 described in SEQ ID NO: 1", in the compound of the formula (1) wherein $R^1$ is a hydrogen atom, when the cancer antigen peptide A is $WT1_{138-146}$ peptide (LESQPAIRN) (SEQ ID NO: 78), $WT1_{137-146}$ peptide (CLESQPAIRN) (SEQ ID NO: 236) is excluded from the compound of the present invention, and therefore, $X^a$ and $Y^a$ are not simultaneously a single bond.

As a compound of the formula (1) wherein $R^1$ is a hydrogen atom, a peptide consisting of any amino acid sequence selected from the following amino acid sequences:

```
CRMFPNAPYL,         (SEQ ID NO: 13)

CCMTWNQMNL,         (SEQ ID NO: 14)

CCYTWNQMNL,         (SEQ ID NO: 15)

CALLPAVPSL,         (SEQ ID NO: 16)

CSLGEQQYSV          (SEQ ID NO: 17)
and

CRVPGVAPTL          (SEQ ID NO: 18)
``` is preferable.

When "$R^1$" is a group represented by the aforementioned formula (2), a compound of the formula (1) is a compound represented by the formula (1-2):

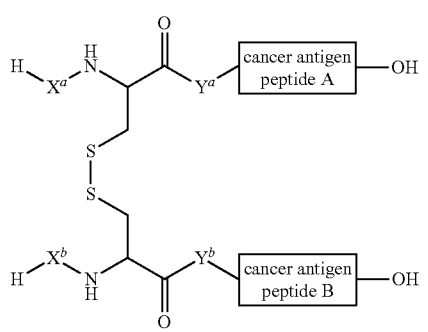

(1-2)

wherein $X^a$, $Y^a$ and cancer antigen peptide A are as defined in the above for the formula (1), and $X^b$, $Y^b$ and cancer antigen peptide B are as defined in the above for the formula (2).

"$X^b$" and "$Y^b$" in the present invention mean, independently, a single bond or a divalent group of peptides consisting of 1-4 amino acid residues. The sum of the amino acid residue number of $X^b$ and that of $Y^b$ is an integer of 0-4. For example, an integer of said sum being 0 means that $X^b$ and $Y^b$ are each a single bond. When the sum is an integer of 4, examples thereof include $X^b$ and $Y^b$ independently being divalent groups of peptide consisting of 2 amino acid residues, $X^b$ being a divalent group of peptide consisting of 3 amino acid residues and $Y^b$ being a divalent group of peptide consisting of 1 amino acid residue, $X^b$ being a divalent group of peptide consisting of 4 amino acid residues and $Y^b$ being a single bond and the like.

The integer of said sum is preferably 0-2, more preferably 0-1, most preferably 0. That is, $X^b$ and $Y^b$ are most preferably single bonds.

When the sum is an integer of 2, examples thereof include $X^b$ being a divalent group of peptide consisting of 2 amino acid residues and $Y^b$ being a single bond, $X^b$ and $Y^b$ independently being divalent groups of peptide consisting of 1 amino acid residue, and $X^b$ being a single bond and $Y^b$ being a divalent group of peptide consisting of 2 amino acid residues.

When the sum is an integer of 1, examples thereof include $X^b$ being a divalent group of peptide consisting of 1 amino acid residue and $Y^b$ being a single bond, and $X^b$ being a single bond and $Y^b$ being a divalent group of peptide consisting of 1 amino acid residue. Of these, preferred is $X^b$ being a single bond and $Y^b$ being an alanine residue, leucine residues or methionine residue.

The "cancer antigen peptide B" in the present invention is an MHC class I-restricted WT1 peptide consisting of 7-30 amino acid residues. The "MHC class I-restricted WT1 peptide" is as defined above. However, in the compound represented by the formula (1), cancer antigen peptide A and cancer antigen peptide B are not simultaneously the same peptide. That is, cancer antigen peptide B is limited by the requirement, "different from cancer antigen peptide A".

Since cancer antigen peptide A and cancer antigen peptide B are not simultaneously the same peptide, the compound of the formula (1), wherein $R^1$ is a group represented by the aforementioned formula (2), is not a homodimer but a heterodimer, even when $X^a$ and $X^b$ are the same and $Y^a$ and $Y^b$ are the same. Homodimer means a dimer wherein the same peptide monomers are dimerized, and heterodimer means a dimer wherein different peptide monomers are dimerized.

In cancer antigen peptide B, the amino group of the N-terminal amino acid is bonded to $Y^b$ in the formula (2) (i.e., also bonded to $Y^b$ in the formula (1-2)), and the carbonyl group of the C-terminal amino acid is bonded to the hydroxyl group in the formula (2).

As a compound of the formula (1) wherein $R^1$ is a group represented by the formula (2), i.e., a compound of the formula (1-2), a compound represented by the formula (3):

$$\text{CRMFPNAPYL} \atop | \atop \text{CSLGEQQYSV} \tag{3}$$

wherein the bond between C and C is a disulfide bond, is preferable.

In the present invention, moreover, when the "cancer antigen peptide B" is an MHC class I-restricted WT1 peptide containing one cysteine residue, the compound of the formula (1) may be a compound wherein the thioether group in the cancer antigen peptide B is bonded to a thioether group in the formula (16):

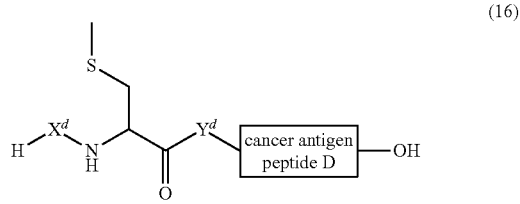

(16)

or to a thioether group of the cysteine residue of the cancer antigen peptide E.

"$X^d$" and "$Y^d$" in the present invention mean, independently, a single bond or a divalent group of peptides consisting of 1-4 amino acid residues. The sum of the amino acid residue number of $X^d$ and that of $Y^d$ is an integer of 0-4. For example, an integer of said sum being 0 means that $X^d$ and $Y^d$ are each a single bond. When the sum is an integer of 4, examples thereof include $X^d$ and $Y^d$ independently being divalent groups of peptide consisting of 2 amino acid residues, $X^d$ being a divalent group of peptide consisting of 3 amino acid residues and $Y^d$ being a divalent group of peptide consisting of 1 amino acid residue, $X^d$ being a divalent group of peptide consisting of 4 amino acid residues and $Y^d$ being a single bond and the like.

The integer of said sum is preferably 0-2, more preferably 0-1, most preferably 0. That is, $X^d$ and $Y^d$ are most preferably single bonds.

When the sum is an integer of 2, examples thereof include $X^d$ being a divalent group of peptide consisting of 2 amino acid residues and $Y^b$ being a single bond, $X^d$ and $Y^d$ independently being divalent groups of peptide consisting of 1 amino acid residue, or $X^d$ being a single bond and $Y^d$ being a divalent group of peptide consisting of 2 amino acid residues.

When the sum is an integer of 1, examples thereof include $X^d$ being a divalent group of peptide consisting of 1 amino acid residue and $Y^d$ being a single bond, and $X^d$ being a single bond and $Y^d$ being a divalent group of peptide consisting of 1 amino acid residue. Of these, preferred is $X^d$ being a single bond and $Y^d$ being an alanine residue, leucine residues or methionine residue.

The "cancer antigen peptide D" in the present invention is an MHC class II-restricted WT1 peptide consisting of 7-30 amino acid residues. In the formula (16), an amino group of the N-terminal amino acid of the cancer antigen peptide D binds to $Y^d$ in the formula (16), and a carbonyl group of the C-terminal amino acid binds to a hydroxyl group in the formula (16).

In the present invention, "MHC class II-restricted" means the property to induce helper T cell by binding to an MHC class II molecule, and is as defined for the below-mentioned "cancer antigen peptide C".

HLA corresponding to the MHC class II-molecule is classified into subtypes of HLA-DR, DQ and DP and the like. Preferable examples of the "MHC class II-restricted" include HLA-DR-restricted, HLA-DQ-restricted and HLA-DP-restricted.

Therefore, the "MHC class II-restricted WT1 peptide" in the present invention is a peptide that binds to an MHC class II antigen in vitro and/or in vivo and induces helper T cells.

The number of the amino acid residues of the "MHC class II-restricted WT1 peptide" is 7-30, preferably 14-30.

As the "cancer antigen peptide D", like the amino acid sequence recited in the below-mentioned "cancer antigen peptide C", a peptide consisting of any amino acid sequence selected from the following amino acid sequences:

```
SGQARMFPNAPYLPSC,           (SEQ ID NO: 19)
SGQAYMFPNAPYLPSC,           (SEQ ID NO: 25)
SGQAYMFPNAPYLPSCLES,        (SEQ ID NO: 11)
SGQAYMFPNAPYLPSCLES,        (SEQ ID NO: 12)
PGCNKRYFKLSHLQMHSRK,        (SEQ ID NO: 20)
PGCNKRYFKLSHLQMHSRKH,       (SEQ ID NO: 21)
PGCNKRYFKLSHLQMHSRKHTG,     (SEQ ID NO: 10)
CNKRYFKLSHLQMHSRK,          (SEQ ID NO: 22)
CNKRYFKLSHLQMHSRKH,         (SEQ ID NO: 23)
CNKRYFKLSHLQMHSRKHTG        (SEQ ID NO: 24)
and
WAPVLDFAPPGASAYGSL          (SEQ ID NO: 244)
``` can be mentioned.

In the compound of the formula (1), moreover, when the "cancer antigen peptide B" is an MHC class I-restricted WT1 peptide containing one cysteine residue, as a compound wherein the thioether group in the cancer antigen peptide B is bonded to a thioether group in the formula (16), preferably, a compound represented by the formula (15):

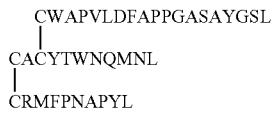

(15)

wherein the bond between C and C is a disulfide bond, can be mentioned.

In the present invention, the "cancer antigen peptide E" is an MHC class II-restricted WT1 peptide consisting of 7-30 amino acid residues containing one cysteine residue, and is as defined for the "MHC class II-restricted WT1 peptide consisting of 7-30 amino acid residues containing one cysteine residue" in the below-mentioned "cancer antigen peptide C". As the "cancer antigen peptide E", like the amino acid sequence recited in the below-mentioned "cancer antigen peptide C", a peptide consisting of any amino acid sequence selected from the following amino acid sequences:

```
SGQARMFPNAPYLPSC,           (SEQ ID NO: 19)
SGQAYMFPNAPYLPSC,           (SEQ ID NO: 25)
SGQARMFPNAPYLPSCLES,        (SEQ ID NO: 11)
SGQAYMFPNAPYLPSCLES,        (SEQ ID NO: 12)
PGCNKRYFKLSHLQMHSRK,        (SEQ ID NO: 20)
PGCNKRYFKLSHLQMHSRKH,       (SEQ ID NO: 21)
PGCNKRYFKLSHLQMHSRKHTG,     (SEQ ID NO: 10)
CNKRYFKLSHLQMHSRK,          (SEQ ID NO: 22)
CNKRYFKLSHLQMHSRKH          (SEQ ID NO: 23)
and
CNKRYFKLSHLQMHSRKHTG        (SEQ ID NO: 24)
``` can be mentioned.

When $R^1$ is cancer antigen peptide C, the thioether group of the cysteine residue of cancer antigen peptide C is bonded to the thioether group in the formula (1).

The cancer antigen peptide C is an MHC class I-restricted WT1 peptide consisting of 7-30 amino acid residues containing one cysteine residue or an MHC class II-restricted WT1 peptide consisting of 7-30 amino acid residues containing one cysteine residue.

In the "MHC class I-restricted WT1 peptide consisting of 7-30 amino acid residues containing one cysteine residue" in the present invention, the amino acid sequence of the peptide only needs to contain at least one cysteine residue. The number of the cysteine residues to be contained is preferably 1-3, more preferably 1-2, most preferably 1. The "MHC class I-restricted WT1 peptide" is as defined above. Also, the compound of the formula (1) wherein $R^1$ is "an MHC class I-restricted WT1 peptide consisting of 7-30 amino acid residues containing one cysteine residue" is not a homodimer but a heterodimer.

Preferable examples of the "MHC class I-restricted WT1 peptide consisting of 7-30 amino acid residues containing one cysteine residue" include peptides described in Tables 45-52. In each Table, the "position" means the position in the amino acid sequence of human WT1 described in SEQ ID NO: 1.

TABLE 45

| position | amino acid sequence | sequence No. | HLA subtype |
|---|---|---|---|
| 17-25 | SLGGGGGCA | 31 | B62 |
| 18-26 | LGGGGGCAL | 32 | B60, B7, B3801, B5101, B5102 |
| 20-28 | GGGGCALPV | 33 | B61, B5101, B5102, B5201 |
| 23-31 | GCALPVSGA | 34 | B40, B61 |
| 24-32 | CALPVSGAA | 35 | B40, B5102, Cw0301 |

TABLE 46

| position | amino acid sequence | sequence No. | HLA subtype |
|---|---|---|---|
| 80-88 | GAEPHEEQC | 51 | A1 |
| 81-89 | AEPHEEQCL | 52 | A0205, B40, B60, B61, B3701, B4403 |
| 82-90 | EPHEEQCLS | 53 | B3501, B5101 |
| 83-91 | PHEEQCLSA | 54 | B3801 |
| 84-92 | HEEQCLSAF | 55 | B40, B3701, B4403, Cw0702 |

TABLE 46-continued

| position | amino acid sequence | sequence No. | HLA subtype |
|---|---|---|---|
| 85-93 | EEQCLSAFT | 56 | B40, B60, B61, B3701, B4403 |
| 86-94 | EQCLSAFTV | 57 | A0201, B62, B5201 |
| 88-96 | CLSAFTVHF | 58 | A3, B62 |
| 99-107 | QFTGTAGAC | 63 | Cw0401 |
| 100-108 | FTGTAGACR | 64 | A68.1, A1101, A3101, A3302 |

TABLE 47

| position | amino acid sequence | sequence No. | HLA subtype |
|---|---|---|---|
| 101-109 | TGTAGACRY | 65 | B62, B4403, Cw0702 |
| 104-112 | AGACRYGPF | 66 | B4403, B5201 |
| 107-115 | CRYGPFGPP | 67 | B2702 |
| 130-138 | NAPYLPSCL | 75 | A24, B60, B7, B8, B3902, B5101, B5102, Cw0301, Cw0602, Cw0702 |
| 136-144 | SCLESQPAI | 76 | B8, B3901, B5102, Cw0301 |
| 137-145 | CLESQPAIR | 77 | A1, A3, A68.1, A1101, A3101, A3302 |
| 194-202 | SVPPPVYGC | 97 | A0205, A3 |

TABLE 48

| position | amino acid sequence | sequence No. | HLA subtype |
|---|---|---|---|
| 202-210 | CHTPTDSCT | 98 | B3801 |
| 204-212 | TPTDSCTGS | 99 | B5101 |
| 206-214 | TDSCTGSQA | 100 | B40, B61, B3701 |
| 207-215 | DSCTGSQAL | 101 | A24, A3302, B60, B7, B8, B3501, B3901, B3902, Cw0602 |
| 208-216 | SCTGSQALL | 102 | B60, B7, B8, B3701, B3801, B3901, B3902 |
| 209-217 | CTGSQALLL | 103 | B60, B7, B3701, B3902 |
| 227-235 | YQMTSQLEC | 114 | A0201, A0205, B62 |
| 228-236 | QMTSQLECM | 115 | A0201 |

TABLE 49

| position | amino acid sequence | sequence No. | HLA subtype |
|---|---|---|---|
| 230-238 | TSQLECMTW | 116 | B5801 |
| 232-240 | QLECMTWNQ | 117 | A1 |
| 233-241 | LECMTWNQM | 118 | B40, B60, B61, B3701, B4403 |
| 235-243 | CMTWNQMNL | 3 | A0201, A0205, A24, A3, B7 |
| 276-284 | HTTPILCGA | 134 | B5801 |
| 278-286 | TPILCGAQY | 135 | B3501, B4403, Cw0401, Cw0702 |
| 279-287 | PILCGAQYR | 136 | A3101 |
| 280-288 | ILCGAQYRI | 137 | A0201, A0205, A3, B62, B5101 |

TABLE 50

| position | amino acid sequence | sequence No. | HLA subtype |
|---|---|---|---|
| 317-325 | TSEKRPFMC | 156 | A1, B5801 |
| 318-326 | SEKRPFMCA | 157 | B40, B60, B61, B4403 |
| 319-327 | EKRPFMCAY | 158 | Cw0602, Cw0702 |
| 324-332 | MCAYPGCNK | 159 | A68.1, A1101 |
| 325-333 | CAYPGCNKR | 160 | A1, A68.1, A1101, A3101, A3302 |
| 326-334 | AYPGCNKRY | 161 | A24, Cw0401, Cw0702 |
| 327-335 | YPGCNKRYF | 162 | B3501, B3801, B5201, Cw0401, Cw0702 |
| 329-337 | GCNKRYFKL | 163 | A24, B14, B60, B7, B8, B3902, Cw0301 |
| 347-355 | HTGEKPYQC | 170 | B8, B5801 |
| 349-357 | GEKPYQCDF | 171 | B40, B3701, B4403 |

TABLE 51

| position | amino acid sequence | sequence No. | HLA subtype |
|---|---|---|---|
| 351-359 | KPYQCDFKD | 172 | B5102 |
| 354-362 | QCDFKDCER | 173 | A1, A68.1, A3101, A3302 |
| 356-364 | DFKDCERRF | 174 | A24, Cw0401 |
| 358-366 | KDCERRFSR | 175 | A3101 |
| 379-387 | GVKPFQCKT | 185 | A68.1 |
| 383-391 | FQCKTCQRK | 186 | A3, A1101, A3101, B2705 |

TABLE 51-continued

| position | amino acid sequence | sequence No. | HLA subtype |
|---|---|---|---|
| 384-392 | QCKTCQRKF | 187 | B62, B8 |
| 386-394 | KTCQRKFSR | 188 | A1, A3, A68.1, A1101, A3101 |
| 387-395 | TCQRKFSRS | 189 | B8 |

TABLE 52

| position | amino acid sequence | sequence No. | HLA subtype |
|---|---|---|---|
| 408-416 | KTSEKPFSC | 197 | A0201, B5801 |
| 409-417 | TSEKPFSCR | 198 | A1, A68.1, A3302 |
| 410-418 | SEKPFSCRW | 199 | B40, B4403 |
| 412-420 | KPFSCRWPS | 200 | B3501, B5102 |
| 415-423 | SCRWPSCQK | 201 | A1101 |
| 416-424 | CRWPSCQKK | 202 | B2702, B2705 |
| 417-425 | RWPSCQKKF | 203 | A24, B3801, Cw0401 |
| 418-426 | WPSCQKKFA | 204 | B5102 |
| 419-427 | PSCQKKFAR | 205 | A3302 |
| 420-428 | SCQKKFARS | 206 | B8 |

More preferable examples of the "MHC class I-restricted WT1 peptide consisting of 7-30 amino acid residues containing one cysteine residue" include a peptide comprising the following amino acid sequence:

CMTWNQMNL (SEQ ID NO: 3)

and a peptide comprising an altered amino acid sequence, which is the amino acid sequence of SEQ ID NO: 3 but containing alteration of amino acid residue(s), and having a CTL induction activity. Said "containing the amino acid sequence" and "peptide comprising an altered amino acid sequence containing alteration of amino acid residue(s) in an amino acid sequence, and having a CTL induction activity" are as defined above. Most preferably, a peptide consisting of any amino acid sequence selected from the following amino acid sequences:

```
CMTWNQMNL      (SEQ ID NO: 3)
and

CYTWNQMNL,     (SEQ ID NO: 4)
``` can be mentioned.

As the compound of the formula (1) wherein R' is "an MHC class I-restricted WT1 peptide consisting of 7-30 amino acid residues containing one cysteine residue", a compound represented by the formula (4):

(4)

wherein the bond between C and C is a disulfide bond, or a compound represented by the formula (5):

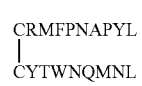
(5)

wherein the bond between C and C is a disulfide bond, is preferable. Of these, a compound represented by the formula (5) is more preferable.

In the present invention, moreover, when a peptide consisting of 1-4 amino acid residues containing one cysteine residue is further bonded to the N-terminal of the "cancer antigen peptide C" which is an MHC class I-restricted WT1 peptide, the compound of the formula (1) may be a compound wherein the thioether group of the cysteine residue of the peptide bonded to the N-terminal of the cancer antigen peptide C is bonded to a thioether group in the formula (16):

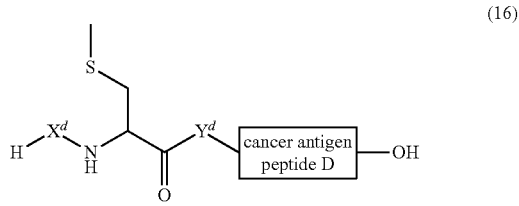
(16)

or to a thioether group of the cysteine residue of the cancer antigen peptide E.

The "$X^d$", "$Y^d$", "cancer antigen peptide D" and "cancer antigen peptide E" in the present invention are as defined for the aforementioned "$X^d$", "$Y^d$", "cancer antigen peptide D" and "cancer antigen peptide E".

In the present invention, the peptide consisting of 1-4 amino acid residues containing one cysteine residue, which is bonded to the N-terminal of the "cancer antigen peptide C" which is an MHC class I-restricted WT1 peptide, is preferably a dipeptide consisting of CA.

In the compound of the formula (1), when a peptide consisting of 1-4 amino acid residues containing one cysteine residue is further bonded to the N-terminal of the "cancer antigen peptide C" which is an MHC class I-restricted WT1 peptide, the compound wherein the thioether group of the cysteine residue of the peptide bonded to the N-terminal of the cancer antigen peptide C is bonded to a thioether group in the formula (16) is preferably a compound represented by the formula (14):

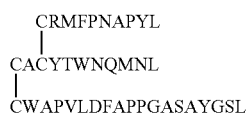
(14)

wherein the bond between C and C is a disulfide bond.

In addition, in the compound of the formula (1), when a peptide consisting of 1-4 amino acid residues containing one cysteine residue is further bonded to the N-terminal of the "cancer antigen peptide C" which is an MHC class I-restricted WT1 peptide, the compound wherein the thioether group of the cysteine residue of the peptide bonded to the N-terminal of the cancer antigen peptide C is bonded to a thioether group in the "cancer antigen peptide E" is preferably a compound represented by the formula (12):

(12)

wherein the bond between C and C is a disulfide bond.

In the "MHC class II-restricted WT1 peptide consisting of 7-30 amino acid residues containing one cysteine residue" in the present invention, the amino acid sequence of the peptide only needs to contain at least one cysteine residue. The number of the cysteine residues to be contained is preferably 1-3, more preferably 1-2, most preferably 1.

In the present invention, "MHC class II-restricted" means the property to induce helper T cell by binding to an MHC class II molecule.

HLA corresponding to the MHC class II-molecule is classified into subtypes of HLA-DR, DQ and DP and the like. Preferable examples of the "MHC class II-restricted" include HLA-DR-restricted, HLA-DQ-restricted and HLA-DP-restricted.

Therefore, the "MHC class II-restricted WT1 peptide" in the present invention is a peptide that binds to an MHC class II antigen in vitro and/or in vivo and induces helper T cells. The number of the amino acid residues of the "MHC class II-restricted WT1 peptide" is 7-30, preferably 14-30.

Examples of the "MHC class II-restricted WT1 peptide consisting of 7-30 amino acid residues containing one cysteine residue" include the peptides described in Table 53. In each Table, the "position" means a position in the amino acid sequence of human WT1 described in SEQ ID NO: 1.

TABLE 53

| position | amino acid sequence | sequence No. |
|---|---|---|
| 117-139 | PSQASSGQARMFPNAPYLPSCLE | 237 |
| 122-140 | SGQARMFPNAPYLPSCLES | 11 |
| 202-233 | CHTPTDSCTGSQALLLRTPYSSDNLYQMTSQL | 9 |
| 328-349 | PGCNKRYFKLSHLQMHSRKHTG | 10 |
| 421-441 | CQKKFARSDELVRHHNMHQRN | 219 |

As the "MHC class II-restricted WT1 peptide consisting of 7-30 amino acid residues containing one cysteine residue", a peptide comprising any amino acid sequence selected from the following amino acid sequences:

```
SGQARMFPNAPYLPSCLES       (SEQ ID NO: 11)
and
PGCNKRYFKLSHLQMHSRKHTG,   (SEQ ID NO: 10)
```
or
a peptide comprising an altered amino acid sequence, which is any amino acid sequence selected from SEQ ID NOs: 10-11 but containing alteration of amino acid residue(s), and having a helper T cell induction activity is preferable.

The "peptide comprising an amino acid sequence" means, as mentioned above, a peptide wherein a further amino acid is added to the N-terminal amino acid and/or C-terminal amino acid of the amino acid sequence. When added to the "MHC class II-restricted WT1 peptide containing one cysteine residue", the addition may be made to the N-terminal side and/or C-terminal side.

The "peptide comprising an altered amino acid sequence containing alteration of amino acid residue(s) in the amino acid sequence, and having a helper T cell induction activity" in the present invention is also called an "altered helper peptide". The altered helper peptide means a peptide that consists of an amino acid sequence wherein 1 to 3 amino acids are deleted, substituted and/or added and binds to MHC class II to induce helper T cell. The number of the amino acids to be added (also including insertion) is preferably 1-3. The number of the amino acids to be deleted is preferably 1-5. In the alteration, the amino acid to be added or amino acid to be substituted may be a non-natural amino acid other than the kinds of amino acids encoded by the gene.

As the altered helper peptide, for example, the following peptides can be mentioned:
SGQAYMFPNAPYLPSCLES (SEQ ID NO: 12) (see patent document 6),
SGQAYMFPNAPYLPSC (SEQ ID NO: 19) and
SGQAYMFPNAPYLPSC (SEQ ID NO: 25), which are altered helper peptide of SGQARMFPNAPYLPSCLES (SEQ ID NO: 11); and
GCNKRYFKLSHLQMHSRK (SEQ ID NO: 20),
PGCNKRYFKLSHLQMHSRKH (SEQ ID NO: 21),
CNKRYFKLSHLQMHSRK (SEQ ID NO: 22),
CNKRYFKLSHLQMHSRKH (SEQ ID NO: 23) and
CNKRYFKLSHLQMHSRKHTG (SEQ ID NO: 24), which are altered helper peptide of PGCNKRYFKLSHLQMHSRKHTG (SEQ ID NO: 10).

As the "MHC class II-restricted WT1 peptide consisting of 7-30 amino acid residues containing one cysteine residue", a peptide consisting of any amino acid sequence selected from the following amino acid sequences:

```
SGQARMFPNAPYLPSC,         (SEQ ID NO: 19)
SGQAYMFPNAPYLPSC,         (SEQ ID NO: 25)
SGQARMFPNAPYLPSCLES,      (SEQ ID NO: 11)
SGQAYMFPNAPYLPSCLES,      (SEQ ID NO: 12)
PGCNKRYFKLSHLQMHSRK,      (SEQ ID NO: 20)
PGCNKRYFKLSHLQMHSRKH,     (SEQ ID NO: 21)
PGCNKRYFKLSHLQMHSRKHTG,   (SEQ ID NO: 10)
CNKRYFKLSHLQMHSRK,        (SEQ ID NO: 22)
CNKRYFKLSHLQMHSRKH        (SEQ ID NO: 23)
and
CNKRYFKLSHLQMHSRKHTG      (SEQ ID NO: 24)
```
is more preferable.

As the compound of the formula (1) wherein $R^1$ is "an MHC class II-restricted WT1 peptide consisting of 7-30- amino acid residues containing one cysteine residue", a compound represented by the formula (6):

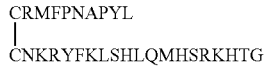
(6)

wherein the bond between C and C is a disulfide bond, a compound represented by the formula (7):

(7)

wherein the bond between C and C is a disulfide bond, a compound represented by the formula (8):

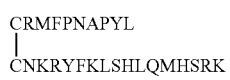
(8)

wherein the bond between C and C is a disulfide bond, and a compound represented by the formula (9):

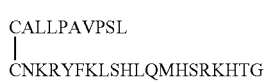
(9)

wherein the bond between C and C is a disulfide bond, are preferable.

The present invention also provides a composition comprising the compound of the present invention and one or more MHC class II-restricted WT1 peptides.

Examples of the compound of the present invention to be contained in the composition of the present invention include a compound represented by the formula (3):

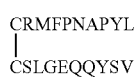
(3)

wherein the bond between C and C is a disulfide bond, a compound represented by the formula (4):

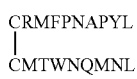
(4)

wherein the bond between C and C is a disulfide bond, and a compound represented by the formula (5):

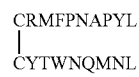
(5)

wherein the bond between C and C is a disulfide bond.

Examples of the MHC class II-restricted WT1 peptide to be contained in the composition of the present invention include the following amino acid sequences:

| | |
|---|---|
| CNKRYFKLSHLQMHSRK, | (SEQ ID NO: 22) |
| CNKRYFKLSHLQMHSRKH, | (SEQ ID NO: 23) |
| CNKRYFKLSHLQMHSRKHTG, | (SEQ ID NO: 24) |
| WAPVLDFAPPGASAYGSL, | (SEQ ID NO: 244) |
| CWAPVLDFAPPGASAYGSL and | (SEQ ID NO: 242) |
| WAPVLDFAPPGASAYGSLC. | (SEQ ID NO: 243) |

The present invention also provides a synthesis method of a compound wherein two different MHC class I-restricted WT1 peptide and MHC class II-restricted WT1 peptide, or two different MHC class I-restricted WT1 epitope and MHC class II-restricted WT1 epitope are each bonded via a disulfide bond. The method of the present invention includes the following steps (1)-(3).

In step (1) of the present invention, a peptide wherein a carbonyl group of the C-terminal amino acid of C(Mmt)A and the N-terminal amino group of the cancer antigen peptide C are bonded is synthesized by using Fmoc-C(Mmt)A-SBn and cancer antigen peptide C.

The "cancer antigen peptide C" is as defined for the aforementioned "cancer antigen peptide C". "Fmoc" is a 9-fluorenylmethoxycarbonyl group. "Mmt" is a monomethoxytrityl group. "SBn" is a thiobenzyl group.

In step (2) of the present invention, a peptide wherein a thioether group of the cysteine residue of the cancer antigen peptide C in the peptide obtained in the aforementioned step (1) and a thioether group of the cysteine residue bonded to the N-terminal of cancer antigen peptide A are bonded is synthesized by using the peptide obtained in the aforementioned step (1) and cancer antigen peptide A wherein one cysteine residue protected by Npys group is bonded to the N-terminal.

The "cancer antigen peptide A" is as defined for the aforementioned "cancer antigen peptide A". "Npys" is a 3-nitro-2-pyridylthio group.

In step (3) of the present invention, a peptide wherein a thioether group of the cysteine residue bonded to the N-terminal of the cancer antigen peptide A in the peptide obtained in the aforementioned step (2), and a thioether group of the cysteine residue of the cancer antigen peptide D are bonded, is synthesized by using the peptide obtained in the aforementioned step (2) and cancer antigen peptide D containing a cysteine residue protected by Spy group.

The "cancer antigen peptide D" is as defined for the aforementioned "cancer antigen peptide D". "SPy" is a 2-pyridylsulfide group.

The compound and peptide of the present invention, and peptides to be intermediates therefor can be produced according to the method described in the Examples of the present specification or a method to be generally used for the peptide synthesis. Examples of the production method include the methods described in the documents (Peptide Synthesis, Interscience, New York, 1966; The Proteins, Vol. 2, Academic Press Inc., New York, 1976; peptide synthesis, Maruzen Co., LTD., 1975; Basics and Experiment of Peptide Synthesis, Maruzen Co., LTD., 1985; Development of Pharmaceutical Product subsequent vol. 14, Peptide Synthesis, Hirokawa Shoten, 1991) and the like.

Examples thereof include a production method by a solid phase synthesizer using Fmoc method or Boc method, and a production method by sequential condensation of Boc-amino acid or Z-amino acid by liquid phase synthesis process (Fmoc is a 9-fluorenylmethoxycarbonyl group, Boc is a t-butoxycarbonyl group, and Z is a benzyloxycarbonyl group).

In the intermediate for the production of the compound of the present invention, a functional group such as an amino group, a carboxy group, a mercapto group and the like can be protected by a suitable protecting group or deprotected as necessary using protection and deprotection techniques. As preferable protecting groups, protection method and deprotection method are described in detail in "Protective Groups in Organic Synthesis 2nd Edition (John Wiley & Sons, Inc.; 1990)" and the like. Examples of the mercapto-protecting group include an acetamidomethyl group, a trityl group and the like.

When the compound of the present invention has a disulfide bond, the disulfide bond can be formed between two different peptides containing a cysteine residue or between peptide containing a cysteine residue and cysteine according to a method generally used for peptide chemistry. Examples of the formation method of the disulfide bond include the methods described in the documents (Peptide Synthesis, Interscience, New York, 1966; The Proteins, Vol. 2, Academic Press Inc., New York, 1976; peptide synthesis, Maruzen Co., LTD., 1975; Basics and Experiment of peptide synthesis, Maruzen Co., LTD., 1985; Development of Pharmaceutical Product sequential vol. 14, Peptide Synthesis, Hirokawa Shoten, 1991) and the like.

Specifically, when a peptide contains one cysteine residue, a compound having a disulfide bond (disulfide compound) can be produced by removing all protecting groups including the mercapto-protecting group on the cysteine side chain and oxidizing in an inert solvent. In addition, it can be produced by mixing two intermediates having a mercapto group in a suitable solvent to allow oxidation. As a method for the oxidation, a known method for forming a disulfide bond in general peptide synthesis can be selected as appropriate. For example, iodine oxidation, a method including air oxidation reaction under alkali conditions, a method for forming a disulfide bond by adding an oxidant under alkaline or acidic conditions and the like can be mentioned. Here, as the oxidant, iodine, dimethyl sulfoxide (DMSO), potassium ferricyanide and the like can be mentioned. As the solvent, water, acetic acid, methanol, chloroform, DMF, DMSO and the like, or a mixture thereof can be used. An oxidation reaction often affords a mixture of symmetric, asymmetric disulfide compounds. The object asymmetric disulfide compound can be obtained by purifying by various chromatography, recrystallization and the like. Alternatively, an intermediate having an activated mercapto group and an intermediate having a mercapto group are mixed to form a selective disulfide bond. As the intermediate having an activated mercapto group, a mercapto group bonded with an Npys group (3-nitro-2-pyridinesulphenyl group) and the like can be mentioned. Alternatively, one intermediate and, for example, 2,2'-dithiobis(5-nitropyridine) are mixed in advance to activate the mercapto group, and then the other intermediate is added, whereby a selective disulfide bond can be formed (Tetrahedron Letters. Vol. 37. No. 9, pp. 1347-1350).

Also, when two or more cysteine residues are contained in the peptide, a method similar to the aforementioned method can be used. In this case, an isomer with a different manner of disulfide bond is obtained. A dimer wherein a disulfide bond is formed between the object cysteine residues can be obtained by using a particular combination of the cysteine side chain-protecting groups. As the aforementioned combination of protecting groups, MeBzl (methylbenzyl) group and Acm (acetamidomethyl) group, Trt (trityl) group and Acm group, Npys (3-nitro-2-pyridylthio) group and Acm group, S-Bu-t (S-tert-butyl) group and Acm group and the like can be mentioned. For example, in the case of a combination of MeBzl group and Acm group, a method of forming a disulfide bond between cysteine residues protected Acm group, which includes removing protecting group other than MeBzl group and cysteine side chain, subjecting a solution containing a peptide monomer to air oxidation reaction to form a disulfide bond between the deprotected cysteine residues, and then performing deprotection with iodine and oxidation and the like can be mentioned.

The obtained compound, peptide and intermediate of the present invention can be purified according to a method known to those of ordinary skill in the art and a method generally used for peptide chemistry. For example, they can be purified by various chromatography (e.g., silica gel column chromatography, ion exchange column chromatography, gel filtration, reversed-phase chromatography), recrystallization and the like. For example, as the recrystallization solvent, alcohol solvents such as methanol, ethanol, 2-propanol and the like, ether solvents such as diethyl ether and the like, ester solvents such as ethyl acetate and the like, aromatic hydrocarbon solvents such as benzene, toluene and the like, ketone solvents such as acetone and the like, hydrocarbon solvents such as hexane and the like, aprotic solvents such as dimethylformamide, acetonitrile and the like, water, a mixed solvent thereof and the like can be used. As other purified by methods, the methods described in Jikken Kagaku Kouza (The Chemical Society of Japan ed., Maruzen) vol. 1 etc., and the like can be used.

The purified by methods of the disulfide compound are described in the documents (Peptide Synthesis, Interscience, New York, 1966; The Proteins, Vol. 2, Academic Press Inc., New York, 1976; peptide synthesis, Maruzen Co., LTD., 1975; Basics and Experiment of Peptide Synthesis, Maruzen Co., LTD., 1985; Development of Pharmaceutical Product sequential vol. 14 synthesis, Hirokawa Shoten, 1991) and the like. Among these, HPLC is preferable.

When the compound of the present invention has one or more asymmetric points, it can be produced according to a general method and using a starting material having the asymmetric points (amino acid). To increase the optical purity of the compound of the present invention, moreover, optical resolution and the like may be performed at a suitable stage of the production step. As the optical resolution method, for example, a diastereomer method including forming a salt of the compound of the present invention or an intermediate thereof with an optically active acid (e.g., monocarboxylic acids such as mandelic acid, N-benzyloxyalanine, lactic acid and the like, dicarboxylic acids such as tartaric acid, o-diisopropylidenetartaric acid, malic acid and the like, or sulfonic acids such as camphorsulfonic acid, bromocamphorsulfonic acid and the like) in an inert solvent (e.g., alcohol solvents such as methanol, ethanol, 2-propanol and the like, ether solvents such as diethyl ether and the like, ester solvents such as ethyl acetate and the like, hydrocarbon solvents such as toluene and the like, aprotic solvents such as acetonitrile and the like, and a mixed solvent thereof) can be used. When the compound of the present invention or intermediate has an acidic functional group such as carboxy group and the like, optical resolution can also be performed by forming a salt with an optically active amine (e.g., organic amine such as α-phenethylamine, kinin, quinidine, cinchonidine, cinchonine, strychnine and the like).

The temperature for forming a salt is selected from the range of room temperature to the boiling point of the solvent. To improve the optical purity, it is desirable to once raise the temperature to around the boiling point of the solvent. When the precipitated salt is collected by filtration, it can be cooled as necessary to increase the yield. A suitable amount of the optically active acid, or amine to be used is within the range of about 0.5-about 2.0 equivalents, preferably about 1 equivalent, relative to the substrate. Where necessary, the crystals may be recrystallized in an inert solvent (e.g., alcohol solvents such as methanol, ethanol, or 2-propanol and the like, ether solvents such as diethyl ether and the like, ester solvents such as ethyl acetate and the like, hydrocarbon solvents such as toluene and the like, aprotonic solvents such as acetonitrile and the like, and a mixed solvent thereof) to also afford an optically active salt with high purity. Where necessary, optically resolved salt may be treated with an acid or base by a general method to give a free form.

Examples of the "pharmaceutically acceptable salt" in the present invention include acid addition salt and base addition salt. Examples of the acid addition salt include inorganic acid salts such as hydrochloride, hydrobromide, sulfate, hydroiodide, nitrate, phosphate and the like, and organic acid salts such as citrate, oxalate, acetate, formate, propionate, benzoate, trifluoroacetate, maleate, tartrate, methanesulfonate, benzenesulfonate, p-toluenesulfonate and the like. Examples of the base addition salt include salts with inorganic base such as sodium salt, potassium salt, calcium salt, magnesium salt, ammonium salt and the like, salts with organic base such as triethylammonium salt, triethanolammonium salt, pyridinium salt, diisopropylammonium salt etc., and the like, furthermore, amino acid salts of basic or acidic amino acids such as arginine, aspartic acid, glutamic acid and the like.

The present invention also encompasses hydrates, solvates such as ethanol solvate and the like of the compound of the present invention or a pharmaceutically acceptable salt thereof. Furthermore, the present invention encompasses any stereoisomers such as any diastereomer, enantiomer and the like and any crystals in any embodiments, of the compound represented by the formula (1), that can be present.

In general, in the production of peptide, various byproducts such as amino acid-defective peptide, peptide degraded by hydrolysis, oxidation and the like, peptide with racemized amino acid and the like occur in a step of condensing optically active α-amino acid, a step of removing various protecting groups, a step of cleaving peptide from a resin and the like. At a laboratory scale, various chromatographys (e.g., silica gel column chromatography, ion exchange column chromatography, gel filtration, and reversed-phase chromatography) are combined to remove such impurities, whereby peptide and a compound with high purity can be obtained. However, it is not easy to obtain peptide and a compound with high purity at an industrial scale to provide pharmaceutical products.

The compound of the present invention has physicochemical properties to allow mass production of a drug substance for pharmaceutical products. Specifically, it has high solubility, is superior in the stability in a solution, is hard to become gelled when concentrated and the like, and the compound can be produced easily as a drug substance with high purity at a large scale by a purified by step using column chromatography such as reversed-phase HPLC and the like.

The thus-produced compound of the present invention is superior in the stability to oxidant and the like in a solution, since the cysteine residues form a disulfide bond and the like, and retains given quality as a drug substance of medicaments and efficient CTL induction activity.

The compound of the present invention is useful as an active ingredient of a CTL induction agent for cancer immunotherapy, an active ingredient of a cancer vaccine, or an active ingredient of a pharmaceutical composition. That is, the compound of the present invention has, as shown in the Examples of the present specification, superior immunogenicity and can efficiently show a superior CTL induction activity. In addition, CTL induced by the compound of the present invention can surprisingly recognize natural type partial peptide of WT1 inherently present in cancer cells.

The CTL induction activity can be detected by measuring the number of CTL by the HLA tetramer method (Int. J. Cancer: 100, 565-570 (2002)) or limiting dilution method (Nat. Med.: 4, 321-327 (1998)). Alternatively, for example, HLA-A24-restricted CTL induction activity can be examined by using the HLA-A24 model mouse described in WO 02/47474 and Int. J. Cancer: 100, 565-570 (2002) and the like.

Therefore, the compound of the present invention can be used as a therapeutic drug or prophylactic drug (recurrence preventive drug) for cancer expressing WT1 gene or cancer associated with an increase in the WT1 gene expression level. Examples of the cancer include hematologic cancer such as leukemia, myelodysplastic syndrome, multiple myeloma, malignant lymphoma and the like, and solid tumor such as gastric cancer, colorectal cancer, lung cancer, breast cancer, germ cell cancer, liver cancer, skin cancer, urinary bladder cancer, prostate cancer, uterine cancer, cervical cancer, ovarian cancer, brain tumor and the like.

The compound of the present invention or a pharmaceutically acceptable salt thereof can be an active ingredient of a CTL induction agent for cellular immunotherapy of cancer, an active ingredient of a cancer vaccine or/and an active ingredient of a pharmaceutical composition, by formulating each compound or salt in a suitable form.

The compound of the present invention can be administered together with a carrier acceptable as a medicament such as a suitable adjuvant so that its cellular immunity will be established effectively. As the adjuvant, those described in a document (Clin. Microbiol. Rev., 7: 277-289, 1994) and the like are applicable. Specifically, fungus-derived components, GM-CSF, cytokines such as interleukin-2, interleukin-7, interleukin-12 and the like, plant-derived components, marine organism-derived components, mineral gel such as aluminum hydroxide, lysolecithin, surfactants such as pluronic polyol, polyanion, peptide, oil emulsion (emulsion preparation) and the like can be mentioned. As the fungus-derived components, lipid A, monophosphoryl lipid A, which is a derivative thereof, dead bacteria (*Mycobacterium* bacteria such as BCG bacteria and the like), bacterium-derived proteins, polynucleotides, Freund's Incomplete Adjuvant, Freund's Complete Adjuvant, cell wall skeleton components (e.g., BCG-CWS and the like), trehalose dimycolate (TDM) and the like can be mentioned.

In addition, the compound of the present invention can also be administered in the form of a liposome preparation, a particulate preparation including binding to beads with a diameter of several a preparation including binding to a lipid and the like.

Furthermore, the compound of the present invention (conjugate) can be administered together with an MHC class II-restricted WT1 peptide (namely, helper peptide). As a method for co-administration, a conjugate and a helper peptide may be individually administered. A cocktail preparation (cocktail agent, cocktail) containing a conjugate and a helper peptide in a single pharmaceutical composition is more preferable. The cocktail preparation contains a conjugate capable of producing MHC class I-restricted WT1 peptide (i.e., killer peptide) and MHC class II-restricted WT1 peptide (namely, helper peptide). Therefore, by administering the cocktail preparation containing a helper peptide, as a cancer vaccine for cancer immunotherapy, helper T cells important for functional promotion of other T cells including CTL can also be activated, and function and efficacy (cellular immunocompetence and the like) of the conjugate can be improved.

The MHC class II-restricted WT1 peptide (namely, helper peptide) is as described in the DESCRIPTION. Examples of the helper peptide for the cocktail preparation include the following amino acid sequences:

```
CNKRYFKLSHLQMHSRK,        (SEQ ID NO: 22)

CNKRYFKLSHLQMHSRKH,       (SEQ ID NO: 23)

CNKRYFKLSHLQMHSRKHTG,     (SEQ ID NO: 24)

WAPVLDFAPPGASAYGSL,       (SEQ ID NO: 244)

CWAPVLDFAPPGASAYGSL       (SEQ ID NO: 242)
and

WAPVLDFAPPGASAYGSLC.  (SEQ ID NO: 243)
```

Of these, WAPVLDFAPPGASAYGSL (SEQ ID NO: 244) is preferable.

It could be confirmed that the cocktail preparation shows improved efficacy as a cancer vaccine such as cellular immunocompetence and the like, as shown in, for example, Examples and Experimental Examples in the DESCRIPTION.

While the dose of the compound of the present invention in the preparation can be appropriately controlled according to the treatment object disease, age and body weight of the patients and the like, it is generally 0.0001 mg-1000 mg, preferably 0.001 mg-1000 mg, more preferably 0.1 mg-10 mg.

As the administration method, intradermal administration, subcutaneous administration, intramuscular administration, intravenous administration, transdermal administration and the like can be mentioned. Intradermal administration and subcutaneous administration are preferable since they efficiently induce CTL. While the administration frequency and administration intervals can be appropriately controlled according to the prophylaxis or treatment of object disease, and individual difference in patients, it is generally multiple times, and administration once per several days to several months is preferable.

By administering a pharmaceutical composition containing such compound of the present invention as an active ingredient to WT1 positive patients, a method for the prophylaxis or treatment of cancer can be provided.

EXAMPLES

The present invention is specifically explained in the following by referring to Examples, to which, however, the invention is not limited.

Example 1

Synthesis of the compound represented by the formula (5):

wherein the bond between C and C is a disulfide bond.

Step 1. Synthesis of H-Cys(Npys)-Arg-Met-Phe-Pro-Asn-Ala-Pro-Tyr-Leu-OH (Synthesis of C(Npys)RMFPNAPYL)

Using Fmoc-Leu-Alko-resin (Alko is p-alkoxybenzylalcohol), 282 mg, (manufactured by Watanabe Chemical; 0.71 mmol/g, 0.2 mmol) as a starting material, the peptide chain was assembled by solid phase synthesis according to Fmoc/tBu method. Solid phase synthesis was performed using CS336X peptide synthesizer manufactured by CS Bio, and deprotection of Fmoc group was performed by treatment with a DMF solution of 20% piperidine for 5 min and for 20 min. Coupling of protected amino acid was performed by reaction with a DMF solution of 1.05 mmol of protected amino acid, 1 mmol HBTU and 2 mmol DIPEA for 1 hr. The obtained resin was washed with DMF and ether, and dried under reduced pressure to give Boc-Cys(Npys)-Arg(Pmc)-Met-Phe-Pro-Asn(Trt)-Ala-Pro-Tyr(tBu)-Leu-Alko-resin (630 mg). To this peptide resin was added a mixture of TFA/H₂O/TIS=95/2.5/2.5 (10 ml), and the mixture was shaken at room temperature for 2 hr. The resin was filtered off, and the reaction mixture was concentrated under reduced pressure. The reaction mixture was ice-cooled and diethyl ether (50 ml) was added. The resulting precipitate was collected by filtration, washed with ether and dried under reduced pressure to give crude peptide (217 mg). The obtained crude peptide solution was dissolved in a mixture of 20% aqueous acetic acid (7 ml) and acetonitrile (1 ml) and purified by reversed-phase HPLC.

pump: manufactured by Shimadzu; LC-8A
column: YMC ODS-A 3 cmφ×25 cmL, 10 µm
eluate 1: H₂O/0.1% TFA
eluate 2: CH₃CN/0.1% TFA
flow rate: 20 ml/min
detection: UV220 nm The crude peptide solution was injected to a column equilibrated with 15% of eluate 2. Thereafter, the concentration of eluate 2 was raised to 37% over 10 min, and thereafter raised at a rate of 0.24% per minute. Fractions containing the object product were collected and freeze dried to give H-Cys(Npys)-Arg-Met-Phe-Pro-Asn-Ala-Pro-Tyr-Leu-OH (53 mg).

mass spectrometry: LC-ESI/MS m/z=1366.1 [M+1]⁺ (Calculated=1366.6)

Step 2. Synthesis of (H-Cys-Tyr-Thr-Trp-Asn-Gln-Met-Asn-Leu-OH)(H-Cys-Arg-Met-Phe-Pro-Asn-Ala-Pro-Tyr-Leu-OH) Disulfide Bond

[That is, synthesis of a compound represented by the formula (5):

wherein the bond between C and C is a disulfide bond.]

H-Cys(Npys)-Arg-Met-Phe-Pro-Asn-Ala-Pro-Tyr-Leu-OH (50 mg) obtained in step 1 and H-Cys-Tyr-Thr-Trp-Asn- Gln-Met-Asn-Leu-OH (i.e., CYTWNQMNL (SEQ ID NO: 4)) (43 mg) synthesized by a known method (e.g., WO07/063903) were mixed, DMSO (1 mL) was added, and the mixture was stirred at room temperature for 20 min. The reaction mixture was diluted with 0.1% TFA water (5 ml) and purified by reversed-phase HPLC.

pump: manufactured by Shimadzu; LC-8A
column: YMC ODS-A 3 cmϕ×25 cmL, 10 μm
eluate 1: $H_2O$/0.1% TFA
eluate 2: $CH_3CN$/0.1% TFA
flow rate: 20 ml/min
detection: UV220 nm The reaction solution was injected to a column equilibrated with 25% of eluate 2. Thereafter, the concentration of eluate 2 was raised at a rate of 0.25% per minute. Fractions containing the object product were collected, freeze dried, re-purified by reversed-phase HPLC, and freeze dried to give (H-Cys-Tyr-Thr-Trp-Asn-Gln-Met-Asn-Leu-OH)(H-Cys-Arg-Met-Phe-Pro-Asn-Ala-Pro-Tyr-Leu-OH) disulfide bond (i.e., a compound represented by the formula (5), 21 mg).

mass spectrometry: LC-ESI/MS m/z=1191.8 $[M+2]^{2+}$ (Calculated=1191.9)

Example 2

Synthesis of Peptide Consisting of the Following Amino Acid Sequence

CRMFPNAPYL          (SEQ ID NO: 13)

step 1. Using Fmoc-Leu-Alko-resin (Alko is p-alkoxybenzylalcohol) (338 mg, manufactured by Watanabe Chemical; 0.74 mmol/g, 0.25 mmol) as a starting material, and solid phase synthesis as in the method described in Example 1 was performed twice to give H-Cys(Trt)-Arg(Pmc)-Met-Phe-Pro-Asn(Trt)-Ala-Pro-Tyr(tBu)-Leu-Alko-resin (1.54 g). To this peptide resin was added a mixture of TFA/$H_2O$/TIS=95/2.5/2.5 (15 ml), and the mixture was shaken at room temperature for 3 hr. The resin was filtered off, and the reaction mixture was concentrated under reduced pressure. The reaction mixture was ice-cooled and diethyl ether (50 ml) was added. The resulting precipitate was collected by filtration, washed with ether and dried under reduced pressure to give crude peptide (637 mg).

mass spectrometry: LC-ESI/MS m/z=1211.9 $[M+1]^+$ (Calculated=1212.5)

step 2. The crude peptide (321 mg) obtained in step 1 was dissolved in TFA (10 ml), and charged, by a pump of HPLC, into a YMC-PACK ODS-A 3 cmϕ×25 cmL column equilibrated with HPLC (manufactured by Shimadzu; LC6AD) eluate 1=$H_2O$/0.1% TFA. This state was maintained for about 20 min and, after 20 min, the concentration of eluate 2=$CH_3CN$/0.1% TFA was raised to 270. Thereafter, while monitoring the eluate of the object peptide by 220 nm UV, the concentration of eluate 2 was raised at a rate of 0.25% per minute and the fractions containing the object product were collected. The peptide (100 mg) obtained after freeze dry was purified again by reversed-phase under the same conditions, and acetonitrile was evaporated under reduced pressure and the residue was freeze dried to give the object peptide (CRMFPNAPYL (SEQ ID NO: 13), 37.2 mg).

pump: manufactured by Shimadzu; LC-6A
column: YMC ODS-A 3 cmϕ×25 cmL, 10 μm
eluate 1: $H_2O$/0.1% TFA
eluate 2: $CH_3CN$/0.1% TFA
flow rate: 20 ml/min
detection: UV220 nm mass spectrometry: LC-ESI/MS m/z=1212.0 $[M+1]^+$ (Calculated=1211.6)

Examples 3-5

By a method similar to that in Example 2, peptides consisting of the amino acid sequence of SEQ ID NO: 16, 18 or 17 were synthesized. Table 54 shows the synthesized amount and the results of mass spectrometry.

TABLE 54

| Ex. No. | amino acid sequence | sequence No. | synthesized amount (mg) | mass spectrometry: LC-ESI/MS m/z | mass spectrometry: Calculated |
|---|---|---|---|---|---|
| 3 | CALLPAVPSL | 16 | 42 | 983.8 $[M + 1]^+$ | 983.2 |
| 4 | CRVPGVAPTL | 18 | 53 | 1012.7 $[M + 1H]^+$ | 1012.2 |
| 5 | CSLGEQQYSV | 17 | 31 | 1113.7 $[M + 1]^+$ | 1113.2 |

Experimental Example 1

Time-Course Changes of Trimming of N-Terminal Amino Acid by ERAP1

The peptides of SEQ ID NOs: 13, 16, 18 and 17 synthesized in Examples 2-5 were evaluated for the trimming of the N-terminal amino acid by ERAP1 (PLoS One November 2008, vol. 3, Issue 11, e3658).

30 μl of ERAP1 (2.0 mg/ml) in PBS buffer solution was added to 258 μl of TrisHCl buffer. DMSO solution (12.0 μl) of 10 mM each peptide was added to the aforementioned ERAP1 solution, and the mixture was blended well and stood at room temperature. 1.0, 2.0, 4.0, 8.0 hr later, 50 μl of a sample was added to 150 μl of MeOH to terminate the reaction, 25 μl was injected into UFLC (analysis conditions shown below), and AUC of the object peptide was determined. Peptide obtained by trimming was chemically synthesized separately, and analyzed under similar conditions free of enzyme. The formation ratio of peptide obtained by trimming was determined based on the obtained AUC.

Analysis Conditions
pump: UFLC manufactured by Shimadzu
column: Shim-pack XR-ODS 3.0 mmi.d.×75 mm
solution: 0.1% TFA $H_2O$(A)-0.1% TFA $CH_3CN$(B)
oven temperature: 40° C.
flow rate: 1.0 ml/min
detection wavelength: λ=220 nm
gradient:
1. Concentration of SOLUTION B was raised from 1.0% to 70% from 0.0 min to 5.0 min
2. Concentration of SOLUTION B was raised from 1.0% to 50% from 0.0 min to 5.0 min object peptide:

As for the peptides synthesized in Examples 2-5, the amino acid sequences of the peptides obtained by trimming of N-terminal amino acid by ERAP1 are shown in Table 55.

TABLE 55

| Example No. | peptide used for trimming test | | peptide obtained by trimming | |
|---|---|---|---|---|
| | amino acid sequence | sequence No. | amino acid sequence | sequence No. |
| 2 | CRMFPNAPYL | 13 | RMFPNAPYL | 2 |
| 3 | CALLPAVPSL | 16 | ALLPAVPSL | 5 |
| 4 | CRVPGVAPTL | 18 | RVPGVAPTL | 7 |
| 5 | CSLGEQQYSV | 17 | SLGEQQYSV | 6 |

Time-course changes in the formation rate of the peptides obtained by trimming are shown in Table 56 and FIG. 1.

TABLE 56

| Example No. | sequence No. | gradient | formation rate (%) | | | |
|---|---|---|---|---|---|---|
| | | | 1 hr later | 2 hr later | 4 hr later | 8 hr later |
| 2 | 13 | 1 | 25.5 | 35.2 | 46.2 | 47.6 |
| 3 | 16 | 1 | 65.5 | 50.6 | 13.5 | 0 |
| 4 | 18 | 1 | 59.1 | 57.5 | 30.1 | 7.80 |
| 5 | 17 | 2 | 77.6 | 72.8 | 46.0 | 7.90 |

The trimming results strongly suggest that, in any Cys-extended peptides (SEQ ID NOs: 13, 16, 17 and 18), Cys on the extended N-terminal is selectively cleaved by ERAP-1, namely, Cys-extended peptide undergoes appropriate trimming by ERAP-1 without marked dependence on the peptide sequence, and is finally converted to the object cancer antigen peptide (SEQ ID NO: 2, 5, 6 or 7).

Experimental Example 2

Evaluation of In Vivo CTL Induction Ability Using HLA-A0201 Transgenic Mouse and HLA-A2402 Transgenic Mouse The compound represented by the formula (5) synthesized in Example 1 was evaluated for the CTL induction ability by an in vivo CTL induction test using HLA-A0201 transgenic mouse and HLA-A2402 transgenic mouse. The compound represented by the formula (5):

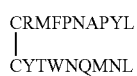

(5)

wherein the bond between C and C is a disulfide bond, is, in particular, a compound of the aforementioned formula (1), wherein cancer antigen peptide A is RMFPNAPYL (SEQ ID NO: 2) and cancer antigen peptide B is CYTWNQMNL (SEQ ID NO: 4). RMFPNAPYL (SEQ ID NO: 2) is a HLA-A0201-restricted WT1 peptide, and CYTWNQMNL (SEQ ID NO: 4) is a HLA-A24-restricted WT1 peptide.

HLA-A0201 transgenic mouse (C57BL/6CrHLA-A2.1DR1) is a mouse which is defective in mouse MHC, and expresses chimera HLA of human MHC HLA-A0201 and mouse MHC H-2D$^b$, and HLA-DRB1*0101. Using this mouse, HLA-A02 positive peptide capable of inducing CTL in human can be selected (Eur J Immunol. 2004; 34: 3060-9).

On the other hand, HLA-A2402 transgenic mouse (C57BL/6CrHLA-A2402/K$^b$) is a mouse that expresses chimera HLA of human MHC HLA-A2402 and mouse MHC H-2K$^b$. Using this mouse, HLA-A24 positive peptide capable of inducing CTL in human can be selected (Int J Cancer. 2002; 100: 565-70).

Whether the administration of a compound represented by the formula (5) results in the induction of CTL specific to the object peptide (SEQ ID NO: 2, 4) was judged based on the measurement of IFNγ production by re-stimulation, with the peptide (SEQ ID NO: 2, 4), of the splenocyte derived from the above-mentioned mouse administered with a compound represented by the formula (5).

Specifically, a compound represented by the formula (5) was dissolved in dimethyl sulfoxide (DMSO) at 40 mg/mL, further diluted with water for injection to 5 mg/mL, and emulsified by mixing with an equal amount of incomplete Freund's adjuvant (IFA). The emulsified compound was intradermally administered to 4 sites at the base of tail of a mouse at 250 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at 0.15×10$^6$ cells/well, and HLA-A2402 transgenic mouse-derived splenocytes were plated at 1×10$^6$ cells/well, on the blocked ELISPOT plate. Peptide (SEQ ID NO: 2, 4) was dissolved in DMSO at 40 mg/mL, and further diluted with RPMI1640 medium containing 10% FBS to 40 μg/mL. The diluted peptide (SEQ ID NO: 2) was added to the HLA-A0201 transgenic mouse-derived splenocytes at a final concentration of 10 μg/mL. In addition, the diluted peptide (SEQ ID NO: 4) was added to the HLA-A2402 transgenic mouse-derived splenocytes at a final concentration of 10 μg/mL. The splenocytes added with the peptide were cultivated for 20 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 2:
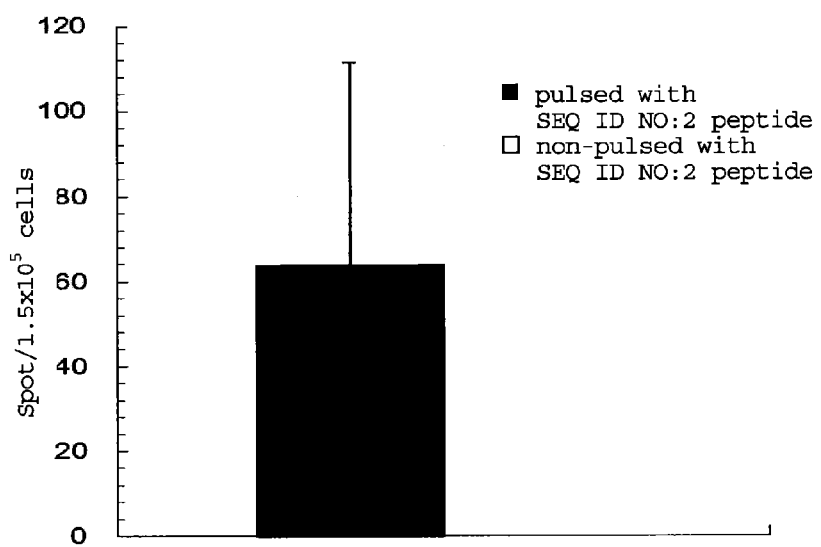
FIG. 2 is a Figure showing the test results of Experimental Example 2 as to the in vivo CTL induction ability of a compound represented by the formula (5) synthesized in Example 1, by IFNγ ELISPOT assay using HLA-A0201 transgenic mouse.
Figure 3:
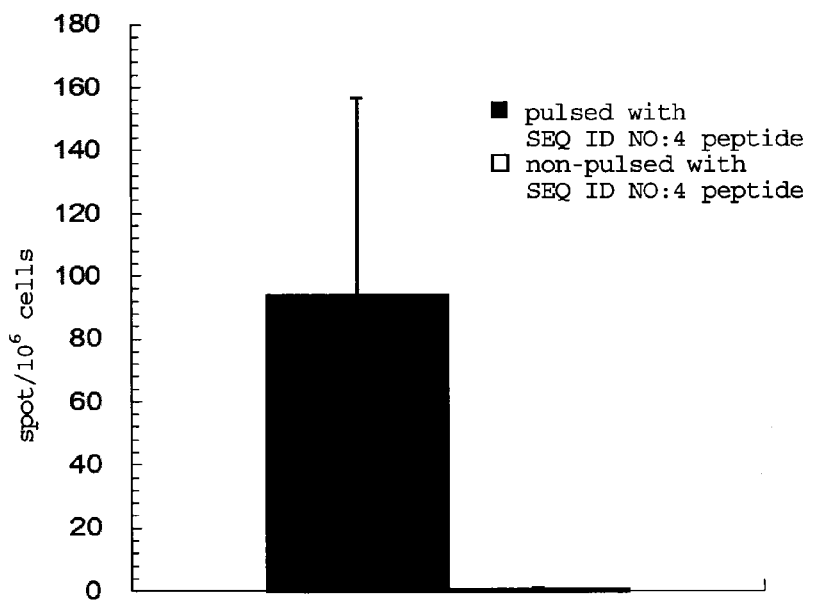
FIG. 3 is a Figure showing the test results of Experimental Example 2 as to the in vivo CTL induction ability of a compound represented by the formula (5) synthesized in Example 1, by IFNγ ELISPOT assay using HLA-A2402 transgenic mouse.

The results of IFNγ ELISPOT assay using HLA-A0201 transgenic mouse are shown in FIG. 2, and the results of IFNγ ELISPOT assay using HLA-A2402 transgenic mouse are shown in FIG. 3.

In each Figure, the vertical axis shows the number of cells that reacted in the plated cells. In FIG. 2, the black bar and the white bar show the results of culture of HLA-A0201 transgenic mouse-derived splenocytes in the presence or absence of the object peptide represented by SEQ ID NO: 2, and in FIG. 3, the black bar and the white bar show the results of culture of HLA-A2402 transgenic mouse-derived splenocytes in the presence or absence of the object peptide represented by SEQ ID NO: 4. That is, the difference in the values of the black bar and the white bar show the number of the object, each peptide-specific CTL induced in the mouse in vivo by the administration of a compound represented by the formula (5).

In each Figure, the value of the white bar is not detected. This means that the splenocytes of respective transgenic mice did not react at all in the absence of the object peptide. As a result of this test, IFNγ production specific to the object peptide shown by SEQ ID NO: 2 was detected in the HLA-A0201 transgenic mouse-derived splenocytes, and IFNγ production specific to the object peptide shown by SEQ ID NO: 4 was detected in the HLA-A2402 transgenic mouse-derived splenocytes.

From the above, it was clarified that a compound represented by the formula (5) can induce CTL specific to the peptide shown by SEQ ID NO: 2 and CTL specific to the peptide shown by SEQ ID NO: 4. It was strongly suggested that the compound represented by the formula (5) undergoes cleavage of disulfide bond and appropriate trimming by ERAP-1 in mouse in vivo and is in fact processed into the peptides shown by SEQ ID NO: 2 and SEQ ID NO: 4.

That is, it was clarified that a compound represented by the formula (5), which is one embodiment of the compound of the present invention, is a conjugate wherein different two kinds of WT1 peptides form a composite via the disulfide bond shown in the formula (1), and is a WT1 cancer antigen peptide conjugate vaccine that in fact can induce different two kinds of CTLs in vivo.

Reference Examples 1-7

By a method similar to that in Example 2, respective peptides consisting of the amino acid sequences of SEQ ID NOs: 22, 24, 23, 2, 4, 6 and 5 were synthesized. Table 57 shows the results of mass spectrometry. Since SEQ ID NOs: 22, 24, 23, 2, 4, 6 and 5 are not the compound of the present invention, they are described as Reference Examples.

TABLE 57

| Ref. Ex. No. | amino acid sequence | sequence No. | mass spectrometry: LC-ESI/ MS m/z | mass spectrometry: Calculated |
|---|---|---|---|---|
| 1 | CNKRYFKLSHLQMHSRK | 22 | 1089.1 [M + 2H]$^+$ | 1089.3 |
| 2 | CNKRYFKLSHLQMHSRKHTG | 24 | 825.1 [M + 3H]$^+$ | 824.8 |
| 3 | CNKRYFKLSHLQMHSRKH | 23 | 772.4 [M + 3H]$^+$ | 772.2 |
| 4 | RMFPNAPYL | 2 | 1109.0 [M + H]$^+$ | 1109.3 |
| 5 | CYTWNQMNL | 4 | 1172.9 [M + H]$^+$ | 1173.4 |
| 6 | SLGEQQYSV | 6 | 1010.9 [M + H]$^+$ | 1011.1 |
| 7 | ALLPAVPSL | 5 | 881.0 [M + H]$^+$ | 881.1 |

Examples 6-9

By a method similar to that in Example 1, respective compounds (conjugates) represented by the formulas (3), (6), (7) and (8) were synthesized. Table 58 shows the results of mass spectrometry. (In each formula, the bond between C and C is a disulfide bond.)

TABLE 58

| Ex. No. | structural formula | formula No. | mass spectrometry: LC-ESI/ MS m/z | mass spectrometry: Calculated |
|---|---|---|---|---|
| 6 | CRMFPNAPYL<br>\|<br>CSLGEQQYSV | (3) | 1162.3 [M+2H]$^+$ | 1162.0 |
| 7 | CRMFPNAPYL<br>\|<br>CNKRYFKLSHLQMHSRKHTG | (6) | 1228.0 [M+3H]$^+$ | 1227.6 |
| 8 | CRMFPNAPYL<br>\|<br>CNKRYFKLSHLQMHSRKH | (7) | 705.8 [M+5H]$^+$ | 705.3 |
| 9 | CRMFPNAPYL<br>\|<br>CNKRYFKLSHLQMHSRK | (8) | 1129.8 [M+3H]$^+$ | 1129.2 |

Experimental Example 3

Measurement of Solubility

Step 1. Preparation of Isotonic Buffer 1. 75% aqueous solution of disodium hydrogen phosphate and 5.53% aqueous solution of citric acid were mixed, and respective buffers (pH 6.0 and 7.4) were prepared.

Step 2. Preparation of Test Solution

About 1 mg of a test product was measured, an isotonic buffer (0.5 mL) was added, and this was used as a test solution. The prepared test solution was shaken at room temperature for 90 min (shaking conditions: RECIPRO SHAKER SR-1N manufactured by TAITEC, Speed=8), centrifuged (15000 rpm, 5 min, room temperature), and the supernatant after centrifugation was used as a test solution.

Step 3. Preparation of Standard Solution

About 1 mg of the test product was accurately measured, dissolved in 0.1% TFA water/acetonitrile=1/1, made the total amount 10 mL, and this was used as a standard solution of the test product.

Step 4. Measurement of Concentration of Test Product

The standard solution of the test product and the test solution were analyzed by HPLC (analysis conditions described in Table 59), and the solubility of the test product was calculated from the peak area ratio of the standard solution.
   HPLC measurement conditions
   column: ChemcoPack Quicksorb (4.6 mmφ×150 mm, 5 μm)
   manufactured by Chemco Scientific Co., Ltd.
   mobile phase: SOLUTION A; 0.1% TFA water, SOLUTION B; 0.1% TFA acetonitrile solution
   column temperature: room temperature
   flow rate: 1 mL/min
   detection wavelength: UV 254 nm, 230 nm (2 wavelength detection)
   sample injection volume: 10 μL

TABLE 59

| gradient analysis conditions | | |
|---|---|---|
| time (min) | SOLUTION A (%) | SOLUTION B (%) |
| 0.00 | 80 | 20 |
| 10.00 | 0 | 100 |
| 15.00 | 0 | 100 |
| 15.01 | 80 | 20 |
| 25.00 | 80 | 20 |
| 25.01 | STOP | |

The peptides synthesized in Reference Examples 1-2 and 4-7 and the compounds (conjugates) synthesized in Examples 1, 7 and 9 were subjected to the above-mentioned solubility measurement. Each solubility is shown in Table 60.

TABLE 60

| Reference Example No. or Example No. | amino acid sequence or structural formula | SEQ ID NO: or formula No. | pH 6.0 (mg/mL) | pH 7.4 (mg/mL) |
|---|---|---|---|---|
| Reference Example 6 | SLGEQQYSV | SEQ ID NO: 6 | >1.0 | >1.0 |
| Reference Example 7 | ALLPAVPSL | SEQ ID NO: 5 | >1.0 | >1.0 |
| Reference Example 2 | CNKRYFKLSHLQMHSRKHTG | SEQ ID NO: 24 | >1.0 | 0.556 |
| Reference Example 1 | CNKRYFKLSHLQMHSRK | SEQ ID NO: 22 | >1.0 | 0.931 |
| Example 7 | CRMFPNAPYL<br>\|<br>CNKRYFKLSHLQMHSRKHTG | formula (6) | >1.0 | 0.279 |
| Example 9 | CRMFPNAPYL<br>\|<br>CNKRYFKLSHLQMHSRK | formula (8) | >1.0 | 0.789 |
| Reference Example 4 | RMFPNAPYL | SEQ ID NO: 2 | >1.0 | >1.0 |
| Reference Example 5 | CYTWNQMNL | SEQ ID NO: 4 | 0.106 | 0.167 |
| Example 1 | CRMFPNAPYL<br>\|<br>CYTWNQMNL | formula (5) | 0.511 | 0.200 |

Experimental Example 4

Evaluation of In Vivo CTL Induction Ability Using HLA-A0201 Transgenic Mouse The compound represented by the formula (3) synthesized in Example 6 was evaluated for the CTL induction ability by an in vivo CTL induction test using HLA-A0201 transgenic mouse. The compound represented by the formula (3):

(3)

wherein the bond between C and C is a disulfide bond, is, in particular, a compound of the aforementioned formula (1), wherein cancer antigen peptide A is RMFPNAPYL (SEQ ID NO: 2) and cancer antigen peptide B is SLGEQQYSV (SEQ ID NO: 6). RMFPNAPYL (SEQ ID NO: 2) and SLGEQQYSV (SEQ ID NO: 6) are a HLA-A0201-restricted WT1 peptides.

The HLA-A0201 transgenic mouse is as described in Experimental Example 2.

Whether the administration of a compound represented by the formula (3) results in the induction of CTL specific to the object peptide (SEQ ID NO: 2, 6) was judged based on the measurement of IFNγ production by re-stimulation, with the peptide (SEQ ID NO: 2, 6), of the splenocyte derived from the above-mentioned mouse administered with a compound represented by the formula (3).

Specifically, a compound represented by the formula (3) was dissolved in water for injection at 10 mg/mL, and emulsified by mixing with an equal amount of incomplete Freund's adjuvant (IFA). The emulsified compound was intradermally administered to 2 sites at the base of tail of a mouse at 500 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.75 \times 10^6$ cells/well on the blocked ELISPOT plate. Peptide (SEQ ID NO: 2, 6) was dissolved in DMSO at 40 mg/mL, and further diluted with RPMI1640 medium containing 10% FBS to 40 μg/mL. The diluted peptide (SEQ ID NO: 2, 6) was added to the HLA-A0201 transgenic mouse-derived splenocytes at a final concentration of 10 μg/mL. The splenocytes added with the peptide were cultured for 20 hr at 37° C., 5%

$CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 4:
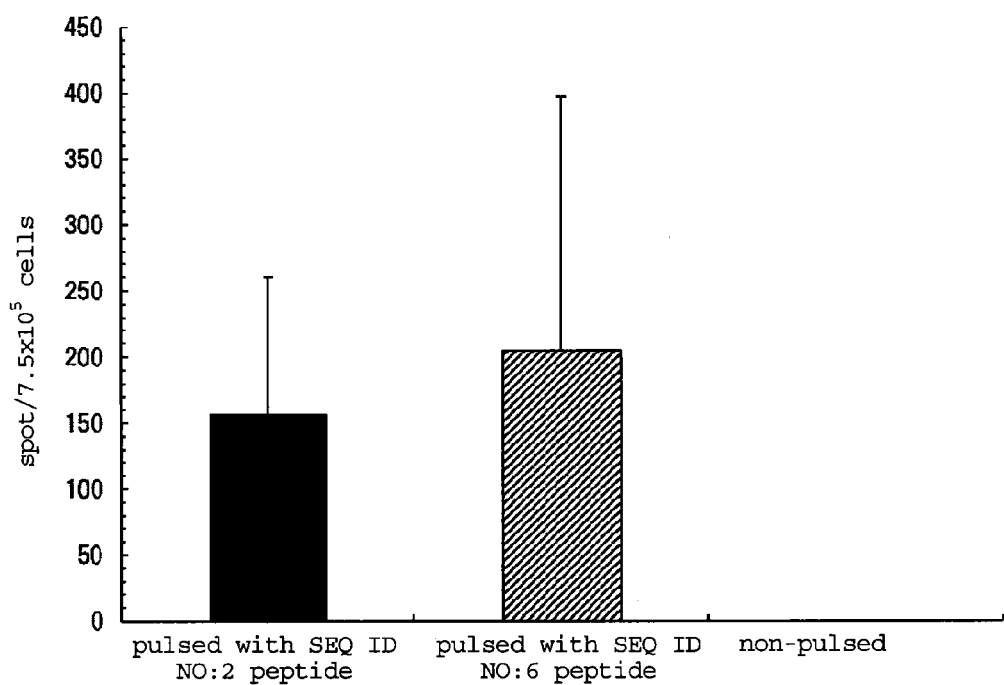
FIG. 4 is a Figure showing the test results of Experimental Example 4 as to the in vivo CTL induction ability of a compound represented by the formula (3) synthesized in Example 6, by IFNγ ELISPOT assay using HLA-A0201 transgenic mouse.

The results of IFNγ ELISPOT assay using the HLA-A0201 transgenic mouse are shown in FIG. 4.

In FIG. 4, the vertical axis shows the number of cells that reacted in the plated cells. In FIG. 4, the black bar and the shaded bar show the results of culture of HLA-A0201 transgenic mouse-derived splenocytes while being pulsed with each peptide shown by SEQ ID NO: 2, 6, and the white bar show the results of culture without pulsing. That is, the difference in the values of the black or shaded bar and the white bar shows the number of peptide-specific CTL, and that the administration of a compound represented by the formula (3) resulted in the induction of CTL specific to each peptide shown by SEQ ID NOs: 2, 6 in vivo in the mouse. In FIG. 4, the value of the white bar is not detected. This means that the splenocytes of HLA-A0201 transgenic mice did not react at all in the absence of pulsing with the object peptide. As a result of this test, IFNγ production specific to the peptide shown by SEQ ID NO: 2, 6 was detected in the HLA-A0201 transgenic mouse-derived splenocytes.

From the above, it was clarified that a compound represented by the formula (3) can induce CTL specific to the peptide shown by SEQ ID NO: 2, 6. It was strongly suggested that the compound represented by the formula (3) undergoes cleavage of disulfide bond and appropriate trimming by ERAP-1 in mouse in vivo and is in fact processed into the peptides shown by SEQ ID NO: 2 and 6. That is, it was clarified that a compound represented by the formula (3), which is one embodiment of the compound of the present invention, is a conjugate wherein different two kinds of peptides form a composite via the disulfide bond shown in the formula (1), and is a WT1 cancer antigen peptide conjugate vaccine that in fact can induce different two kinds of CTLs in vivo.

Experimental Example 5

Evaluation of In Vivo CTL Induction Ability Using HLA-A0201 Transgenic Mouse

The compound represented by the formula (6) synthesized in Example 7 was evaluated for the CTL induction ability by an in vivo CTL induction test using HLA-A0201 transgenic mouse. The compound represented by the formula (6):

(6)

wherein the bond between C and C is a disulfide bond, is, in particular, a compound of the aforementioned formula (1), wherein cancer antigen peptide A is RMFPNAPYL (SEQ ID NO: 2) and cancer antigen peptide C is CNKRYFKLSHLQMHSRKHTG (SEQ ID NO: 24). RMFPNAPYL (SEQ ID NO: 2) is a HLA-A0201-restricted WT1 peptide, and CNKRYFKLSHLQMHSRKHTG (SEQ ID NO: 24) is an MHC class II-restricted WT1 peptide (namely, helper peptide).

The HLA-A0201 transgenic mouse is as described in Experimental Example 2. Using this mouse, HLA-A02 positive peptide capable of inducing CTL in human can be selected, as well as the CTL induction enhancing activity of helper peptide capable of inducing helper T cell by binding to human HLA-DRB1*0101 can be evaluated.

Whether the administration of a compound represented by the formula (6) results in the induction of CTL specific to the object peptide (SEQ ID NO: 2) and cells reactive with helper peptide (SEQ ID NO: 24) was judged based on the measurement of IFNγ production by re-stimulation, with the peptide (SEQ ID NO: 2, 24), of the splenocyte derived from the above-mentioned mouse administered with a compound represented by the formula (6). In addition, the splenocytes derived from the above-mentioned mouse administered with a compound represented by the formula (6) and the splenocytes derived from the above-mentioned mouse administered with a compound represented by SEQ ID NO: 2 were re-stimulated with the peptide (SEQ ID NO: 2), and the IFNγ-producing cell numbers were compared.

Specifically, a peptide represented by SEQ ID NO: 2 was dissolved in water for injection at 6 mg/mL, and emulsified by mixing with an equal amount of incomplete Freund's adjuvant (IFA). The emulsified peptide was intradermally administered to 2 sites at the base of tail of a mouse at 150 μg/site. A compound represented by the formula (6) was dissolved in water for injection (19.8 mg/mL), and emulsified by mixing with an equal amount of incomplete Freund's adjuvant (IFA). The emulsified compound was intradermally administered to 2 sites at the base of tail of a mouse at 495 fig/site. The mole number of the peptide of SEQ ID NO: 2 contained in the dose of the compound represented by the formula (6) per one mouse was adjusted to be equal to that of the peptide of SEQ ID NO: 2 contained in the dose per mouse. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ is cells/well or $0.5 \times 10^6$ cells/well on the blocked ELISPOT plate. Peptide (SEQ ID NO: 2, 24) was dissolved in DMSO at 40 mg/mL, and further diluted with RPMI1640 medium containing 10% FBS to 40 μg/mL. The diluted peptide (SEQ ID NO: 2, 24) was added to the HLA-A0201 transgenic mouse-derived splenocytes at a final concentration of 10 μg/mL. The splenocytes added with the peptide were cultured for 20 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 5:
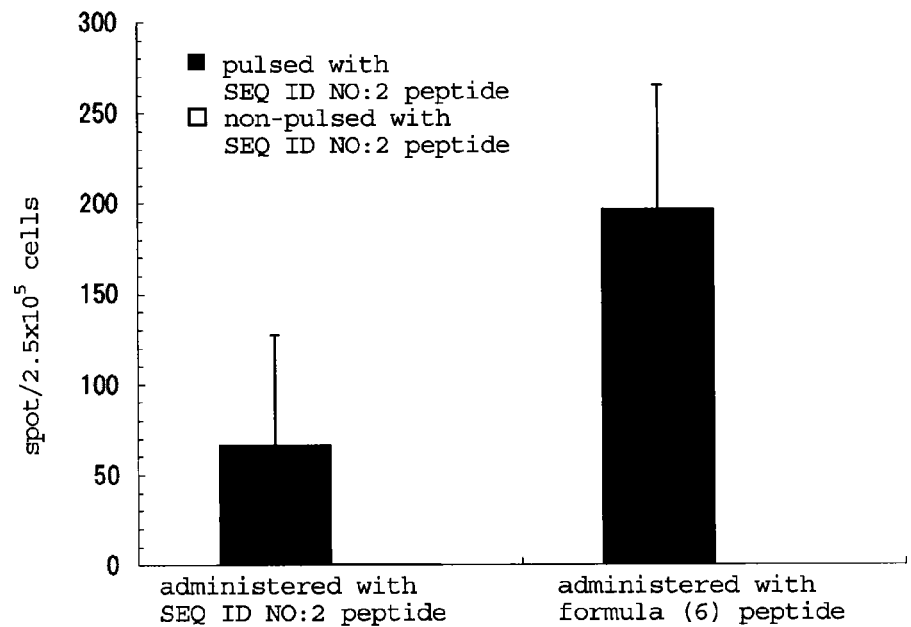
FIG. 5 is a Figure showing the test results of Experimental Example 5 as to the ability of a compound represented by the formula (6) synthesized in Example 7 to induce cells reactive with peptide shown by SEQ ID NO: 24 in vivo, by IFNγ ELISPOT assay using HLA-A0201 transgenic mouse in the pulsed or non-pulsed state with peptide of SEQ ID NO: 24.
Figure 6:
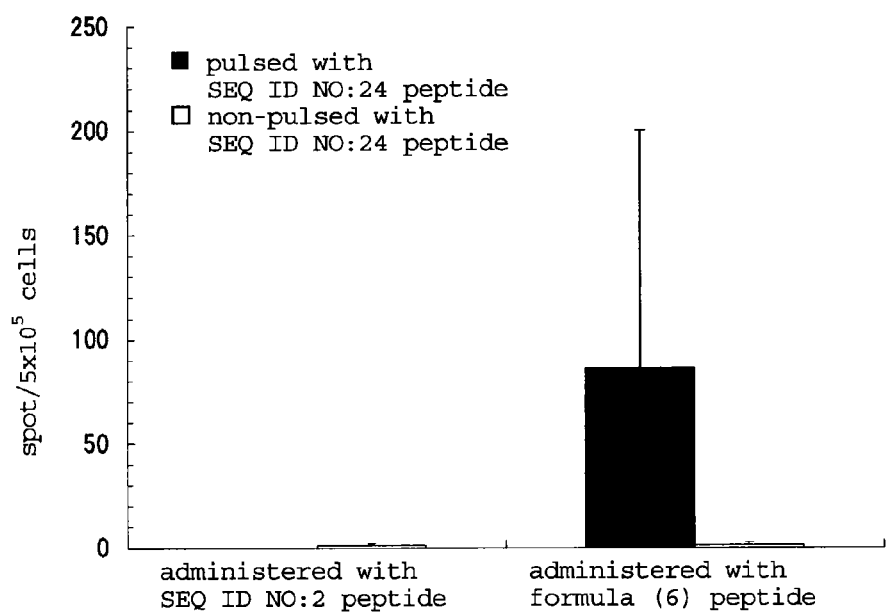
FIG. 6 is a Figure showing the test results of Experimental Example 5 as to the ability of a compound represented by the formula (6) synthesized in Example 7 to induce cells reactive with peptide shown by SEQ ID NO: 24 in vivo, by IFNγ ELISPOT assay using HLA-A0201 transgenic mouse in the pulsed or non-pulsed state with peptide of SEQ ID NO: 24.

The results of IFNγ ELISPOT assay using the HLA-A0201 transgenic mouse are shown in FIGS. 5 and 6.

In FIGS. 5 and 6, the vertical axis shows the number of cells that reacted in the plated cells, and the horizontal axis shows compound or peptide administered to the mouse. In FIG. 5, the black bar shows the results of culture of HLA-A0201 transgenic mouse-derived splenocytes while being pulsed with the peptide shown by SEQ ID NO: 2, and the white bar show the results of culture without pulsing. That is, the difference in the values of the black bar and the white bar shows the number of peptide-specific CTL, and that the administration of the peptide shown by SEQ ID NO: 2 or a compound represented by the formula (6) resulted in the induction of CTL specific to the peptide shown by SEQ ID NO: 2 in vivo in the mouse. In FIG. 5, the value of the white bar is not detected. This means that the splenocytes of HLA-A0201 transgenic mice did not react at all in the absence of pulsing with the object peptide. As a result of this test, IFNγ production specific to the peptide shown by SEQ ID NO: 2 was detected in the HLA-A0201 transgenic mouse-derived splenocytes. Moreover, in FIG. 5, the number of IFNγ-producing cells specific to the peptide shown by SEQ ID NO: 2, which were induced by the administration of a compound represented by the formula (6), was higher than that of the peptide-specific IFNγ-producing cells induced by the administration of the peptide shown by SEQ ID NO: 2.

In FIG. 6, furthermore, the black bar shows the results of culture of HLA-A0201 transgenic mouse-derived splenocytes while being pulsed with peptide shown by SEQ ID NO: 24, and the white bar show the results of culture without pulsing. That is, the difference in the values of the black bar and the white bar shows the number of peptide-reactive cells, and that the administration of a compound represented by the formula (6) resulted in the induction of cells reactive with the helper peptide shown by SEQ ID NO: 24 in vivo in the mouse, and administration of a compound represented by SEQ ID NO: 2 did not induce cells reactive with the peptide shown by SEQ ID NO: 24 in vivo in the mouse. In FIG. 6, the value of the white bar is not detected. This means that the splenocytes of HLA-A0201 transgenic mice did not react at all in the absence of pulsing with the object peptide.

From the above, it was clarified that a compound represented by the formula (6) can induce CTL specific to the peptide shown by SEQ ID NO: 2 and cells reactive with the helper peptide shown by SEQ ID NO: 24. It was strongly suggested that the compound represented by the formula (6) undergoes cleavage of disulfide bond and appropriate trimming by ERAP-1 in mouse in vivo and is in fact processed into the peptides shown by SEQ ID NO: 2 and 24. It was assumed that the induction of the cell reactive with the helper peptide shown by SEQ ID NO: 24 produced from a compound represented by the formula (6) enhanced induction of CTL specific to the peptide shown by SEQ ID NO: 2, and many IFNγ-producing cells specific to the peptide shown by SEQ ID NO: 2 were found, as compared to the administration of the peptide shown by SEQ ID NO: 2.

That is, it was clarified that a compound represented by the formula (6), which is one embodiment of the compound of the present invention, is a conjugate wherein two different kinds of peptides form a composite via the disulfide bond shown in the formula (1), and is a WT1 cancer antigen peptide conjugate vaccine that in fact can induce CTLs and helper peptide reactive cells in vivo.

Experimental Example 6

Evaluation of In Vivo CTL Induction Ability Using HLA-A0201 Transgenic Mouse

The compound represented by the formula (8) synthesized in Example 9 was evaluated for the CTL induction ability by an in vivo CTL induction test using HLA-A0201 transgenic mouse. The compound represented by the formula (8):

(8)

wherein the bond between C and C is a disulfide bond, is, in particular, a compound of the aforementioned formula (1), wherein cancer antigen peptide A is RMFPNAPYL (SEQ ID NO: 2) and cancer antigen peptide C is CNKRYFKLSHLQMHSRK (SEQ ID NO: 22). RMFPNAPYL (SEQ ID NO: 2) is a HLA-A0201-restricted WT1 peptide, and CNKRYFKLSHLQMHSRK (SEQ ID NO: 22) is an MHC class II-restricted WT1 peptide (namely, helper peptide).

The HLA-A0201 transgenic mouse is as described in Experimental Examples 2 and 5.

Whether the administration of a compound represented by the formula (8) results in the induction of CTL specific to the object peptide (SEQ ID NO: 2) and cells reactive with helper peptide (SEQ ID NO: 22) reactive cell was judged based on the measurement of IFNγ production by re-stimulation, with the peptide (SEQ ID NO: 2, 22), of the splenocyte derived from the above-mentioned mouse administered with a compound represented by the formula (8). In addition, the splenocytes derived from the above-mentioned mouse administered with a compound represented by the formula (8) and the splenocytes derived from the above-mentioned mouse administered with a compound represented by SEQ ID NO: 2 were re-stimulated with the peptide (SEQ ID NO: 2), and the IFNγ-producing cell numbers were compared.

Specifically, a peptide represented by SEQ ID NO: 2 was dissolved in water for injection at 6 mg/mL, and emulsified by mixing with an equal amount of incomplete Freund's adjuvant (IFA). The emulsified peptide was intradermally administered to 2 sites at the base of tail of a mouse at 150 µg/site. A compound represented by the formula (8) was dissolved in water for injection (18 mg/mL), and emulsified by mixing with an equal amount of incomplete Freund's adjuvant (IFA). The emulsified compound was intradermally administered to 2 sites at the base of tail of a mouse at 450 lag/site. The mole number of the peptide of SEQ ID NO: 2 contained in the dose of the compound represented by the formula (8) per one mouse was adjusted to be equal to that of the peptide of SEQ ID NO: 2 contained in the dose per mouse. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well or $0.5 \times 10^6$ cells/well on the blocked ELISPOT plate. Peptide (SEQ ID NO: 2, 22) was dissolved in DMSO at 40 mg/mL, and further diluted with RPMI1640 medium containing 10% FBS to 40 µg/mL. The diluted peptide (SEQ ID NO: 2, 22) was added to the HLA-A0201 transgenic mouse-derived splenocytes at a final concentration of 10 µg/mL. The splenocytes added with the peptide were cultured for 20 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 7:
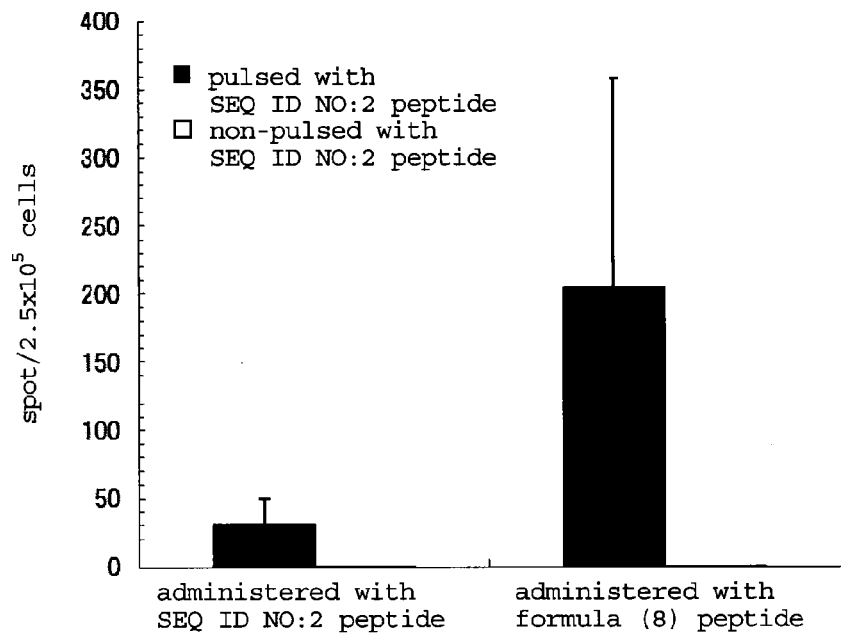
FIG. 7 is a Figure showing the test results of Experimental Example 6 as to the in vivo CTL induction ability of a compound represented by the formula (8) synthesized in Example 9 in the pulsed or non-pulsed state with peptide of SEQ ID NO: 2, by IFNγ ELISPOT assay using HLA-A0201 transgenic mouse.
Figure 8:
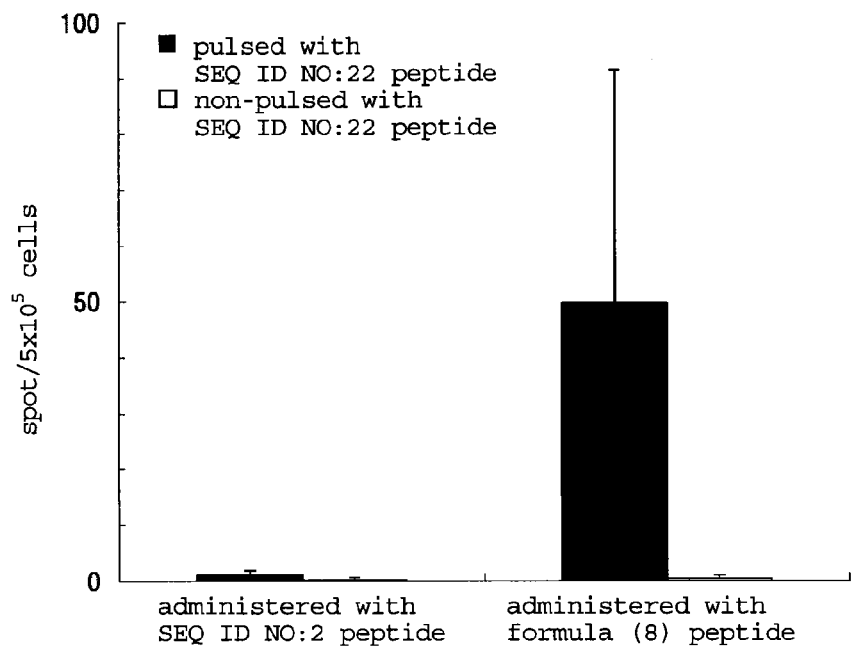
FIG. 8 is a Figure showing the test results of Experimental Example 6 as to the ability of a compound represented by the formula (8) synthesized in Example 9 to induce cells reactive with peptide shown by SEQ ID NO: 22 in vivo, by IFNγ ELISPOT assay using HLA-A0201 transgenic mouse in the pulsed or non-pulsed state with peptide of SEQ ID NO: 22.

The results of IFNγ ELISPOT assay using the HLA-A0201 transgenic mouse are shown in FIGS. 7 and 8.

In FIGS. 7 and 8, the vertical axis shows the number of cells that reacted in the plated cells, and the horizontal axis shows compound or peptide administered to the mouse. In FIG. 7, the black bar shows the results of culture of HLA-A0201 transgenic mouse-derived splenocytes while being pulsed with the peptide shown by SEQ ID NO: 2, and the white bar shows the results of culture without pulsing. That is, the difference in the values of the black bar and the white bar shows the number of peptide-specific CTL, and that the administration of the peptide shown by SEQ ID NO: 2 or a compound represented by the formula (8) resulted in the induction of CTL specific to the peptide shown by SEQ ID NO: 2 in vivo in the mouse. In FIG. 7, the value of the white bar is not detected. This means that the splenocytes of HLA-A0201 transgenic mice did not react at all in the absence of pulsing with the object peptide. As a result of this test, IFNγ production specific to the peptide shown by SEQ ID NO: 2 was detected in the HLA-A0201 transgenic mouse-derived splenocytes. Moreover, in FIG. 7, the number of IFNγ-producing cells specific to the peptide shown by SEQ ID NO: 2, which were induced by the administration of a compound represented by the formula (8), was higher than that of the peptide-specific IFNγ-producing cells induced by the administration of the peptide shown by SEQ ID NO: 2.

In FIG. 8, furthermore, the black bar shows the results of culture of HLA-A0201 transgenic mouse-derived splenocytes is while being pulsed with peptide shown by SEQ ID NO: 22, and the white bar shows the results of culture without pulsing. That is, the difference in the values of the black bar and the white bar shows the number of peptide-reactive cells, and that the administration of a compound represented by the formula (8) resulted in the induction of cells reactive with the helper peptide shown by SEQ ID NO: 22 in vivo in the mouse, and administration of a peptide represented by SEQ ID NO: 2 did not induce cells reactive with the peptide shown by SEQ ID NO: 22 in vivo in the mouse. In FIG. 8, the value of the white bar is not detected. This means that the splenocytes of HLA-A0201 transgenic mice did not react at all in the absence of pulsing with the object peptide.

From the above, it was clarified that a compound represented by the formula (8) can induce CTL specific to the peptide shown by SEQ ID NO: 2 and cells reactive with the helper peptide shown by SEQ ID NO: 22. It was strongly suggested that the compound represented by the formula (8) undergoes cleavage of disulfide bond and appropriate trimming by ERAP-1 in mouse in vivo and is in fact processed into the peptides shown by SEQ ID NO: 2 and 22. It was assumed that the induction of the cell reactive with the helper peptide shown by SEQ ID NO: 22 produced from a compound represented by the formula (8) enhanced induction of CTL specific to the peptide shown by SEQ ID NO: 2, and many IFNγ-producing cells specific to the peptide shown by SEQ ID NO: 2 were found, as compared to the administration of the compound shown by SEQ ID NO: 2.

That is, it was clarified that a compound represented by the formula (8), which is one embodiment of the compound of the present invention, is a conjugate wherein two different kinds of peptides form a composite via the disulfide bond shown in the formula (1), and is a WT1 cancer antigen peptide conjugate vaccine that in fact can induce CTLs and helper peptide reactive cells in vivo.

Example 10

By a method similar to that in Example 1, respective compounds (conjugates) represented by the formula (9) were synthesized. Table 61 shows the results of mass spectrometry. (In each formula, the bond between C and C is a disulfide bond.)

TABLE 61

| Ex. No. | structural formula | formula No. | mass spectrometry: LC-ESI/MS m/Z | mass spectrometry: Calculated |
|---|---|---|---|---|
| 10 | CALLPAVPSL<br>\|<br>CNKRYFKLSHLQMHSRKHTG | 9 | 1151.9 $[M + 3H]^{3+}$ | 1152.0 |

Reference Example 8-9

By a method similar to that in Example 2, peptides consisting of the amino acid sequences shown by SEQ ID NOs: 238-239 were synthesized. The results of mass spectrometry are shown in Table 62. Since the peptides described in the Table are not the compound of the present invention, they are indicated as Reference Examples.

TABLE 62

| Ref. Ex. No. | amino acid sequence | SEQ ID NO: | mass spectrometry: LC-ESI/MS m/Z | mass spectrometry: Calculated |
|---|---|---|---|---|
| 8 | RMFPNAPYLCYTWNQMNL | 238 | 1132.2 $[M + 2H]^{2+}$ | 1132.3 |
| 9 | CYTWNQMNLRMFPNAPYL | 239 | 1133.0 $[M + 2H]^{2+}$ | 1132.3 |

Reference Examples 10-11

By a method similar to that in Example 2, peptides consisting of the amino acid sequences shown by SEQ ID NOs: 240-241 were synthesized. The results of mass spectrometry are shown in Table 63. Since the peptides described in the Table are not the compound of the present invention, they are indicated as Reference Examples.

TABLE 63

| Ref. Ex. No. | amino acid sequence | SEQ ID NO: | mass spectrometry: LC-ESI/MS m/ | mass spectrometry: Calculated |
|---|---|---|---|---|
| 10 | RMFPNAPYLGGGGGGCYTWNQMNL | 240 | 1303.7 $[M + 2H]^{2+}$ | 1303.5 |
| 11 | CYTWNQMNGGGGGGRMFPNAPYL | 241 | 1303.0 $[M + 2H]^{2+}$ | 1303.5 |

The peptides shown in Table 63 were synthesized by referring to the non-patent document, Cancer Science January 2012, Vol. 103, no. 1, 150-153.

Experimental Example 7

Stability Test of Conjugate and Cocktail Vaccine

Step 1

Conjugate (formula No.: (6)) (2.4 mg) was dissolved in 120 μL of water for injection and preserved under shading at room temperature.

Step 2

As a cocktail vaccine, the peptide shown by SEQ ID NO: 2 (1.1 mg) was dissolved in 180 μL of water for injection, 123 μL thereof was used to dissolve the peptide shown by SEQ ID NO: 24 (1.3 mg), and the solution was preserved under shading at room temperature.

Step 3

The solutions (2.5 μL) obtained in step 1 and step 2 were diluted with water for injection (50 μL) and subjected to HPLC analysis (analysis conditions are shown below), and the content percentage of the conjugate and peptide in the aqueous solution were measured with the area value immediately after the start of the preservation as 100%. The content percentage of the conjugate is shown in Table 64, and that of each peptide in the cocktail vaccine is shown in Table 65.

analysis conditions
pump: UFLC manufactured by Shimadzu
column: Kinetex 2.6u C18 100A 3.0 mm i.d.×75 mm
mobile phase: SOLUTION A; 0.1% TFA water, SOLUTION B; 0.1% TFA acetonitrile solution
column temperature: 40° C.
flow rate: 1 mL/min
detection wavelength: UV 220, 254 nm (2 wavelengths detection)
sample injection volume: 10 μL

TABLE 64

| elapsed time | formula No. (6) content percentage (%) |
| --- | --- |
| 1 day | 107 |
| 2 weeks | 96 |

TABLE 65

| elapsed time | SEQ ID NO: 2 content percentage (%) | SEQ ID NO: 24 content percentage (%) |
| --- | --- | --- |
| 1 day | 97 | 65 |
| 1 week | 99 | 9 |
| 2 weeks | 94 | 6 |

In Experimental Example 7, the conjugate represented by formula No. (6) contained 96% of the compound represented by the formula (6) at the time point of 2 weeks from the solution preparation. In contrast, in a mixed solution of SEQ ID NO: 2 and SEQ ID NO: 24, which is a cocktail vaccine, the content percentage of SEQ ID NO: 24 decreased to 65% at the time point of 1 day elapse, and to 6% 2 weeks later. These results show that the conjugate preserved in the form of an aqueous solution is was stabler than cocktail vaccine preserved under the same conditions.

Experimental Example 8

Evaluation of In Vivo CTL Induction Ability Using HLA-A0201 Transgenic Mouse

The compound represented by the formula (7) synthesized in Example 8 was evaluated for the CTL induction ability by an in vivo CTL induction test using HLA-A0201 transgenic mouse. The compound represented by the formula (7):

wherein the bond between C and C is a disulfide bond, is, in particular, a compound of the aforementioned formula (1), wherein cancer antigen peptide A is RMFPNAPYL (SEQ ID NO: 2) and cancer antigen peptide C is CNKRYFKLSHLQMHSRKH (SEQ ID NO: 23). RMFPNAPYL (SEQ ID NO: 2) is a HLA-A0201-restricted WT1 peptide, and CNKRYFKLSHLQMHSRKH (SEQ ID NO: 23) is an MHC class II-restricted WT1 peptide (namely, helper peptide).

The HLA-A0201 transgenic mouse is as described in Experimental Examples 2 and 5.

Whether the administration of a compound represented by the formula (7) results in the induction of CTL specific to the object peptide (SEQ ID NO: 2) and cells reactive with helper peptide (SEQ ID NO: 23) was judged based on the measurement of IFNγ production by re-stimulation, with the peptide (SEQ ID NO: 2, 23), of the splenocyte derived from the above-mentioned mouse administered with a compound represented by the formula (7). In addition, the splenocytes derived from the above-mentioned mouse administered with a compound represented by the formula (7) and the splenocytes derived from the above-mentioned mouse administered with a compound represented by SEQ ID NO: 2 were re-stimulated with the peptide (SEQ ID NO: 2), and the IFNγ-producing cell numbers were compared.

Specifically, a peptide represented by SEQ ID NO: 2 was dissolved in water for injection at 6 mg/mL, and emulsified by mixing with an equal amount of incomplete Freund's adjuvant (IFA). The emulsified peptide was intradermally administered to 2 sites at the base of tail of a mouse at 150 lag/site. A compound represented by the formula (7) was dissolved in water for injection (19 mg/mL), and emulsified by mixing with an equal amount of incomplete Freund's adjuvant (IFA). The emulsified compound was intradermally administered to 2 sites at the base of tail of a mouse at 475 μg/site. The mole number of the peptide of SEQ ID NO: 2 contained in the dose of the compound represented by the formula (7) per one mouse was adjusted to be equal to that of the peptide of SEQ ID NO: 2 contained in the dose per mouse. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well or $0.5 \times 10^6$ cells/well on the blocked ELISPOT plate. Peptide (SEQ ID NO: 2, 23) was dissolved in DMSO at 40 mg/mL, and further diluted with RPMI1640 medium containing 10% FBS to 40 μg/mL. The diluted peptide (SEQ ID NO: 2, 23) was added to the HLA-A0201 transgenic mouse-derived splenocytes at a final concentration of 10 μg/mL. The splenocytes added with the peptide were cultured for 17 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 9:
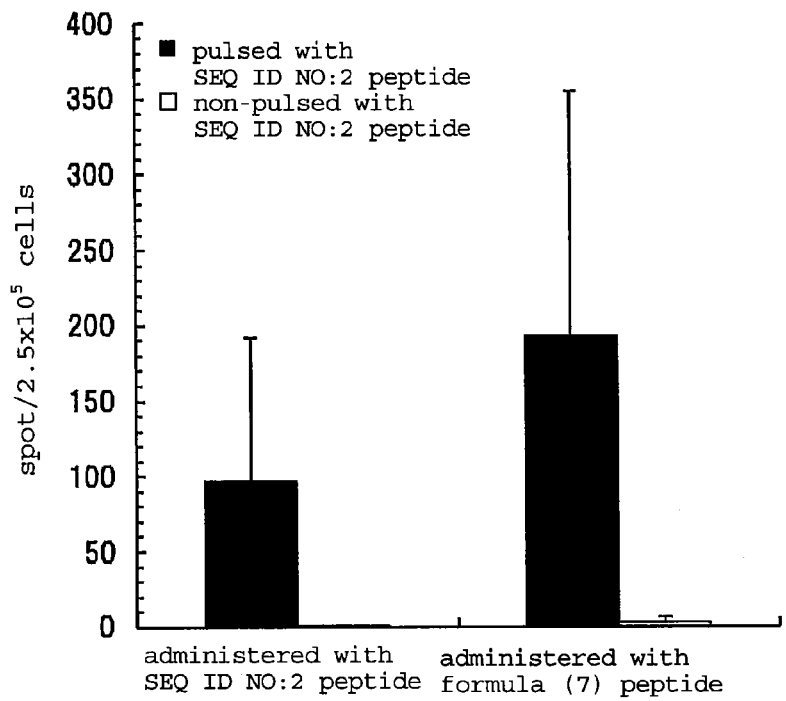
FIG. 9 is a Figure showing the test results of Experimental Example 8 as to the in vivo CTL induction ability of a compound represented by the formula (7) synthesized in Example 8 in the pulsed or non-pulsed state with peptide of SEQ ID NO: 2, by IFNγ ELISPOT assay using HLA-A0201 transgenic mouse.
Figure 10:
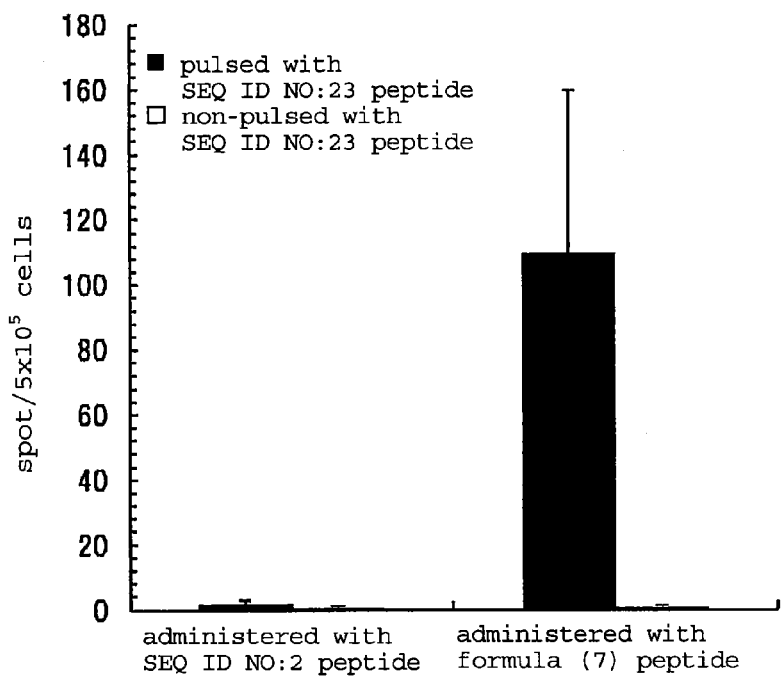
FIG. 10 is a Figure showing the test results of Experimental Example 8 as to the ability of a compound represented by the formula (7) synthesized in Example 8 to induce cells reactive with peptide shown by SEQ ID NO: 23 in vivo, by IFNγ ELISPOT assay using HLA-A0201 transgenic mouse in the pulsed or non-pulsed state with peptide of SEQ ID NO: 23.

The results of IFNγ ELISPOT assay using the HLA-A0201 transgenic mouse are shown in FIGS. 9 and 10. In FIGS. 9 and 10, the vertical axis shows the number of cells that reacted in the plated cells, and the horizontal axis shows compound or peptide administered to the mouse. In FIG. 9, the black bar shows the results of culture of HLA-A0201 transgenic mouse-derived splenocytes while being pulsed with the peptide shown by SEQ ID NO: 2, and the white bar shows the results of culture without pulsing. That is, the difference in the values of the black bar and the white bar shows the number of peptide-specific CTL, and that the administration of the peptide shown by SEQ ID NO: 2 or a compound represented by the formula (7) resulted in the induction of CTL specific to the peptide shown by SEQ ID NO: 2 in vivo in the mouse. In FIG. 9, the value of the white bar is not detected. This means that the splenocytes of HLA-A0201 transgenic mice did not react at all in the absence of pulsing with the object peptide. As a result of this test, IFNγ production specific to the peptide shown by SEQ ID NO: 2 was detected in the HLA-A0201 transgenic mouse-derived splenocytes. Moreover, in FIG. 9, the number of IFNγ-producing cells specific to the peptide shown by SEQ ID NO: 2, which were induced by the administration of a compound represented by the formula (7), was higher than that of the peptide-specific IFNγ-producing cells induced by the administration of the peptide shown by SEQ ID NO: 2.

In FIG. 10, furthermore, the black bar shows the results of culture of HLA-A0201 transgenic mouse-derived splenocytes while being pulsed with peptide shown by SEQ ID NO: 23, and the white bar shows the results of culture without pulsing. That is, the difference in the values of the black bar and the white bar shows the number of peptide-reactive cells, and that the administration of a compound represented by the formula (7) resulted in the induction of cells reactive with the helper peptide shown by SEQ ID NO: 23 in vivo in the mouse, and administration of a peptide represented by SEQ ID NO: 2 did not induce cells reactive with the peptide shown by SEQ ID NO: 23 in vivo in the mouse. In FIG. 10, the value of the white bar is not detected. This means that the splenocytes of HLA-A0201 transgenic mice did not react at all in the absence of pulsing with the object peptide.

From the above, it was clarified that a compound represented by the formula (7) can induce CTL specific to the peptide shown by SEQ ID NO: 2 and cells reactive with the helper peptide shown by SEQ ID NO: 23. It was strongly suggested that the compound represented by the formula (7) undergoes cleavage of disulfide bond and appropriate trimming by ERAP-1 in mouse in vivo and is in fact processed into the peptides shown by SEQ ID NO: 2 and 23. It was assumed that the induction of the cell reactive with the helper peptide shown by SEQ ID NO: 23 produced from a compound represented by the formula (7) enhanced induction of CTL specific to the peptide shown by SEQ ID NO: 2, and many IFNγ-producing cells specific to the peptide shown by SEQ ID NO: 2 were found, as compared to the administration of the compound shown by SEQ ID NO: 2.

That is, it was clarified that a compound represented by the formula (7), which is one embodiment of the compound of the present invention, is a conjugate wherein two different kinds of peptides form a composite via the disulfide bond shown in the formula (1), and is a WT1 cancer antigen peptide conjugate vaccine that in fact can induce CTLs and helper peptide reactive cells in vivo.

Experimental Example 9

Evaluation of In Vivo CTL Induction Ability Using HLA-A0201 Transgenic Mouse

The compound represented by the formula (9) synthesized in Example 10 was evaluated for the CTL induction ability by an in vivo CTL induction test using HLA-A0201 transgenic mouse. The compound represented by the formula (9):

wherein the bond between C and C is a disulfide bond, is, in particular, a compound of the aforementioned formula (1), wherein cancer antigen peptide A is ALLPAVPSL (SEQ ID NO: 5) and cancer antigen peptide C is CNKRYFKLSHLQMHSRKHG (SEQ ID NO: 24). ALLPAVPSL (SEQ ID NO: 5) is a HLA-A0201 and HLA-A2402-restricted WT1 peptide, and CNKRYFKLSHLQMHSRKHG (SEQ ID NO: 24) is an MHC class II-restricted WT1 peptide (namely, helper peptide).

The HLA-A0201 transgenic mouse is as described in Experimental Examples 2 and 5.

Whether the administration of a compound represented by the formula (9) results in the induction of CTL specific to the object peptide (SEQ ID NO: 5) and cells reactive with helper peptide (SEQ ID NO: 24) was judged based on the measurement of IFNγ production by re-stimulation, with the peptide (SEQ ID NO: 5, 24), of the splenocyte derived from the above-mentioned mouse administered with a compound represented by the formula (9). In addition, the splenocytes derived from the above-mentioned mouse administered with a compound represented by the formula (9) and the splenocytes derived from the above-mentioned mouse administered with a compound represented by SEQ ID NO: 5 were re-stimulated with the peptide (SEQ ID NO: 5), and the IFNγ-producing cell numbers were compared.

Specifically, a peptide represented by SEQ ID NO: 5 was dissolved in water for injection at 6 mg/mL, and emulsified by mixing with an equal amount of incomplete Freund's adjuvant (IFA). The emulsified peptide was intradermally administered to 2 sites at the base of tail of a mouse at 150 μg/site. A compound represented by the formula (9) was dissolved in water for injection (23.6 mg/mL), and emulsified by mixing with an equal amount of incomplete Freund's adjuvant (IFA). The emulsified compound was intradermally administered to 2 sites at the base of tail of a mouse at 590 μg/site. The mole number of the peptide of SEQ ID NO: 5 contained in the dose of the compound represented by the formula (9) per one mouse was adjusted to be equal to that of the peptide of SEQ ID NO: 5 contained in the dose per mouse. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at 0.25×10⁶ cells/well or 0.75×10⁶ cells/well on the blocked ELISPOT plate. Peptide (SEQ ID NO: 5, 24) was dissolved in DMSO at 40 mg/mL, and further diluted with RPMI1640 medium containing 10% FBS to 40 μg/mL. The diluted peptide (SEQ ID NO: 5, 24) was added to the HLA-A0201 transgenic mouse-derived splenocytes at a final concentration of 10 μg/mL. The splenocytes added with the peptide were cultured for 17 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 11:
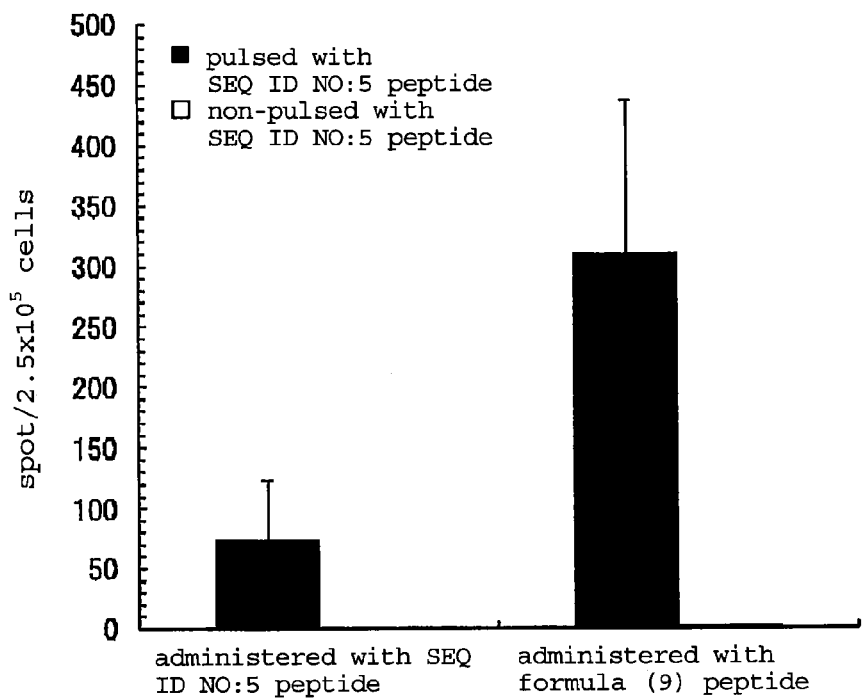
FIG. 11 is a Figure showing the test results of Experimental Example 9 as to the in vivo CTL induction ability of a compound represented by the formula (9) synthesized in Example 10 in the pulsed or non-pulsed state with peptide of SEQ ID NO: 5, by IFNγ ELISPOT assay using HLA-A0201 transgenic mouse.
Figure 12:
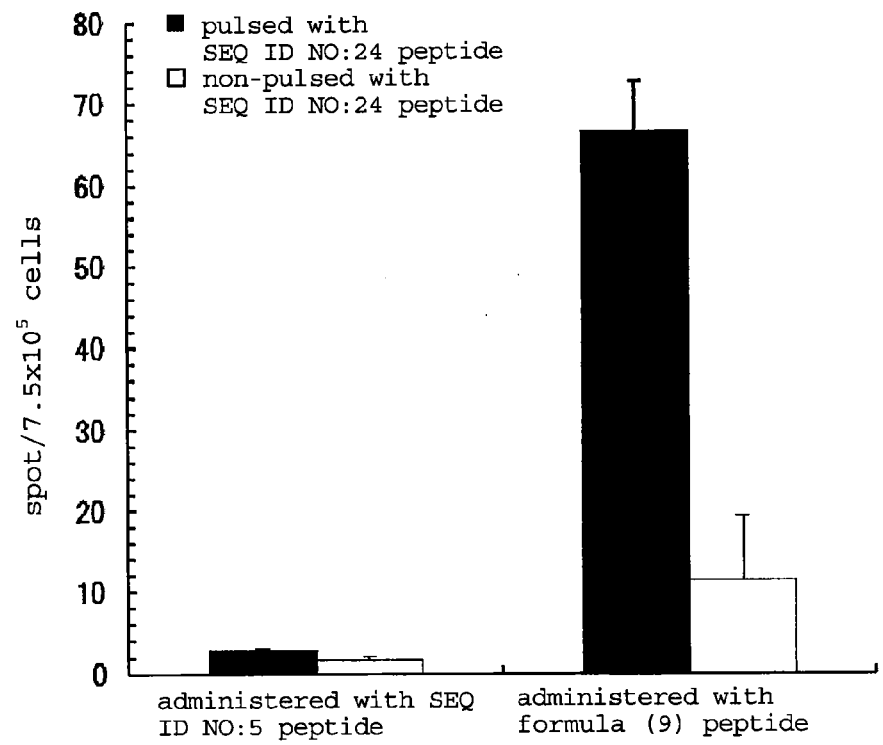
FIG. 12 is a Figure showing the test results of Experimental Example 9 as to the ability of a compound represented by the formula (9) synthesized in Example 10 to induce cells reactive with peptide shown by SEQ ID NO: 24 in vivo, by IFNγ ELISPOT assay using HLA-A0201 transgenic mouse in the pulsed or non-pulsed state with peptide of SEQ ID NO: 24.

The results of IFNγ ELISPOT assay using the HLA-A0201 transgenic mouse are shown in FIGS. 11 and 12. In FIGS. 11 and 12, the vertical axis shows the number of cells that reacted in the plated cells, and the horizontal axis shows the compound or peptide administered to the mouse. In FIG. 11, the black bar shows the results of culture of HLA-A0201 transgenic mouse-derived splenocytes while being pulsed with the peptide shown by SEQ ID NO: 5, and the white bar shows the results of culture without pulsing. That is, the difference in the values of the black and the white bar shows the number of peptide-specific CTL, and that the administration of the peptide shown by SEQ ID NO: 5 or a compound represented by the formula (9) resulted in the induction of CTL specific to the peptide shown by SEQ ID NO: 5 in vivo in the mouse. In FIG. 11, the value of the white bar is not detected. This means that the splenocytes of HLA-A0201 transgenic mice did not react in the absence of pulsing with the object peptide. As a result of this test, IFNγ production specific to the peptide shown by SEQ ID NO: 5 was detected in the HLA-A0201 transgenic mouse-derived splenocytes. In FIG. 11, the number of IFNγ-producing cells specific to the peptide shown by SEQ ID NO: 5, which were induced by the administration of a compound represented by the formula (9), was higher than that of the peptide-specific IFNγ-producing cells induced by the administration of the peptide shown by SEQ ID NO: 5.

In FIG. 12, furthermore, the black bar shows the results of culture of HLA-A0201 transgenic mouse-derived splenocytes while being pulsed with peptide shown by SEQ ID NO: 24, and the white bar show the results of culture without pulsing. That is, the difference in the values of the black bar and the white bar shows the number of peptide-reactive cells, and that the administration of a compound represented by the formula (9) resulted in the induction of cells reactive with the helper peptide shown by SEQ ID NO: 24 in vivo in the mouse, and administration of the peptide represented by SEQ ID NO: 5 did not induce cells reactive with the peptide shown by SEQ ID NO: 24 in vivo in the mouse. In FIG. 12, the value of the white bar is scarcely detected. This means that the splenocytes of HLA-A0201 transgenic mice did not react in the absence of pulsing with the object peptide.

From the above, it was clarified that a compound represented by the formula (9) can induce CTL specific to the peptide shown by SEQ ID NO: 5 and CTL reactive with the helper peptide shown by SEQ ID NO: 24. It was strongly suggested that the compound represented by the formula (9) undergoes cleavage of disulfide bond and appropriate trimming by ERAP-1 in mouse in vivo and is in fact processed into the peptides shown by SEQ ID NOs: 5 and 24. It was assumed that the induction of the cell reactive with the helper peptide shown by SEQ ID NO: 24 produced from a compound represented by the formula (9) enhanced induction of CTL specific to the peptide shown by SEQ ID NO: 5, and many IFNγ-producing cells specific to the peptide shown by SEQ ID NO: 5 were found, as compared to the administration of the compound shown by SEQ ID NO: 5.

That is, it was clarified that a compound represented by the formula (9), which is one embodiment of the compound of the present invention, is a conjugate wherein two different kinds of peptides form a composite via the disulfide bond shown in the formula (1), and is a WT1 cancer antigen peptide conjugate vaccine that in fact can induce CTLs and helper peptide reactive cells in vivo.

Comparative Example 1

Evaluation of In Vivo CTL Induction Ability Using HLA-A0201 Transgenic Mouse and HLA-A2402 Transgenic Mouse The compound represented by the formula (5) synthesized in Example 1 and the peptide shown by SEQ ID NO: 238 and 239 synthesized in Reference Example 8 and 9 were evaluated for the CTL induction ability by an in vivo CTL induction test using HLA-A0201 transgenic mouse and HLA-A2402 transgenic mouse. The compound represented by the formula (5):

(5)

wherein the bond between C and C is a disulfide bond, is as described in Experimental Example 2. The peptide shown by SEQ ID NOs: 238 and 239 is a long chain peptide wherein RMFPNAPYL (SEQ ID NO: 2), which is an HLA-A0201-restricted WT1 peptide, and CYTWNQMNL (SEQ ID NO: 4), which is HLA-A2402-restricted WT1 peptide, are linked by an amide bond.

The HLA-A0201 transgenic mouse and HLA-A2402 transgenic mouse are as described in Experimental Example 2.

Whether the administration of a compound represented by the formula (5) and the peptide shown by SEQ ID NO: 238, 239 results in the induction of CTL specific to the object peptide (SEQ ID NO: 2, 4) was judged based on the measurement of IFNγ production by re-stimulation, with the peptide (SEQ ID NO: 2, 4), of the splenocyte derived from the above-mentioned mouse administered with a compound represented by the formula (5) and the peptide shown by SEQ ID NO: 238, 239.

Specifically, a compound represented by the formula (5) and the peptide shown by SEQ ID NOs: 238, 239 were each dissolved in dimethyl sulfoxide (DMSO) at 40 mg/mL, further diluted with water for injection to 5 mg/mL, and emulsified by mixing with an equal amount of incomplete Freund's adjuvant (IFA). The emulsified compound was intradermally administered to 4 sites at the base of tail of a mouse at 250 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at 0.25×10⁶ cells/well, and HLA-A2402 transgenic mouse-derived splenocytes were plated at 1×10⁶ cells/well, on the blocked ELISPOT plate. Peptide (SEQ ID NO: 2, 4) was dissolved in DMSO at 40 mg/mL, and further diluted with RPMI1640 medium containing 10% FBS to 40 µg/mL. The diluted peptide (SEQ ID NO: 2) was added to the HLA-A0201 transgenic mouse-derived splenocytes at a final concentration of 10 µg/mL. In addition, the diluted peptide (SEQ ID NO: 4) was added to the HLA-A2402 transgenic mouse-derived splenocytes at a final concentration of 10 µg/mL. The splenocytes added with the peptide were cultivated for 18 hr at 37° C., 5% CO₂, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 13:
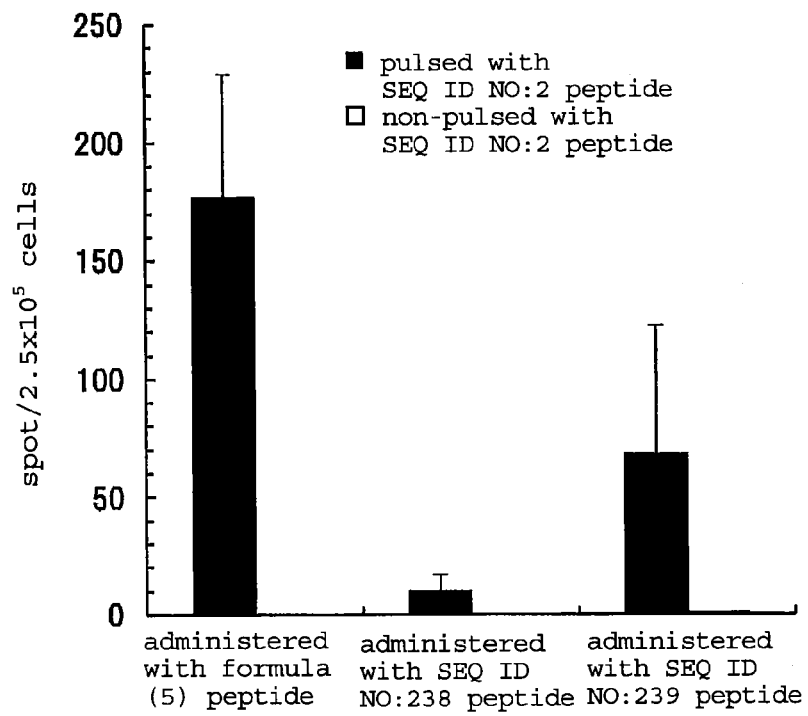
FIG. 13 is a Figure showing the test results of Comparative Example 1 as to the in vivo CTL induction ability of peptides shown by SEQ ID NO: 238 and 239 synthesized in Reference Examples 8 and 9 in the pulsed or non-pulsed state with peptide of SEQ ID NO: 2, by IFNγ ELISPOT assay using HLA-A0201 transgenic mouse.
Figure 14:
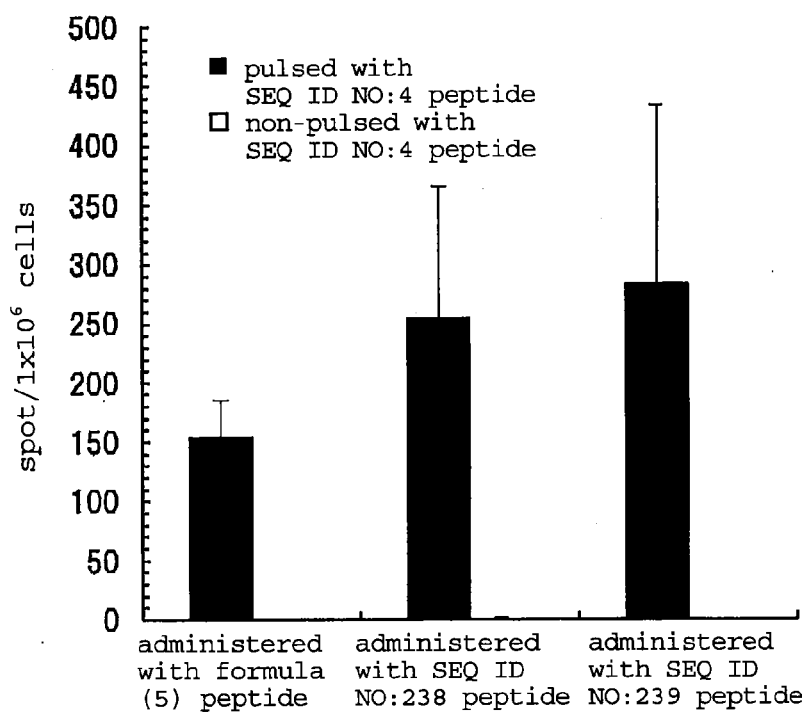
FIG. 14 is a Figure showing the test results of Comparative Example 1 as to the in vivo CTL induction ability of peptides shown by SEQ ID NO: 238 and 239 synthesized in Reference Examples 8 and 9 in the pulsed or non-pulsed state with peptide of SEQ ID NO: 4, by IFNγ ELISPOT assay using HLA-A2402 transgenic mouse.

The results of IFNγ ELISPOT assay using HLA-A0201 transgenic mouse are shown in FIG. 13, and the results of IFNγ ELISPOT assay using HLA-A2402 transgenic mouse are shown in FIG. 14.

In each Figure, the vertical axis shows the number of cells that reacted in the plated cells. In FIG. 13, the black bar and the white bar show the results of culture of HLA-A0201 transgenic mouse-derived splenocytes in the presence or absence of the object peptide represented by SEQ ID NO: 2, and in FIG. 14, the black bar and the white bar show the results of culture of HLA-A2402 transgenic mouse-derived splenocytes in the presence or absence of the object peptide represented by SEQ ID NO: 4. That is, the difference in the values of the black bar and the white bar show the number of the object, each peptide-specific CTL induced in the mouse in vivo by the administration of a compound represented by the formula (5) and the peptide shown by SEQ ID NO: 238, 239.

In each Figure, the value of the white bar is not detected. This means that the splenocytes of respective transgenic mice did not react at all in the absence of the object peptide. As a result of this test, IFNγ production specific to the object peptide shown by SEQ ID NO: 2 was detected in the splenocytes derived from HLA-A0201 transgenic mouse administered with a compound represented by the formula (5), and IFNγ production specific to the object peptide shown by SEQ ID NO: 4 was detected in the splenocytes derived from HLA-A02402 transgenic mouse administered with a compound represented by the formula (5). On the other hand, while IFNγ production specific to the object peptide shown by SEQ ID NO: 2 was detected in the splenocytes derived from HLA-A0201 transgenic mouse administered with the peptide shown by SEQ ID NO: 238; however, when compared to the splenocytes derived from HLA-A2402 transgenic mouse administered with a compound represented by the formula (5), the number thereof was very small. IFNγ production specific to the object peptide shown by SEQ ID NO: 4 was detected in the splenocytes derived from HLA-A2402 transgenic mouse administered with the peptide shown by SEQ ID NO: 238. While IFNγ production specific to the object peptide shown by SEQ ID NO: 2 was detected in the splenocytes derived from HLA-A0201 transgenic mouse administered with the peptide shown by SEQ ID NO: 239; however, when compared to the splenocytes derived from HLA-A0201 transgenic mouse administered with a compound represented by the formula (5), the number thereof was small. IFNγ production specific to the object peptide shown by SEQ ID NO: 4 was detected in the splenocytes derived from HLA-A2402 transgenic mouse administered with peptide SEQ ID NO: 239.

Therefrom, the compound represented by the formula (5) of the present invention has been clarified to be able to efficiently induce CTL specific to the peptide shown by SEQ ID NO: 2 and CTL specific to the peptide shown by SEQ ID NO: 4. On the other hand, the long chain peptide shown by SEQ ID NOs: 238, 239 could not efficiently induce both the CTL specific to the peptide shown by SEQ ID NO: 2 and the CTL specific to the peptide shown by SEQ ID NO: 4.

Comparative Example 2

Evaluation of in vivo CTL induction ability using HLA-A0201 transgenic mouse and HLA-A2402 transgenic mouse The compound represented by the formula (5) synthesized in Example 1 and peptides shown by SEQ ID NOs: 240 and 241 synthesized in Reference Examples 10 and 11 were evaluated for the CTL induction ability by an in vivo CTL induction test using HLA-A0201 transgenic mouse and HLA-A2402 transgenic mouse. The compound represented by the formula (5):

(5)

wherein the bond between C and C is a disulfide bond, is as described in Experimental Example 2. The peptide shown by SEQ ID NOs: 240 and 241 is a long chain peptide wherein RMFPNAPYL (SEQ ID NO: 2), which is an HLA-A0201-restricted WT1 peptide, and CYTWNQMNL (SEQ ID NO: 4), which is an HLA-A2402-restricted WT1 peptide, are linked by an amide bond via 6 glycines as a peptide spacer.

HLA-A0201 transgenic mouse and HLA-A2402 transgenic mouse are as indicated in Experimental Example 2.

Whether the administration of a compound represented by the formula (5) and SEQ ID NO: 240, 241 peptide shown by results in the induction of CTL specific to the object peptide (SEQ ID NO: 2, 4) was judged based on the measurement of IFNγ production by re-stimulation, with the peptide (SEQ ID NO: 2, 4), of the splenocyte derived from the above-mentioned mouse administered with a compound represented by the formula (5) and the peptide shown by SEQ ID NO: 240, 241.

Specifically, a compound represented by the formula (5) was dissolved in dimethyl sulfoxide (DMSO) at 80 mg/mL, further diluted with water for injection to 10 mg/mL, and emulsified by mixing with an equal amount of incomplete Freund's adjuvant (IFA). The emulsified compound was intradermally administered to 2 sites at the base of tail of a mouse at 500 µg/site. In addition, the peptides shown by SEQ ID NOs: 240, 241 were dissolved in dimethyl sulfoxide (DMSO) at 80 mg/mL, further diluted with water for injection to 11 mg/mL, and emulsified by mixing with an equal amount of incomplete Freund's adjuvant (IFA). The emulsified compound was intradermally administered to 2 sites at the base of tail of a mouse at 550 µg/site. One week later, the mouse was euthanized with CO₂ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes at 0.25× 10⁶ cells/well and HLA-A2402 transgenic mouse-derived splenocytes at 1.5×10⁶ cells/well were plated on the blocked ELISPOT plate. Peptide (SEQ ID NO: 2, 4) was dissolved in DMSO at 40 mg/mL, and further diluted with RPMI1640 medium containing 10% FBS to 40 µg/mL. The diluted peptide (SEQ ID NO: 2) was added to the HLA-A0201 transgenic mouse-derived splenocytes at a final concentration of 10 µg/mL. In addition, the diluted peptide (SEQ ID NO: 4) was added to HLA-A2402 transgenic mouse-derived splenocytes at a final concentration of 10 µg/mL. The splenocytes added with the peptide were cultured for 17 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 15:
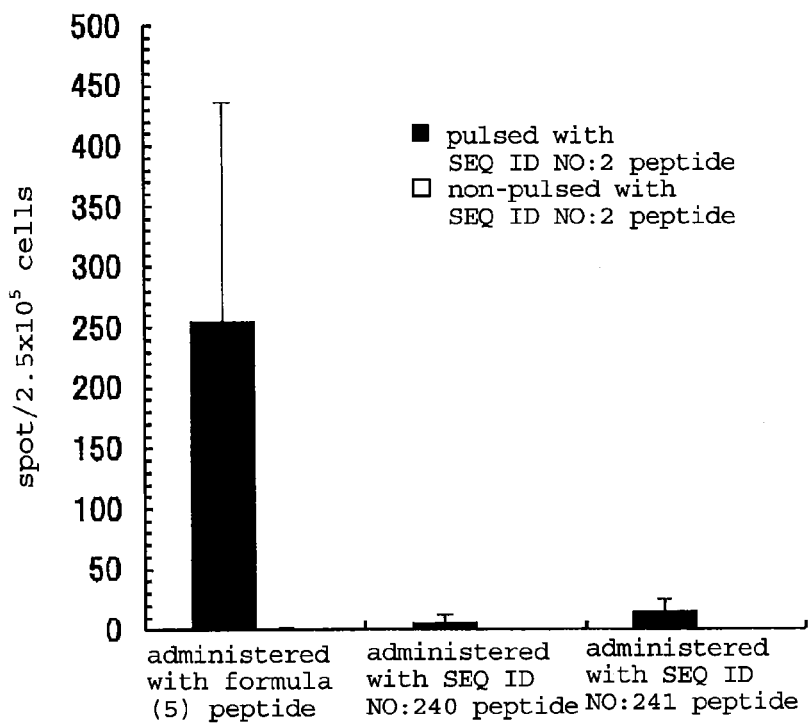
FIG. 15 is a Figure showing the test results of Comparative Example 2 as to the in vivo CTL induction ability of peptides shown by SEQ ID NO: 240 and 241 synthesized in Reference Examples 10 and 11 in the pulsed or non-pulsed state with peptide of SEQ ID NO: 2, by IFNγ ELISPOT assay using HLA-A0201 transgenic mouse.
Figure 16:
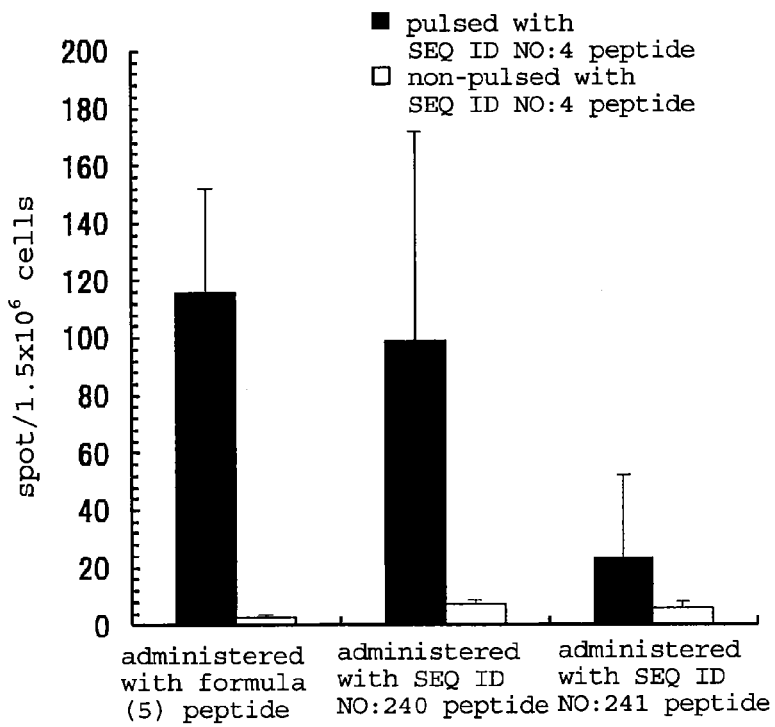
FIG. 16 is a Figure showing the test results of Comparative Example 2 as to the in vivo CTL induction ability of peptides shown by SEQ ID NO: 240 and 241 synthesized in Reference Examples 10 and 11 in the pulsed or non-pulsed state with peptide of SEQ ID NO: 4, by IFNγ ELISPOT assay using HLA-A2402 transgenic mouse.

The results of IFNγ ELISPOT assay using HLA-A0201 transgenic mouse are shown in FIG. 15, and the results of IFNγ ELISPOT assay using HLA-A2402 transgenic mouse are shown in FIG. 16.

In each Figure, the vertical axis shows the number of cells that reacted in the plated cells. In FIG. 15, the black bar and the white bar show the results of culture of HLA-A0201 transgenic mouse-derived splenocytes in the presence or absence of the object peptide represented by SEQ ID NO: 2, and in FIG. 16, the black bar and the white bar show the results of culture of HLA-A2402 transgenic mouse-derived splenocytes in the presence or absence of the object peptide represented by SEQ ID NO: 4. That is, the difference in the values of the black bar and the white bar show the number of the object, each peptide-specific CTL induced in the mouse in vivo by the administration of a compound represented by the formula (5) and the peptides shown by SEQ ID NOs: 240, 241.

In each Figure, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with a compound represented by the formula (5), and IFNγ production specific to the object peptide shown by SEQ ID NO: 4 was detected in the splenocytes derived from HLA-A2402 transgenic mouse administered with a compound represented by the formula (5). On the other hand, IFNγ production specific to the object peptide shown by SEQ ID NO: 2 was extremely less in the splenocytes derived from HLA-A0201 transgenic mouse administered with the peptide shown by SEQ ID NO: 240; however, IFNγ production specific to the object peptide shown by SEQ ID NO: 4 was detected in the splenocytes derived from HLA-A02402 transgenic mouse administered with a compound represented by SEQ ID NO: 240. In addition, IFNγ production specific to the object peptide shown by SEQ ID NO: 2 was extremely less in the splenocytes derived from HLA-A0201 transgenic mouse administered with the peptide shown by SEQ ID NO: 241. While IFNγ production specific to the object peptide shown by SEQ ID NO: 4 was detected in the splenocytes derived from HLA-A0201 transgenic mouse administered with the peptide shown by SEQ ID NO: 241; however, when compared to the splenocytes derived from HLA-A2402 transgenic mouse administered with a compound represented by the formula (5), the number thereof was very small.

Therefrom, the compound represented by the formula (5) of the present invention has been clarified to be able to efficiently induce CTL specific to the peptide shown by SEQ ID NO: 2 and CTL specific to the peptide shown by SEQ ID NO: 4. On the other hand, the long chain peptide containing the peptide spacer shown by SEQ ID NO: 240, 241 could not efficiently induce both the CTL specific to the peptide shown by SEQ ID NO: 2 and the CTL specific to the peptide shown by SEQ ID NO: 4.

Experimental Example 10

The peptide synthesized in Reference Example 3 and the compounds (conjugates) synthesized in Examples 6 and 9 were subjected to the solubility measurement by a method similar to that in Experimental Example 3. Each solubility is shown in Table 66.

TABLE 66

| Ex. No. and Ref. Ex. | amino acid sequence or structural formula | SEQ ID NO: or formula No. | pH 6.0 (mg/mL) | pH 7.4 (mg/mL) |
| --- | --- | --- | --- | --- |
| Ref. Ex. 3 | CNKRYFKLSHLQMHSRKH | SEQ ID NO: 23 | >1.0 | 0.712 |
| Ex. 6 | CRMFPNAPYL<br>\|<br>CSLGEQQYSV | formula (3) | >1.0 | >1.0 |
| Ex. 10 | CALLPAVSL<br>\|<br>CNKRYFKLSHLQMHSRKHTG | formula (9) | >1.0 | 0.565 |

Examples 11-12

By a method similar to that in Example 2, peptides consisting of the amino acid sequences of SEQ ID NOs: 242-243 were synthesized. The results of mass spectrometry are shown in Table 67. The peptides described in Table 67 are the compounds of the present invention.

TABLE 67

| Ex. No. | amino acid sequence | SEQ ID NO: | mass spectrometry: LC-ESI/MS m/z | mass spectrometry: Calculated |
| --- | --- | --- | --- | --- |
| 11 | CWAPVLDFAPPGASAYGSL | 242 | 1923.5 $[M + H]^{1+}$ | 1923.2 |
| 12 | WAPVLDFAPPGASAYGSLC | 243 | 1923.6 $[M + H]^{1+}$ | 1923.2 |

Example 13

By a method similar to that in Example 1, each compound (conjugate) represented by the formula 10 was synthesized. The results of mass spectrometry are shown in Table 68, wherein the bond between C and C is a disulfide bond.

TABLE 68

| Ex. No. | structural formula | formula No. | mass spectrometry: LC-ESI/MS m/z | mass spectrometry: Calculated |
| --- | --- | --- | --- | --- |
| 13 | CRMFPNAPYL<br>\|<br>CWAPVLDFAPPGASAYGSL | 10 | 1566.6 $[M + 2H]^{2+}$ | 1566.8 |

Reference Example 12

By a method similar to that in Example 1, each compound (conjugate) represented by the formula 11 was synthesized. The results of mass spectrometry are shown in Table 69, wherein the bond between C and C is a disulfide bond. The peptide described in the Table is not the compound of the present invention, and therefore, it is described as Reference Example.

TABLE 69

| Ref. Ex. No. | structural formula | formula No. | mass spectrometry: LC-ESI/MS m/z | mass spectrometry: Calculated |
| --- | --- | --- | --- | --- |
| 12 | WAPVLDFAPPGASAYGSLC<br>\|<br>CRMFPNAPYL | 11 | 1044.8 $[M + 3H]^{3+}$ | 1044.9 |

Example 14

Synthesis of the Compound Represented by the Formula (12)

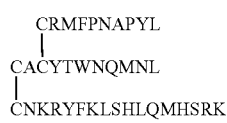
(12)

wherein the bond between C and C is a disulfide bond

Step 1. Synthesis of Fmoc-Cys(Mmt)-Ala-SBn (Mmt is 4-Methoxytrityl)

(Synthesis of Fmoc-C(Mmt)A-SBn)

A solution of Fmoc-Cys(Mmt)-OH (4.80 g), N,N-diisopropylethylamine (2.56 mL), hexafluorophosphoric acid (benzotriazol-1-yloxy)tripyrrolidinophosphonium (4.50 g) and H-Ala-SBn synthesized by a known method (for example, Journal of Organic Chemistry, Vol. 64, No. 24 8761-8769) in chloroform (20 ml) was stirred at room temperature for 1 hr. The reaction mixture was purified by column chromatography (elution solvent, hexane/ethyl acetate) to give the object compound, Fmoc-C(Mmt)A-SBn (2.80 g).

NMR: $^1$H NMR (CDCl$_3$) δ 7.72 (t, J=7.6 Hz, 2H), 7.54 (d, J=7.2 Hz, 1H), 7.38-7.34 (m, 7H), 7.29-7.25 (m, 6H), 7.23-7.15 (m, 7H), 6.76 (d, J=8.8 Hz, 2H), 6.15 (d, J=8.0 Hz, 1H), 4.95 (d, J=7.2 Hz, 1H), 4.57 (quin, J=7.6 Hz, 1H), 4.35 (d, J=6.8 Hz, 2H) 4.19-4.17 (m, 1H), 4.04 (s, 2H), 3.73 (s, 3H), 2.72 (dd, J=13.2, 8.4 Hz, 1H), 2.61 (d, J=9.6 Hz, 1H), 1.31 (d, J=7.2 Hz, 3H).

Step 2. Synthesis of H-Cys(Mmt)-Ala-Cys-Tyr-Thr-Trp-Asn-Gln-Met-Asn-Leu-OH (Synthesis of C(Mmt)ACYTWNQMNL)

A solution of Fmoc-Cys(Mmt)-Ala-SBn (11 mg) obtained in step 1, H-Cys-Tyr-Thr-Trp-Asn-Gln-Met-Asn-Leu-OH (21 mg) synthesized by a known method (for example, WO07/063903), N,N-diisopropylethylamine (200 μL), 3,3',3"-Phosphanetriyl tripropanoic acid hydrochloride (1 mg), 4-mercaptophenylacetic acid (1 mg) and 0.1M sodium phosphate buffer (pH 7.5, 200 μL) in DMF (400 μL) was stirred at room temperature for 4 hr. To the reaction mixture was added diethylamine (200 μL) and the mixture was further stirred for 15 min. The reaction mixture was purified by reversed-phase HPLC to give the object compound, C(Mmt)ACYTWNQMNL (7 mg).

mass spectrometry: LC-ESI/MS m/z=810.2 $[M+2H]^{2+}$ (Calculated=810.5)

Step 3. Synthesis of (H-Cys(Mmt)-Ala-Cys-Tyr-Thr-Trp-Asn-Gln-Met-Asn-Leu-OH) (H-Cys-Arg-Met-Phe-Pro-Asn-Ala-Pro-Tyr-Leu-OH) Disulfide Bond

[i.e., synthesis of a compound represented by the formula (13):

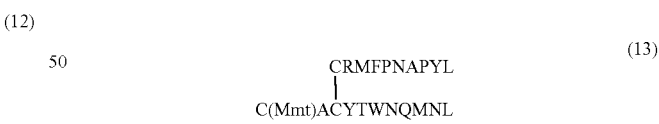
(13)

wherein the bond between C and C is a disulfide bond.

A solution of H-Cys(Mmt)-Ala-Cys-Tyr-Thr-Trp-Asn-Gln-Met-Asn-Leu-OH (51 mg) obtained in step 2 and (H-Cys(Npys)-Arg-Met-Phe-Pro-Asn-Ala-Pro-Tyr-Leu-OH) (43 mg) obtained in Example 1, step 1 in DMF (4 mL) was stirred at room temperature for 2 hr. The reaction mixture was purified by reversed-phase HPLC to give 39 mg of the object compound, (H-Cys(Mmt)-Ala-Cys-Tyr-Thr-Trp-Asn-Gln-Met-Asn-Leu-OH) (H-Cys-Arg-Met-Phe-Pro-Asn-Ala-Pro-Tyr-Leu-OH) disulfide bond [i.e., a compound represented by the formula (13)].

mass spectrometry: LC-ESI/MS m/z=1414.4 $[M+2H]^{2+}$ (Calculated=1415.2)

Step 4. Synthesis of H-Cys(SPy)-Asn-Lys-Arg-Tyr-Phe-Lys-Leu-Ser-His-Leu-Gln-Met-His-Ser-Arg-Lys-OH (Synthesis of C(SPy)NKRYFKLSHLQMHSRK)

A 20% w/w solution of H-Cys-Asn-Lys-Arg-Tyr-Phe-Lys-Leu-Ser-His-Leu-Gln-Met-His-Ser-Arg-Lys-OH (182 mg) obtained in Reference Example 1 and 2,2'-dipyridylbisulfide (0.2M isopropanol solution, 544 µL) in acetic acid water (4 mL) was stirred at room temperature for 17 hr. The reaction mixture was purified by reversed-phase HPLC to give the object compound, H-Cys(SPy)-Asn-Lys-Arg-Tyr-Phe-Lys-Leu-Ser-His-Leu-Gln-Met-His-Ser-Arg-Lys-OH (177 mg).

mass spectrometry: LC-ESI/MS m/z=1143.5 [M+21-1]$^{2+}$ (Calculated=1142.9)

Step 5. Synthesis of a Compound Represented by the Formula (12)

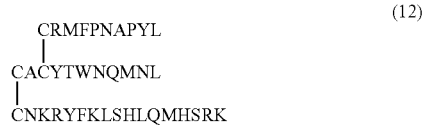

(12)

wherein the bond between C and C is a disulfide bond

A solution of (H-Cys(Mmt)-Ala-Cys-Tyr-Thr-Trp-Asn-Gln-Met-Asn-Leu-OH)(H-Cys-Arg-Met-Phe-Pro-Asn-Ala-Pro-Tyr-Leu-OH) disulfide bond obtained in step 3 [i.e., a compound represented by the formula (13)] (9 mg), H-Cys(SPy)-Asn-Lys-Arg-Tyr-Phe-Lys-Leu-Ser-His-Leu-Gln-Met-His-Ser-Arg-Lys-OH (24 mg) obtained in step 4 and triisopropylsilane (10 µL) in trifluoroacetic acid (190 µL) was stirred at room temperature for 1 hr. The reaction mixture was purified by reversed-phase HPLC to give the object compound, a compound represented by the formula 12 (5 mg).

mass spectrometry: LC-ESI/MS m/z=1577.2 [M+3H]$^{3+}$ (Calculated=1577.9)

Examples 15-16

By a method similar to that in Example 14, each compound (conjugate) represented by the formula 14 or 15 was synthesized. The results of mass spectrometry are shown in Table 70, wherein the bond between C and C is a disulfide bond.

TABLE 70

| Ex. No. | structural formula | formula No. | mass spectrometry: LC-ESI/MS m/z | mass spectrometry: Caluclated |
|---|---|---|---|---|
| 15 | CRMFPNAPYL<br>\|<br>CACYTWNQMNL<br>\|<br>CWAPVLDFAPPGASAYGSL | 14 | 1492.5 [M + 3H]$^{3+}$ | 1493.1 |
| 16 | CWAPVLDFAPPGASAYGSL<br>\|<br>CACYTWNQMNL<br>\|<br>CRMFPNAPYL | 15 | 1492.5 [M + 3H]$^{3+}$ | 1493.1 |

Reference Example 13

By a method similar to that in Example 2, peptides consisting of the amino acid sequence of SEQ ID NO: 244 were synthesized. Table 71 shows the results of mass spectrometry. The peptide described in the Table is not the compound of the present invention, and therefore, it is described as Reference Example.

TABLE 71

| Ref. Ex. No. | amino acid sequence | SEQ ID NO: | mass spectrometry: LC-ESI/MS m/z | mass spectrometry: Calculated |
|---|---|---|---|---|
| 13 | WAPVLDFAPPGASAYGSL | 244 | 1819.8 [M + H]$^+$ | 1819.1 |

Experimental Example 11

Evaluation of In Vivo CTL Induction Ability Using HLA-A0201 Transgenic Mouse The compound represented by the formula (10) synthesized in Example 13 was evaluated for the CTL induction ability by an in vivo CTL induction test using HLA-A0201 transgenic mouse. The compound represented by the formula (10):

(10)

wherein the bond between C and C is a disulfide bond, is, in particular, a compound of the aforementioned formula (1), wherein cancer antigen peptide A is RMFPNAPYL (SEQ ID NO: 2) and cancer antigen peptide B is WAPVLDFAPP-GASAYGSL (SEQ ID NO: 244). RMFPNAPYL (SEQ ID NO: 2) is an HLA-A0201-restricted WT1 peptide, and WAPVLDFAPPGASAYGSL (SEQ ID NO: 244) is MHC class II-restricted WT1 peptide (namely, helper peptide).

The HLA-A0201 transgenic mouse is as described in Experimental Examples 2 and 5.

Whether the administration of a compound represented by the formula (10) results in the induction of CTL specific to the object peptide (SEQ ID NO: 2) was judged based on the measurement of IFNγ production by re-stimulation, with the peptide (SEQ ID NO: 2), of the splenocyte derived from the above-mentioned mouse administered with a compound represented by the formula (10). Whether or not the helper peptide (SEQ ID NO: 244) works in the living body was judged by comparison of the number of IFNγ-producing cells when the splenocytes derived from the above-mentioned mouse administered with a compound represented by the formula (10) and the splenocytes derived from the above-mentioned mouse administered with the peptide shown by SEQ ID NO: 2 were re-stimulated with the peptide (SEQ ID NO: 2).

Specifically, a compound shown by SEQ ID NO: 2 was dissolved in dimethyl sulfoxide (DMSO) at 80 mg/mL, further diluted with water for injection to 3 mg/mL, and emulsified by mixing with an equal amount of incomplete Freund's adjuvant (IFA). The emulsified compound was intradermally administered to 2 sites at the base of tail of a mouse at 150 μg/site. In addition, a compound represented by the formula (10) was dissolved in dimethyl sulfoxide (DMSO) at 80 mg/mL, further diluted with water for injection to 8.5 mg/mL, and emulsified by mixing with an equal amount of incomplete Freund's adjuvant (IFA). The emulsified compound was intradermally administered to 2 sites at the base of tail of a mouse at 425 μg/site. The mole number of the peptide of the SEQ ID NO: 2 contained in the dose of a compound represented by the formula (10) per mouse was controlled to be equal to the mole number contained in the dose of the peptide shown by SEQ ID NO: 2 per mouse. In addition, the concentration of DMSO contained in each emulsion was also set to the same level. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at 0.125×10$^6$ cells/well on the blocked ELISPOT plate. Peptide (SEQ ID NO: 2, 4) was dissolved in DMSO at 40 mg/mL, and further diluted with RPMI1640 medium containing 10% FBS to 40 μg/mL. The diluted peptide (SEQ ID NO: 2) was added to the HLA-A0201 transgenic mouse-derived splenocytes at a final concentration of 10 μg/mL. The splenocytes added with the peptide were cultivated for 19 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 17:
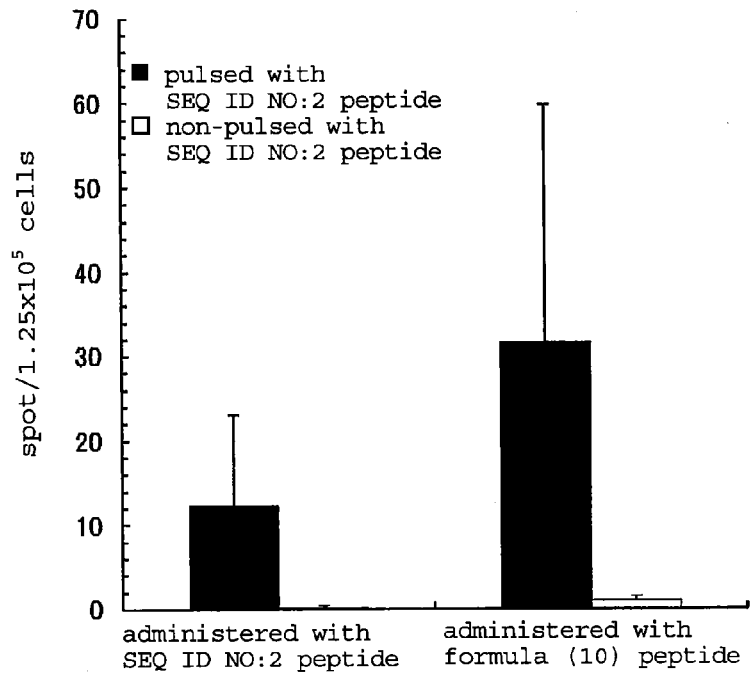
FIG. 17 is a Figure showing the test results of Experimental Example 11 as to the in vivo CTL induction ability of a compound represented by the formula (10) synthesized in Example 13 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 17. In FIG. 17, the vertical axis shows the number of cells that reacted in the plated cells, and the horizontal axis shows compound or peptide administered to the mouse. In FIG. 17, the black bar shows the results of culture of HLA-A0201 transgenic mouse-derived splenocytes while being pulsed with the peptide shown by SEQ ID NO: 2, and the white bar shows the results of culture without pulsing. That is, the difference in the values of the black bar and the white bar shows the number of peptide-specific CTL, and that the administration of the peptide shown by SEQ ID NO: 2 or a compound represented by the formula (10) resulted in the induction of CTL specific to the peptide shown by SEQ ID NO: 2 in vivo in the mouse. In FIG. 17, the value of the white bar is not detected. This means that the splenocytes of HLA-A0201 transgenic mice did not react at all in the absence of pulsing with the object peptide. As a result of this test, IFNγ production specific to the peptide shown by SEQ ID NO: 2 was is detected in the HLA-A0201 transgenic mouse-derived splenocytes. Moreover, in FIG. 17, the number of IFNγ-producing cells specific to the peptide shown by SEQ ID NO: 2, which were induced by the administration of a compound represented by the formula (10), was higher than that of the peptide-specific IFNγ-producing cells induced by the administration of the peptide shown by SEQ ID NO: 2.

From the above, it was clarified that a compound represented by the formula (10) can induce CTL specific to the peptide shown by SEQ ID NO: 2. When a compound represented by the formula (10) was administered, many IFNγ producing cells specific to the peptide shown by SEQ ID NO: 2 were observed as compared to administration of the peptide shown by SEQ ID NO: 2. It was assumed that the induction of the cell reactive with the helper peptide shown by SEQ ID NO: 244 produced from a compound represented by the formula (10) enhanced induction of CTL specific to the peptide shown by SEQ ID NO: 2. Therefore, it was strongly suggested that the compound represented by the formula (10) undergoes cleavage of disulfide bond and appropriate trimming by ERAP-1 in mouse in vivo and is in fact processed into the peptides shown by SEQ ID NOs: 2 and 244.

That is, it was clarified that a compound represented by the formula (10), which is one embodiment of the compound of the present invention, is a conjugate wherein two different kinds of peptides form a composite via the disulfide bond shown in the formula (1), and is a WT1 cancer antigen peptide conjugate vaccine that in fact can induce CTLs and helper peptide reactive cells in vivo.

Comparative Example 3

Evaluation of In Vivo CTL Induction Ability Using HLA-A0201 Transgenic Mouse

The compound represented by the formula (11) synthesized in Reference Example 12 was evaluated for the CTL induction ability by an in vivo CTL induction test using HLA-A0201 transgenic mouse. The compound represented by the formula (11):

(11)

wherein the bond between C and C is a disulfide bond, is, in particular, a compound of the aforementioned formula (1), wherein cancer antigen peptide A is RMFPNAPYL (SEQ ID NO: 2) and cancer antigen peptide C is WAPVLDFAPP-GASAYGSLC (SEQ ID NO: 243). RMFPNAPYL (SEQ ID NO: 2) is a HLA-A0201-restricted WT1 peptide, and WAPV-LDFAPPGASAYGSL (SEQ ID NO: 244) is an MHC class II-restricted WT1 peptide (namely, helper peptide).

The HLA-A0201 transgenic mouse is as described in Experimental Examples 2 and 5.

Whether the administration of a compound represented by the formula (11) results in the induction of CTL specific to the object peptide (SEQ ID NO: 2) was judged based on the measurement of IFNγ production by re-stimulation, with the peptide (SEQ ID NO: 2), of the splenocytes derived from the above-mentioned mouse administered with a compound represented by the formula (11). Whether or not the helper peptide (SEQ ID NO: 244) works in the living body was judged by comparison of the number of IFNγ-producing cells when the splenocytes derived from the above-mentioned mouse administered with a compound represented by the formula (11) and the splenocytes derived from the above-mentioned mouse administered with the peptide shown by SEQ ID NO: 2 were re-stimulated with the peptide (SEQ ID NO: 2).

By a method similar to that in Experimental Example 11, CTL induction test was performed.

Figure 18:
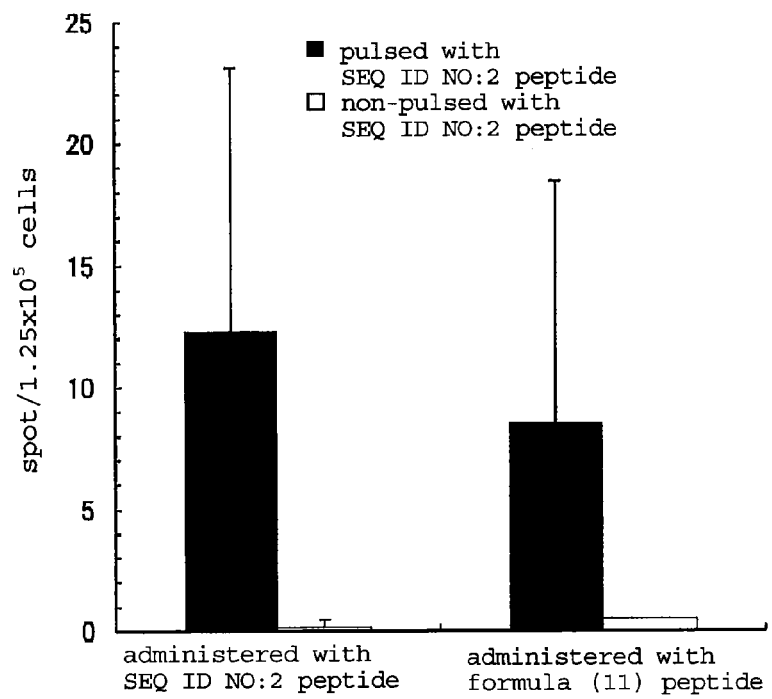
FIG. 18 is a Figure showing the test results of Comparative Example 3 as to the in vivo CTL induction ability of a compound represented by the formula (11) synthesized in Reference Example 12 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 18. In FIG. 18, the vertical axis shows the number of cells that reacted in the plated cells, and the horizontal axis shows compound or peptide administered to the mouse. In FIG. 18, the black bar shows the results of culture of HLA-A0201 transgenic mouse-derived splenocytes while being pulsed with the peptide shown by SEQ ID NO: 2, and the white bar shows the results of culture without pulsing. That is, the difference in the values of the black bar and the white bar shows the number of peptide-specific CTL, and that the administration of the peptide shown by SEQ ID NO: 2 or a compound represented by the formula (11) resulted in the induction of CTL specific to the peptide shown by SEQ ID NO: 2 in vivo in the mouse. In FIG. 18, the value of the white bar is not detected. This means that the splenocytes of HLA-A0201 transgenic mice did not react at all in the absence of pulsing with the object peptide. As a result of this test, IFNγ production specific to the peptide shown by SEQ ID NO: 2 was detected in the HLA-A0201 transgenic mouse-derived splenocytes. On the other hand, in FIG. 18, an increase in the IFNγ producing cells specific to the peptide shown by SEQ ID NO: 2, which was induced by the administration of the peptide shown by SEQ ID NO: 2, could not be detected by the administration of a compound represented by the formula (11).

The results of Experimental Example 11 and Comparative Example 3 suggest that, when WAPVLDFAPPGASAYGSL (SEQ ID NO: 244) is used as an MHC class II-restricted WT1 peptide, WAPVLDFAPPGASAYGSL (SEQ ID NO: 244) as the cancer antigen peptide B in the aforementioned formula (1) is a more preferable embodiment of the invention than WAPVLDFAPPGASAYGSLC (SEQ ID NO: 243) as the cancer antigen peptide C.

Experimental Example 12

Evaluation of In Vivo CTL Induction Ability Using HLA-A0201 Transgenic Mouse and HLA-A2402 Transgenic Mouse The CTL induction ability of the compound represented by the formula 12 synthesized in Example 14 was evaluated by an in vivo CTL induction test using an HLA-A0201 transgenic mouse and an HLA-A2402 transgenic mouse. RMFPNAPYL (SEQ ID NO: 2) contained in the compound represented by the formula (12):

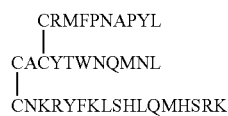

(12)

wherein the bond between C and C is a disulfide bond, is an HLA-A0201-restricted WT1 peptide, CYTWNQMNL (SEQ ID NO: 4) is HLA-A2402-restricted WT1 peptide, and CNKRYFKLSHLQMHSRK (SEQ ID NO: 22) is MHC class II-restricted WT1 peptide (namely, helper peptide).

The HLA-A0201 transgenic mouse and HLA-A2402 transgenic mouse are as described in Experimental Examples 2 and 5.

Whether the administration of a compound represented by the formula (12) results in the induction of CTL specific to the object peptide (SEQ ID NO: 2, 4) was judged based on the measurement of IFNγ production by re-stimulation, with the peptide (SEQ ID NO: 2, 4), of the splenocyte derived from the above-mentioned mouse administered with a compound represented by the formula (12). Whether or not the helper peptide (SEQ ID NO: 22) works in the living body was judged by comparison of the number of IFNγ-producing cells when the splenocytes derived from the above-mentioned mouse administered with a compound represented by the formula (12) and the splenocytes derived from the above-mentioned mouse administered with a compound represented by the formula (5) were re-stimulated with the peptide (SEQ ID NOs: 2, 4).

Specifically, a compound represented by the formula (5) was dissolved in dimethyl sulfoxide (DMSO) at 80 mg/mL, further diluted with water for injection to 3 mg/mL, and emulsified by mixing with an equal amount of Montanide ISA51VG. The emulsified compound was intradermally administered to 2 sites at the base of tail of a mouse at 150 μg/site. In addition, a compound represented by the formula (12) was dissolved in dimethyl sulfoxide (DMSO) at 80 mg/mL, further diluted with water for injection to 6 mg/mL, and emulsified by mixing with an equal amount of Montanide ISA51VG. The emulsified compound was intradermally administered to 2 sites at the base of tail of a mouse at 300 μg/site. The mole number of the compound represented by the formula (5) contained in the dose of the compound represented by the formula (12) per mouse was controlled to be equal to the mole number contained in the dose of the compound represented by the formula (5) per mouse. In addition, the concentration of DMSO contained in each emulsion was also set to the same level. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated, and HLA-A2402 transgenic mouse-derived splenocytes were each plated at $0.25 \times 10^6$ cells/well, on the blocked ELISPOT plate. Peptide (SEQ ID NO: 2, 4) was dissolved in DMSO at 40 mg/mL, and further diluted with RPMI1640 medium containing 10% FBS to 40 μg/mL. The diluted peptide (SEQ ID NO: 2) was added to the HLA-A0201 transgenic mouse-derived splenocytes at a final concentration of 10 μg/mL. In addition, the diluted peptide (SEQ ID NO: 4) was added to the HLA-A2402 transgenic mouse-derived splenocytes at a final concentration of 10 μg/mL. The splenocytes added with the peptide were cultivated for 17 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 19:
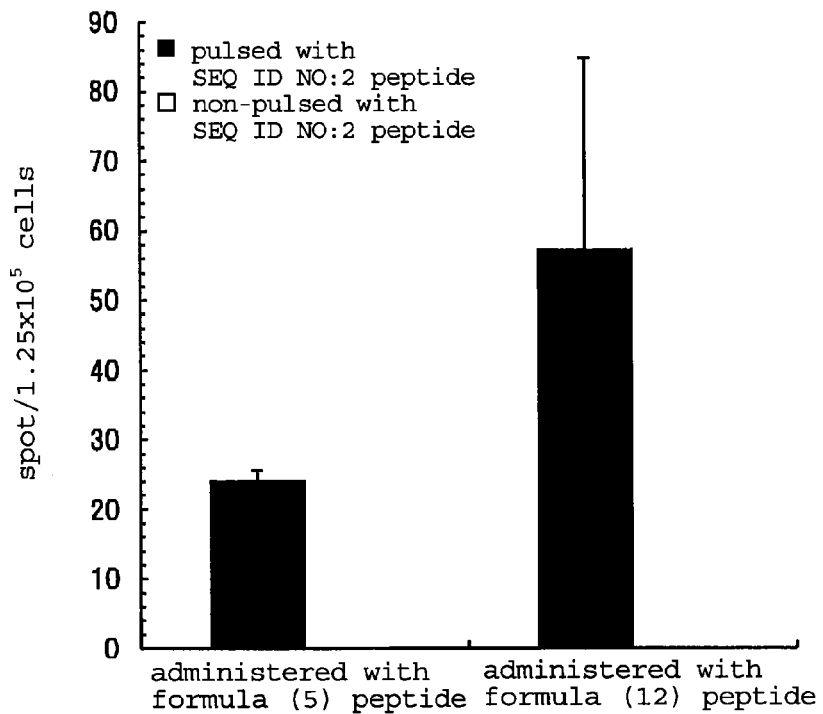
FIG. 19 is a Figure showing the test results of Experimental Example 12 as to the in vivo CTL induction ability of a compound represented by the formula (12) synthesized in Example 14 in the pulsed or non-pulsed state with peptide of SEQ ID NO: 2, by IFNγ ELISPOT assay using HLA-A0201 transgenic mouse.
Figure 20:
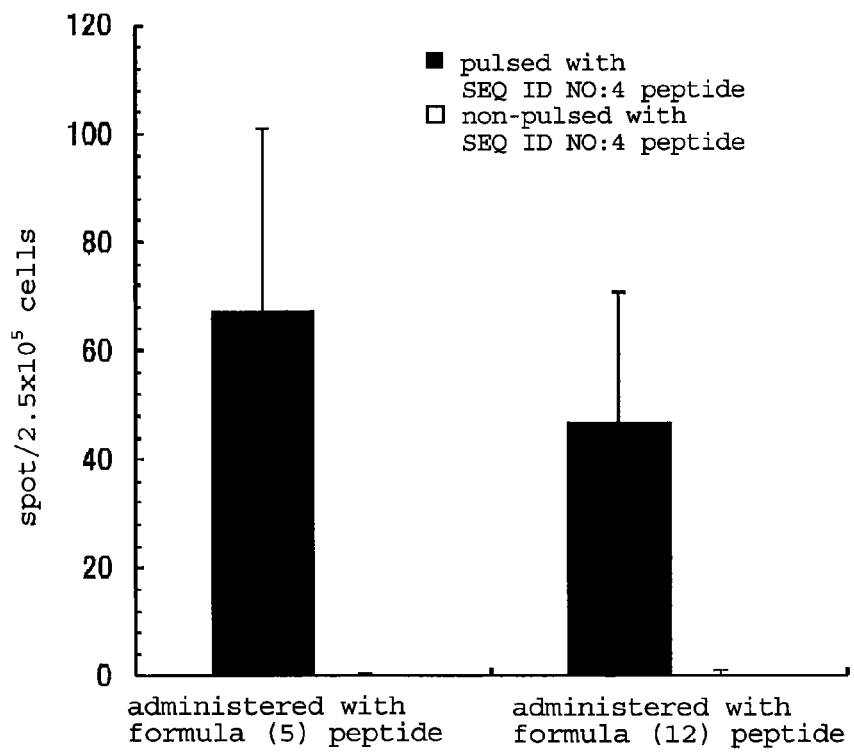
FIG. 20 is a Figure showing the test results of Experimental Example 12 as to the in vivo CTL induction ability of a compound represented by the formula (12) synthesized in Example 14 in the pulsed or non-pulsed state with peptide of SEQ ID NO: 4, by IFNγ ELISPOT assay using HLA-A2402 transgenic mouse.

The results of IFNγ ELISPOT assay using HLA-A0201 transgenic mouse are shown in FIG. 19, and the results of IFNγ ELISPOT assay using HLA-A2402 transgenic mouse are shown in FIG. 20.

In each Figure, the vertical axis shows the number of cells that reacted in the plated cells. In FIG. 19, the black bar and the white bar show the results of culture of HLA-A0201 transgenic mouse-derived splenocytes in the presence or absence of the object peptide represented by SEQ ID NO: 2, and in FIG. 20, the black bar and the white bar show the results of culture of HLA-A2402 transgenic mouse-derived splenocytes in the presence or absence of the object peptide represented by SEQ ID NO: 4. That is, the difference in the values of the black bar and the white bar show the number of the object, each peptide-specific CTL induced in the mouse in vivo by the administration of compounds represented by the formula (5) and formula (12).

In each Figure, the value of the white bar is not detected. This means that the splenocytes of respective transgenic mice did not react in the absence of the object peptide. As a result of this test, IFNγ production specific to the object peptide shown by SEQ ID NO: 2 was detected in the HLA-A0201 transgenic mouse-derived splenocytes administered compounds represented by the formula (5) and formula (12), and IFNγ production specific to the object peptide shown by SEQ ID NO: 4 was detected in the HLA-A2402 transgenic mouse-derived splenocytes administered compounds represented by the formula (5) and formula (12). In FIG. 19, the number of the IFNγ-producing cells specific to the peptide shown by SEQ ID NO: 2, which was induced by the administration of a compound represented by the formula (12), was higher than the number of the IFNγ producing cells specific to peptide, which was induced by the administration of a compound represented by the formula (5). On the other hand, in FIG. 20, the number of the IFNγ-producing cells specific to the peptide shown by SEQ ID NO: 4, which was induced by the administration of a compound represented by the formula (12), did not differ much from the number of the IFNγ producing cells specific to peptide, which was induced by the administration of a compound represented by the formula (5).

From the above, it was clarified that a compound represented by the formula (12) can induce CTL specific to the peptide shown by SEQ ID NOs: 2, 4. When a compound represented by the formula (12) was administered, many IFNγ producing cells specific to the peptide shown by SEQ ID NO: 2 were observed as compared to administration of the compound represented by the formula (5). It was assumed that the induction of the cell reactive with the helper peptide shown by SEQ ID NO: 22 produced from a compound represented by the formula (12) enhanced induction of CTL specific to the peptide shown by SEQ ID NO: 2. The absence of much difference in the number of IFNγ-producing cells specific to the peptide shown by SEQ ID NO: 4 between the administration of a compound represented by the formula 12 and the administration of a compound represented by the formula (5) was assumed to be attributable to the absence of induction of the cells reactive with the helper peptide shown by SEQ ID NO: 22, since the HLA-A2402 transgenic mouse does not express human MHC class II. Accordingly, it was strongly suggested that the compound represented by the formula (12) undergoes cleavage of disulfide bond and appropriate trimming by ERAP-1 in mouse in vivo and is in fact processed into the peptides shown by SEQ ID NOs: 2, 4 and 22.

That is, it was clarified that a compound represented by the formula (12), which is one embodiment of the compound of the present invention, is a conjugate wherein three different kinds of peptides form a composite via the disulfide bond, and is a WT1 cancer antigen peptide conjugate vaccine that in fact can induce CTLs and helper peptide reactive cells in vivo.

Experimental Example 13

Evaluation of In Vivo CTL Induction Ability Using HLA-A0201 Transgenic Mouse and HLA-A2402 Transgenic Mouse The CTL induction ability of the compound represented by the formula (14) synthesized in Example 15 was evaluated by an in vivo CTL induction test using an HLA-A0201 transgenic mouse and an HLA-A2402 transgenic mouse. RMFP-NAPYL (SEQ ID NO: 2) contained in a compound represented by the formula (14):

wherein the bond between C and C is a disulfide bond, is an HLA-A0201-restricted WT1 peptide, CYTWNQMNL (SEQ ID NO: 4) is HLA-A2402-restricted WT1 peptide, WAPVLDFAPPGASAYGSL (SEQ ID NO: 244) is MHC class II-restricted WT1 peptide (namely, helper peptide).

The HLA-A0201 transgenic mouse and HLA-A2402 transgenic mouse are as described in Experimental Examples 2 and 5.

Whether the administration of a compound represented by the formula (14) results in the induction of CTL specific to the object peptide (SEQ ID NO: 2, 4) was judged based on the measurement of IFNγ production by re-stimulation, with the peptide (SEQ ID NO: 2, 4), of the splenocyte derived from the above-mentioned mouse administered with a compound represented by the formula (14). Whether or not helper peptide (SEQ ID NO: 244) works in the living body was judged by comparison of the number of IFNγ-producing cells when the splenocytes derived from the above-mentioned mouse administered with a compound represented by the formula (14) and the splenocytes derived from the above-mentioned mouse administered with a compound represented by the formula (5) were re-stimulated with the peptide (SEQ ID NO: 2).

By a method similar to that in Experimental Example 12, a CTL induction test was performed. The compound represented by the formula (14) was dissolved in dimethyl sulfoxide (DMSO) at 80 mg/mL, diluted with water for injection at 5.6 mg/mL, and mixed with an equal amount of Montanide ISA51VG to give an emulsion. The emulsified compound was intradermally administered to 2 sites at the base of tail of a mouse at 280 μg/site.

Figure 21:
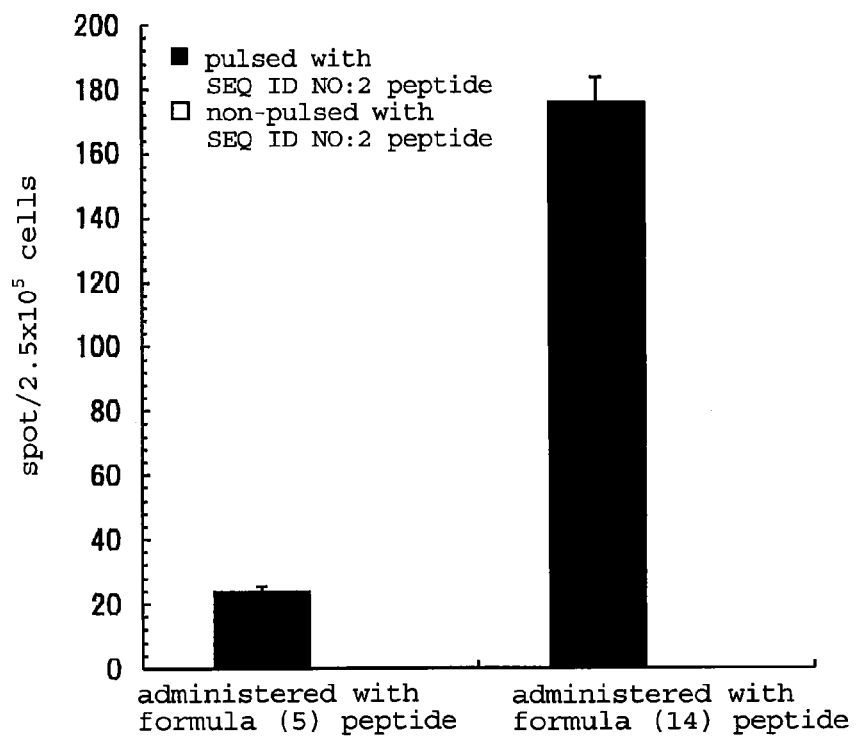
FIG. 21 is a Figure showing the test results of Experimental Example 13 as to the in vivo CTL induction ability of a compound represented by the formula (14) synthesized in Example 15 in the pulsed or non-pulsed state with peptide of SEQ ID NO: 2, by IFNγ ELISPOT assay using HLA-A0201 transgenic mouse.
Figure 22:
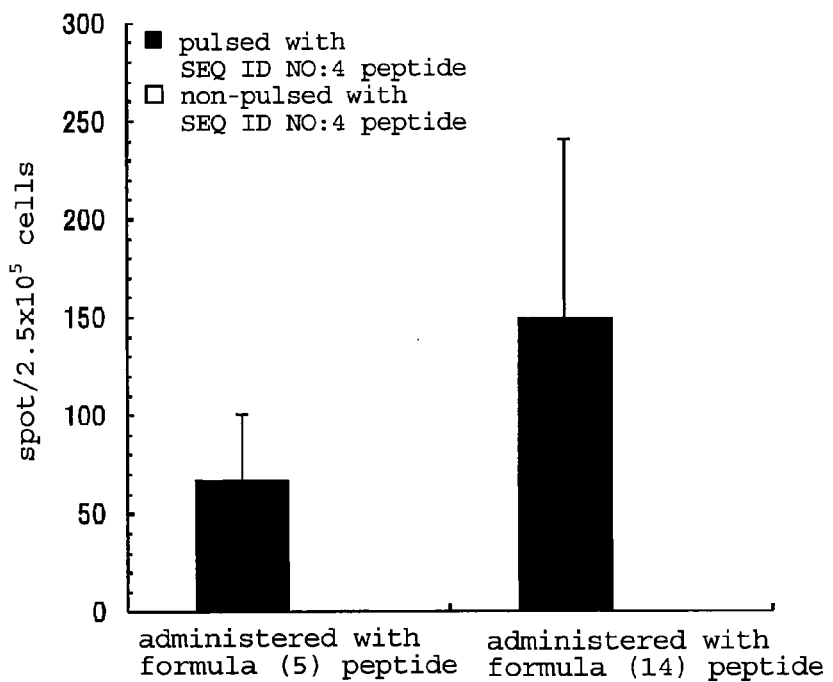
FIG. 22 is a Figure showing the test results of Experimental Example 13 as to the in vivo CTL induction ability of a compound represented by the formula (14) synthesized in Example 15 in the pulsed or non-pulsed state with peptide of SEQ ID NO: 4, by IFNγ ELISPOT assay using HLA-A2402 transgenic mouse.

The results of IFNγ ELISPOT assay using HLA-A0201 transgenic mouse are shown in FIG. 21, and the results of IFNγ ELISPOT assay using HLA-A2402 transgenic mouse are shown in FIG. 22.

In each Figure, the vertical axis shows the number of cells that reacted in the plated cells. In FIG. 21, the black bar and the white bar show the results of culture of HLA-A0201 transgenic mouse-derived splenocytes in the presence or absence of the object peptide represented by SEQ ID NO: 2, and in FIG. 22, the black bar and the white bar show the results of culture of HLA-A2402 transgenic mouse-derived splenocytes in the presence or absence of the object peptide represented by SEQ ID NO: 4. That is, the difference in the values of the black bar and the white bar show the number of the object, each peptide-specific CTL induced in the mouse in vivo by the administration of compounds represented by the formulas (5) and (14).

In each Figure, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with compounds represented by the formulas (5) and (14), and IFNγ production specific to the object peptide shown by SEQ ID NO: 4 was detected in the splenocytes derived from HLA-A2402 transgenic mouse administered with compounds represented by the formulas (5) and (14). In FIGS. 21 and 22, the number of the IFNγ producing cells specific to the peptide shown by SEQ ID NO: 2, 4, which was induced by the administration of a compound represented by the formula (14), was higher than the number of the peptide-specific IFNγ producing cells, which was induced by the administration of a compound represented by the formula (5).

From the above, it was clarified that a compound represented by the formula (14) can induce CTL specific to the peptides shown by SEQ ID NOs: 2 and 4. It was assumed that the induction of the cell reactive with the helper peptide shown by SEQ ID NO: 244 produced from a compound represented by the formula (14) enhanced induction of CTL specific to the peptide shown by SEQ ID NO: 2, and many IFNγ-producing cells specific to the peptide shown by SEQ ID NO: 2 were found when a compound represented by the formula (14) was administered as compared to the administration of a compound represented by the formula (5). On the other hand, many IFNγ-producing cells specific to the peptide shown by SEQ ID NO: 4 were found when a compound represented by the formula (14) was administered as compared to the administration of a compound represented by the formula (5). It was assumed that the peptide shown by SEQ ID NO: 244 was bound to mouse MHC class II expressed in HLA-A2402 transgenic mouse to induce the cell reactive with the helper peptide, which in turn enhanced induction of CTL specific to the peptide shown by SEQ ID NO: 4. Therefore, it was strongly suggested that the compound represented by the formula (14) undergoes cleavage of disulfide bond and appropriate trimming by ERAP-1 in mouse in vivo and is in fact processed into the peptides shown by SEQ ID NOs: 2, 4 and 244.

That is, it was clarified that a compound represented by the formula (14), which is one embodiment of the compound of the present invention, is a conjugate wherein three different kinds of peptides form a composite via the disulfide bond, and is a WT1 cancer antigen peptide conjugate vaccine that in fact can induce CTLs and helper peptide reactive cells in vivo.

Experimental Example 14

Evaluation of In Vivo CTL Induction Ability Using HLA-A0201 Transgenic Mouse

A cocktail vaccine which is a mixture of the compound represented by the formula (5) synthesized in Example 1 and the peptide shown by SEQ ID NO: 22 synthesized in Reference Example 1 was evaluated for the CTL induction ability by an in vivo CTL induction test using HLA-A0201 transgenic mouse. RMFPNAPYL (SEQ ID NO: 2) contained in the compound represented by the formula (5):

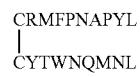

(5)

wherein the bond between C and C is a disulfide bond, is an HLA-A0201-restricted WT1 peptide, CYTWNQMNL (SEQ ID NO: 4) is HLA-A2402-restricted WT1 peptide, and CNKRYFKLSHLQMHSRK (SEQ ID NO: 22) is MHC class II-restricted WT1 peptide (namely, helper peptide).

The HLA-A0201 transgenic mouse is as described in Experimental Examples 2 and 5.

Whether the administration of a compound represented by the formula (5) results in the induction of CTL specific to the object peptide (SEQ ID NO: 2) was judged based on the measurement of IFNγ production by re-stimulation, with the peptide (SEQ ID NO: 2), of the splenocyte derived from the above-mentioned mouse administered with a compound represented by the formula (5). Whether or not the helper peptide (SEQ ID NO: 22) mixed with the formula (5) works in the living body was judged by comparison of the number of IFNγ-producing cells when the splenocytes derived from the above-mentioned mouse administered with a compound represented by the formula (5) alone and the splenocytes derived from the above-mentioned mouse administered with a cocktail vaccine of a compound represented by the formula (5) and the peptide shown by SEQ ID NO: 22 were re-stimulated with the peptide (SEQ ID NO: 2).

Specifically, a compound represented by the formula (5) was dissolved in dimethyl sulfoxide (DMSO) at 80 mg/mL, further diluted with water for injection to 3 mg/mL, and emulsified by mixing with an equal amount of Montanide ISA51VG. The emulsified compound was intradermally administered to 2 sites at the base of tail of a mouse at 150 μg/site. In addition, a compound represented by the formula (5) and the peptide shown by SEQ ID NO: 22 were dissolved in dimethyl sulfoxide (DMSO) at 80 mg/mL, diluted with water for injection and mixed such that the concentration after dilution was 3 mg/mL for the compound represented by the formula (5), and 2.7 mg/mL for the peptide shown by SEQ ID NO: 22. The diluted solution was mixed with an equal amount of Montanide ISA51VG to give an emulsion. The cocktail vaccine containing a compound represented by the formula (5) at 150 μg/site, and the peptide shown by SEQ ID NO: 22 at 137 μg/site was intradermally administered to 2 sites at the base of tail of a mouse. The DMSO concentration of each emulsion was set to the same level. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well on the blocked ELISPOT plate. Peptide (SEQ ID NO: 2) was dissolved in DMSO at 40 mg/mL, and further diluted with RPMI1640 medium containing 10% FBS to 40 μg/mL. The diluted peptide (SEQ ID NO: 2) was added to the HLA-A0201 transgenic mouse-derived splenocytes at a final concentration of 10 μg/mL. The splenocytes added with the peptide were cultured for 17 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 23:
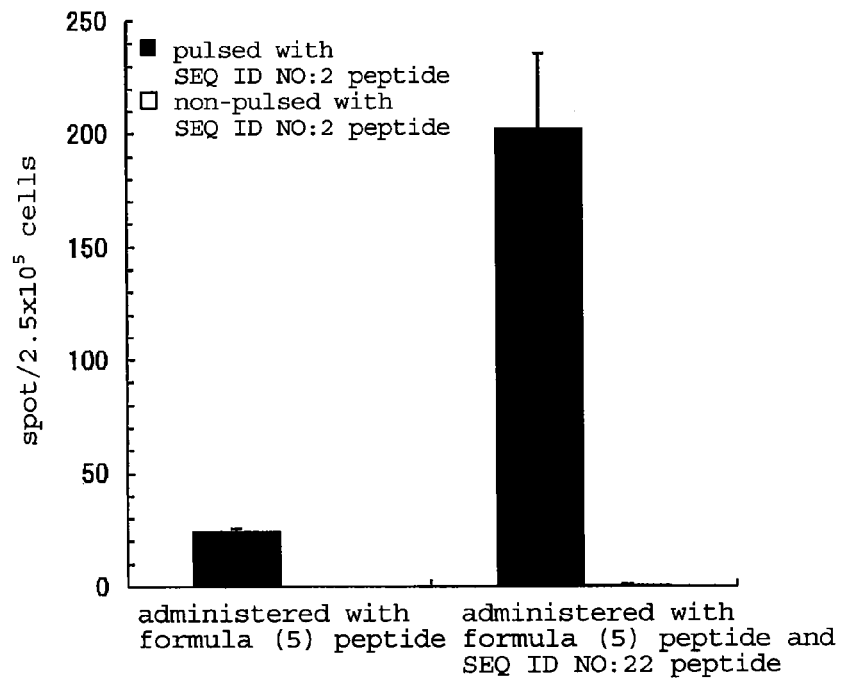
FIG. 23 is a Figure showing the test results of Experimental Example 14 as to the in vivo CTL induction ability of a cocktail vaccine of a compound represented by the formula (5) synthesized in Example 1 and the peptide shown by SEQ ID NO: 22 synthesized in Reference Example 1 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 23.

In FIG. 23, the vertical axis shows the number of cells that reacted in the plated cells. In FIG. 23, the black bar and the white bar show the results of culture of HLA-A0201 transgenic mouse-derived splenocytes in the presence or absence of the object peptide represented by SEQ ID NO: 2. That is, the difference in the values of the black bar and the white bar shows the number of the object, each peptide-specific CTL induced in the mouse in vivo by the administration of a cocktail vaccine containing a compound represented by the formula (5) and a helper peptide (SEQ ID NO: 22).

In FIG. 23, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with a compound represented by the formula (5) alone, and a cocktail vaccine containing a helper peptide (SEQ ID NO: 22). In FIG. 23, the number of the IFNγ producing cells specific to the peptide shown by SEQ ID NO: 2, which was induced by the administration of a cocktail vaccine containing a helper peptide (SEQ ID NO: 22), was higher than the number of the peptide-specific IFNγ producing cells, which was induced by the administration of a compound represented by the formula (5) alone.

From the above, it was clarified that a cocktail vaccine containing a compound represented by the formula (5) and the peptide shown by SEQ ID NO: 22 can induce CTL specific to the peptides shown by SEQ ID NO: 2. In addition, many IFNγ-producing cells specific to the peptide shown by SEQ ID NO: 2 were found when a cocktail vaccine was administered as compared to the single administration of a compound represented by the formula (5). It was assumed that the induction of the cell reactive with the helper peptide shown by SEQ ID NO: 22 contained in the cocktail vaccine enhanced induction of CTL specific to the peptide shown by SEQ ID NO: 2. Therefore, it was clarified that a cocktail vaccine containing a compound represented by the formula (5) and the helper peptide can strongly induce CTL in the body of mouse as compared to the single administration of a compound represented by the formula (5).

Experimental Example 15

Evaluation of In Vivo CTL Induction Ability Using HLA-A0201 Transgenic Mouse

The CTL induction ability of a cocktail vaccine of a compound represented by the formula (5) synthesized in Example 1 and the peptide shown by SEQ ID NO: 244 synthesized in Reference Example 13 was evaluated by an in vivo CTL induction test using an HLA-A0201 transgenic mouse. RMFPNAPYL (SEQ ID NO: 2) contained in a compound represented by the formula (5):

(5)

wherein the bond between C and C is a disulfide bond, is an HLA-A0201-restricted WT1 peptide, CYTWNQMNL (SEQ ID NO: 4) is an HLA-A2402-restricted WT1 peptide, and WAPVLDFAPPGASAYGSL (SEQ ID NO: 244) is an MHC class II-restricted WT1 peptide (namely, helper peptide).

The HLA-A0201 transgenic mouse is as described in Experimental Examples 2 and 5.

Whether the administration of a compound represented by the formula (5) results in the induction of CTL specific to the object peptide (SEQ ID NO: 2) was judged based on the measurement of IFNγ production by re-stimulation, with the peptide (SEQ ID NO: 2), of the splenocyte derived from the above-mentioned mouse administered with a compound represented by the formula (5). Whether or not the helper peptide (SEQ ID NO: 244) mixed with the formula (5) works in the living body was judged by comparison of the number of IFNγ-producing cells when the splenocytes derived from the above-mentioned mouse administered with a compound represented by the formula (5) alone and the splenocytes derived from the above-mentioned mouse administered with a cocktail vaccine of a compound represented by the formula (5) and the peptide shown by SEQ ID NO: 244 were re-stimulated with the peptide (SEQ ID NO: 2).

By a method similar to that in Experimental Example 14, CTL induction test was performed. To give a cocktail vaccine, a compound represented by the formula (5) and the peptide shown by SEQ ID NO: 244 were dissolved in dimethyl sulfoxide (DMSO) at 80 mg/mL, diluted with water for injection and mixed such that the concentration after dilution was 3 mg/mL for the compound represented by the formula (5), and 2.3 mg/mL for the peptide shown by SEQ ID NO: 244. The diluted solution was mixed with an equal amount of Montanide ISA51VG to give an emulsion. A cocktail vaccine containing the compound represented by the formula (5) at 150 µg/site, and the peptide shown by SEQ ID NO: 244 at 115 µg/site was intradermally administered to 2 sites at the base of tail of a mouse.

Figure 24:
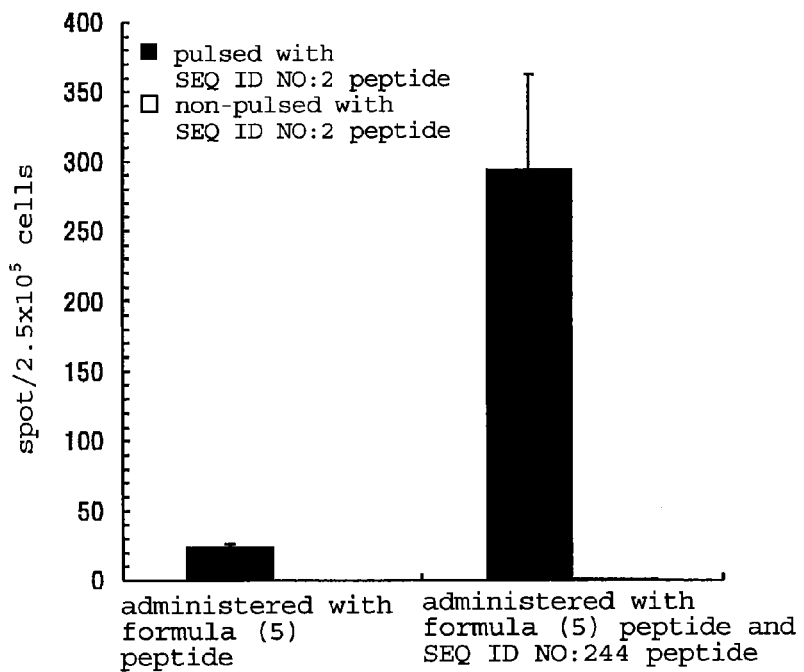
FIG. 24 is a Figure showing the test results of Experimental Example 15 as to the in vivo CTL induction ability of a cocktail vaccine of a compound represented by the formula (5) synthesized in Example 1 and the peptide shown by SEQ ID NO: 244 synthesized in Reference Example 13 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 24.

In FIG. 24, the vertical axis shows the number of cells that reacted in the plated cells. In FIG. 24, the black bar and the white bar show the results of culture of HLA-A0201 transgenic mouse-derived splenocytes in the presence or absence of the object peptide represented by SEQ ID NO: 2. That is, the difference in the values of the black bar and the white bar shows the number of the object, each peptide-specific CTL induced in the mouse in vivo by the administration of a cocktail vaccine containing a compound represented by the formula (5) and a helper peptide (SEQ ID NO: 244).

In FIG. 24, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with a compound represented by the formula (5) alone, and a cocktail vaccine containing a helper peptide (SEQ ID NO: 244). In FIG. 24, the number of the IFNγ producing cells specific to the peptide shown by SEQ ID NO: 2, which was induced by the administration of a cocktail vaccine containing a helper peptide (SEQ ID NO: 244), was higher than the number of the peptide-specific IFNγ producing cells, which was induced by the administration of a compound represented by the formula (5) alone.

From the above, it was clarified that a cocktail vaccine containing a compound represented by the formula (5) and the peptide shown by SEQ ID NO: 244 can induce CTL specific to the peptides shown by SEQ ID NO: 2. In addition, many IFNγ-producing cells specific to the peptide shown by SEQ ID NO: 2 were found when a cocktail vaccine was administered as compared to the single administration of a compound represented by the formula (5). It was assumed that the induction of the cell reactive with the helper peptide shown by SEQ ID NO: 244 contained in the cocktail vaccine enhanced induction of CTL specific to the peptide shown by SEQ ID NO: 2. Therefore, it was clarified that a cocktail vaccine containing a compound represented by the formula (5) and the helper peptide can strongly induce CTL in the body of mouse as compared to the single administration of a compound represented by the formula (5).

As one embodiment of producing a vaccine containing two WT1 antigen peptides, a cocktail vaccine containing two different peptides as a single preparation can be mentioned. When producing a cocktail vaccine, the properties of the cancer antigen peptides to be mixed poses one problem. As shown in Table 60 and Table 66, production of a cocktail of two WT1 antigen peptides means processing of two peptides having different solubility, namely, property, into one preparation. In contrast, the conjugate of the present invention is a compound wherein two WT1 antigen peptides are bonded via a disulfide bond, and shows a single solubility, namely, property. This means that the conjugate of the present invention has single property and also has the property corresponding to the two WT1 antigen peptides, as shown in Experimental Example 2. In this aspect, it was shown that the conjugate of the present invention is a compound capable of inducing a response to the two WT1 antigen peptides without the need to consider an interaction between the two WT1 antigen peptides and the like, unlike cocktail vaccines.

Experimental Example 16

Evaluation of In Vivo CTL Induction Ability Using HLA-A0201 Transgenic Mouse

The CTL induction ability of a cocktail vaccine of a compound represented by the formula (5) synthesized in Example 1 and the peptide shown by SEQ ID NO: 24 synthesized in Reference Example 2 was evaluated by an in vivo CTL induction test using an HLA-A0201 transgenic mouse. RMFPNAPYL (SEQ ID NO: 2) contained in a compound represented by the formula (5):

(5)

wherein the bond between C and C is a disulfide bond, is an HLA-A0201-restricted WT1 peptide, CYTWNQMNL (SEQ ID NO: 4) is an HLA-A2402-restricted WT1 peptide, and CNKRYFKLSHLQMHSRKTG (SEQ ID NO: 24) is an MHC class II-restricted WT1 peptide (namely, helper peptide).

The HLA-A0201 transgenic mouse is as described in Experimental Examples 2 and 5.

Whether the administration of a compound represented by the formula (5) results in the induction of CTL specific to the object peptide (SEQ ID NO: 2) was judged based on the measurement of IFNγ production by re-stimulation, with the peptide (SEQ ID NO: 2), of the splenocyte derived from the above-mentioned mouse administered with a compound represented by the formula (5). Whether or not the helper peptide (SEQ ID NO: 24) mixed with the formula (5) works in the living body was judged by comparison of the number of IFNγ-producing cells when the splenocytes derived from the above-mentioned mouse administered with a compound represented by the formula (5) alone and the splenocytes derived from the above-mentioned mouse administered with a cocktail vaccine of a compound represented by the formula (5) and the peptide shown by SEQ ID NO: 24 were re-stimulated with the peptide (SEQ ID NO: 2).

Specifically, a compound represented by the formula (5) was dissolved in dimethyl sulfoxide (DMSO) at 80 mg/mL, further diluted with water for injection to 3 mg/mL, and emulsified by mixing with an equal amount of Montanide ISA51VG. The emulsified compound was intradermally administered to 2 sites at the base of tail of a mouse at 150 μg/site. In addition, a compound represented by the formula (5) and the peptide shown by SEQ ID NO: 24 were dissolved in dimethyl sulfoxide (DMSO) at 80 mg/mL, and diluted with water for injection. They were mixed such that the concentration after dilution is 3 mg/mL for the compound represented by the formula (5), and 3.11 mg/mL for the peptide shown by SEQ ID NO: 24. The diluted solution was mixed with an equal amount of Montanide ISA51VG to give an emulsion. The cocktail vaccine containing a compound represented by the formula (5) at 150 μg/site, and the peptide shown by SEQ ID NO: 24 at 156 μg/site was intradermally administered to 2 sites at the base of tail of a mouse. The DMSO concentration of each emulsion was set to the same level. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well on the blocked ELISPOT plate. Peptide (SEQ ID NO: 2) was dissolved in DMSO at 40 mg/mL, and further diluted with RPMI1640 medium containing 10% FBS to 40 μg/mL. The diluted peptide (SEQ ID NO: 2) was added to the HLA-A0201 transgenic mouse-derived splenocytes at a final concentration of 10 μg/mL. The splenocytes added with the peptide were cultured for 19 hr at 37° C., 5% $CO_2$, whereby peptide re-stimulation in vitro was performed. After culture, the supernatant was removed, and the ELISPOT plate was allowed to develop color according to the attached protocol. The number of spots that developed color was measured by ImmunoSpot Analyzer (manufactured by C.T.L.).

Figure 25:
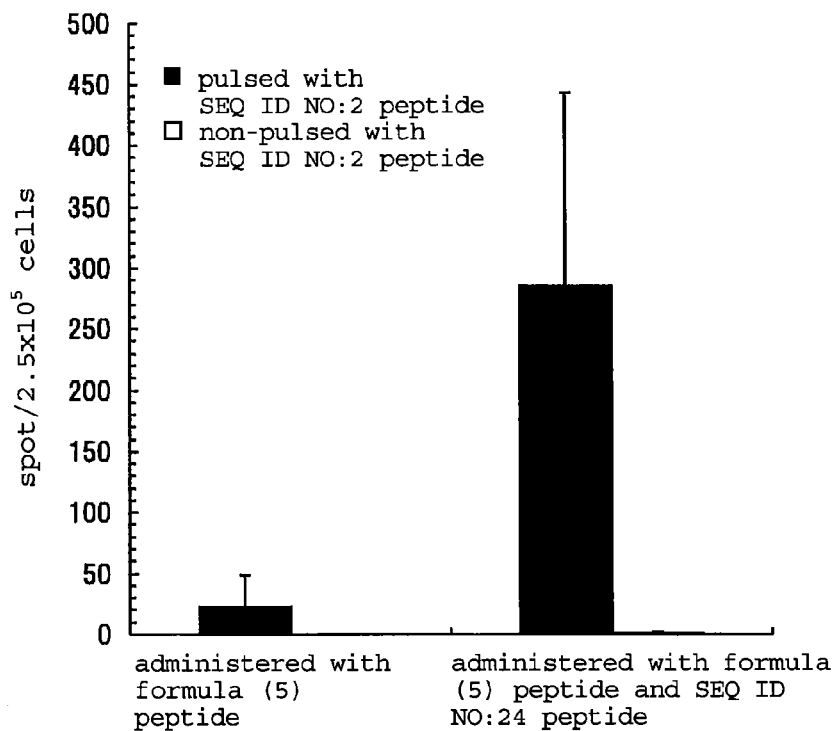
FIG. 25 is a Figure showing the test results of Experimental Example 16 as to the in vivo CTL induction ability of a cocktail vaccine of a compound represented by the formula (5) synthesized in Example 1 and the peptide shown by SEQ ID NO: 24 synthesized in Reference Example 2 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 25.

In FIG. 25, the vertical axis shows the number of cells that reacted in the plated cells. In FIG. 25, the black bar and the white bar show the results of culture of HLA-A0201 transgenic mouse-derived splenocytes in the presence or absence of the object peptide represented by SEQ ID NO: 2. That is, the difference in the values of the black bar and the white bar shows the number of the object, each peptide-specific CTL induced in the mouse in vivo by the administration of a cocktail vaccine containing a compound represented by the formula (5) and a helper peptide (SEQ ID NO: 24).

In FIG. 25, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with a compound represented by the formula (5) alone, and a cocktail vaccine containing a helper peptide (SEQ ID NO: 24). In FIG. 25, the number of the IFNγ producing cells specific to the peptide shown by SEQ ID NO: 2, which was induced by the administration of a cocktail vaccine containing a helper peptide (SEQ ID NO: 24), was higher than the number of the peptide-specific IFNγ producing cells, which was induced by the single administration of a compound represented by the formula (5) alone.

From the above, it was clarified that a cocktail vaccine containing a compound represented by the formula (5) and the peptide shown by SEQ ID NO: 24 can induce CTL specific to the peptides shown by SEQ ID NO: 2. In addition, many IFNγ-producing cells specific to the peptide shown by SEQ ID NO: 2 were found when a cocktail vaccine was administered as compared to the single administration of a compound represented by the formula (5). It was assumed that the induction of the cell reactive with the helper peptide shown by SEQ ID NO: 24 contained in the cocktail vaccine enhanced induction of CTL specific to the peptide shown by SEQ ID NO: 2. Therefore, it was clarified that a cocktail vaccine containing a compound represented by the formula (5) and the helper peptide can strongly induce CTL in the body of mouse as compared to the single administration of a compound represented by the formula (5).

Experimental Example 17

Evaluation of In Vivo CTL Induction Ability Using HLA-A0201 Transgenic Mouse

SEQ ID NO: 242 synthesized in Example 11 is the peptide shown by SEQ ID NO: 244 having an extended cysteine at the N-terminal. SEQ ID NO: 244 in the cocktail vaccine in Experimental Example 15 shows a CTL induction enhancing activity. In this test, therefore, the CTL induction ability of a cocktail vaccine of a compound represented by the formula (5) synthesized in Example 1 and the peptide shown by SEQ ID NO: 242 was evaluated by an in vivo CTL induction test using an HLA-A0201 transgenic mouse. RMFPNAPYL (SEQ ID NO: 2) contained in a compound represented by the formula (5):

(5)

wherein the bond between C and C is a disulfide bond, is an HLA-A0201-restricted WT1 peptide, CYTWNQMNL (SEQ ID NO: 4) is an HLA-A2402-restricted WT1 peptide, and WAPVLDFAPPGASAYGSL (SEQ ID NO: 244) contained in CWAPVLDFAPPGASAYGSL (SEQ ID NO: 242) is an MHC class II-restricted WT1 peptide (namely, helper peptide).

The HLA-A0201 transgenic mouse is as described in Experimental Examples 2 and 5.

Whether the administration of a compound represented by the formula (5) results in the induction of CTL specific to the object peptide (SEQ ID NO: 2) was judged based on the measurement of IFNγ production by re-stimulation, with the peptide (SEQ ID NO: 2), of the splenocyte derived from the above-mentioned mouse administered with a compound represented by the formula (5). Whether or not the helper peptide (SEQ ID NO: 242) mixed with the formula (5) works in the living body was judged by comparison of the number of IFNγ-producing cells when the splenocytes derived from the above-mentioned mouse administered with a compound represented by the formula (5) alone and the splenocytes derived from the above-mentioned mouse administered with a cocktail vaccine of a compound represented by the formula (5) and the peptide shown by SEQ ID NO: 242 were re-stimulated with the peptide (SEQ ID NO: 2).

By a method similar to that in Experimental Example 16, a CTL induction test was performed. To give a cocktail vaccine, a compound represented by the formula (5) and the peptide shown by SEQ ID NO: 242 were dissolved in dimethyl sulfoxide (DMSO) at 80 mg/mL, diluted with water for injection and mixed such that the concentration after dilution was 3 mg/mL for the compound represented by the formula (5), and 2.42 mg/mL for the peptide shown by SEQ ID NO: 242. The diluted solution was mixed with an equal amount of Montanide ISA51VG to give an emulsion. A cocktail vaccine containing the compound represented by the formula (5) at 150 μg/site, and the peptide shown by SEQ ID NO: 242 at 121 μg/site was intradermally administered to 2 sites at the base of tail of a mouse.

Figure 26:
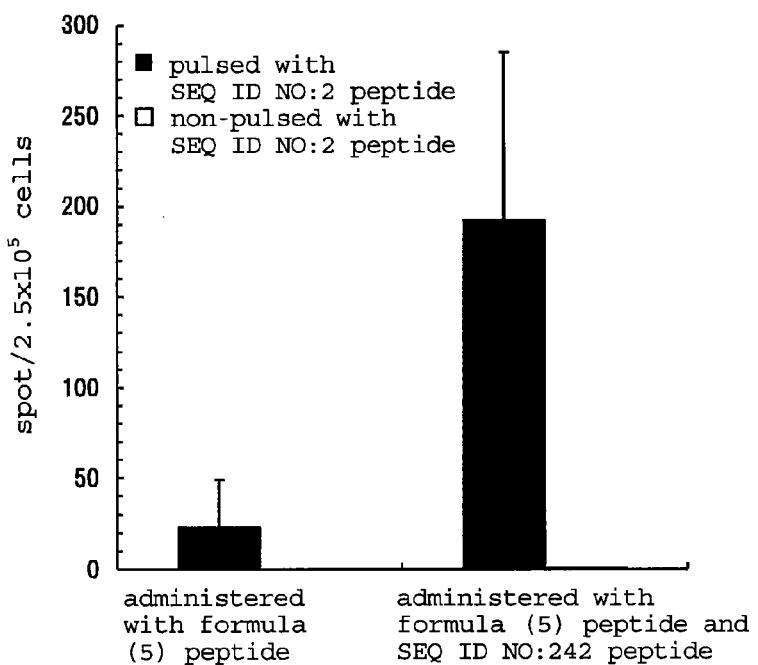
FIG. 26 is a Figure showing the test results of Experimental Example 17 as to the in vivo CTL induction ability of a cocktail vaccine of a compound represented by the formula (5) synthesized in Example 1 and the peptide shown by SEQ ID NO: 242 synthesized in Example 11 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 26.

In FIG. 26, the vertical axis shows the number of cells that reacted in the plated cells. In FIG. 26, the black bar and the white bar show the results of culture of HLA-A0201 transgenic mouse-derived splenocytes in the presence or absence of the object peptide represented by SEQ ID NO: 2. That is, the difference in the values of the black bar and the white bar shows the number of the object, each peptide-specific CTL induced in the mouse in vivo by the administration of a cocktail vaccine containing a compound represented by the formula (5) and a helper peptide (SEQ ID NO: 242).

In FIG. 26, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with a compound represented by the formula (5) alone, and a cocktail vaccine containing a helper peptide (SEQ ID NO: 242). In FIG. 26, the number of the IFNγ producing cells specific to the peptide shown by SEQ ID NO: 2, which was induced by the administration of a cocktail vaccine containing a helper peptide (SEQ ID NO: 242), was higher than the number of the peptide-specific IFNγ producing cells, which was induced by the administration of a compound represented by the formula (5) alone.

From the above, it was clarified that a cocktail vaccine containing a compound represented by the formula (5) and the peptide shown by SEQ ID NO: 242 can induce CTL specific to the peptides shown by SEQ ID NO: 2. In addition, many IFNγ-producing cells specific to the peptide shown by SEQ ID NO: 2 were found when a cocktail vaccine was administered as compared to the single administration of a compound represented by the formula (5). It was assumed that the induction of the cell reactive with the helper peptide shown by SEQ ID NO: 244 contained in the peptide shown by SEQ ID NO: 242 contained in the cocktail vaccine enhanced induction of CTL specific to the peptide shown by SEQ ID NO: 2. Therefore, it was clarified that a cocktail vaccine containing a compound represented by the formula (5) and the helper peptide can strongly induce CTL in the body of mouse as compared to the single administration of a compound represented by the formula (5).

Experimental Example 18

Evaluation of In Vivo CTL Induction Ability Using HLA-A0201 Transgenic Mouse SEQ ID NO: 243 synthesized in Example 12 is the peptide shown by SEQ ID NO: 244 having an extended cysteine at the N-terminal. SEQ ID NO: 244 in the cocktail vaccine in Experimental Example 15 shows a CTL induction enhancing activity. In this test, therefore, the CTL induction ability of a cocktail vaccine of a compound represented by the formula 1.5 (5) synthesized in Example 1 and the peptide shown by SEQ ID NO: 243 was evaluated by an in vivo CTL induction test using an HLA-A0201 transgenic mouse. RMFPNAPYL (SEQ ID NO: 2) contained in a compound represented by the formula (5):

(5)

wherein the bond between C and C is a disulfide bond, is an HLA-A0201-restricted WT1 peptide, CYTWNQMNL (SEQ ID NO: 4) is an HLA-A2402-restricted WT1 peptide, and WAPVLDFAPPGASAYGSL (SEQ ID NO: 244) contained in WAPVLDFAPPGASAYGSLC (SEQ ID NO: 243) is an MHC class II-restricted WT1 peptide (namely, helper peptide).

The HLA-A0201 transgenic mouse is as described in Experimental Examples 2 and 5.

Whether the administration of a compound represented by the formula (5) results in the induction of CTL specific to the object peptide (SEQ ID NO: 2) was judged based on the measurement of IFNγ production by re-stimulation, with the peptide (SEQ ID NO: 2), of the splenocyte derived from the above-mentioned mouse administered with a compound represented by the formula (5). Whether or not the helper peptide (SEQ ID NO: 243) mixed with the formula (5) works in the living body was judged by comparison of the number of IFNγ-producing cells when the splenocytes derived from the above-mentioned mouse administered with a compound represented by the formula (5) alone and the splenocytes derived from the above-mentioned mouse administered with a cocktail vaccine of a compound represented by the formula (5) and the peptide shown by SEQ ID NO: 243 were re-stimulated with the peptide (SEQ ID NO: 2).

By a method similar to that in Experimental Example 16, a CTL induction test was performed. To give a cocktail vaccine, a compound represented by the formula (5) and the peptide shown by SEQ ID NO: 243 were dissolved in dimethyl sulfoxide (DMSO) at 80 mg/mL, diluted with water for injection and mixed such that the concentration after dilution was 3 mg/mL for the compound represented by the formula (5), and 2.42 mg/mL for the peptide shown by SEQ ID NO: 243. The diluted solution was mixed with an equal amount of Montanide ISA51VG to give an emulsion. A cocktail vaccine containing the compound represented by the formula (5) at 150 μg/site, and the peptide shown by SEQ ID NO: 243 at 121 μg/site was intradermally administered to 2 sites at the base of tail of a mouse.

Figure 27:
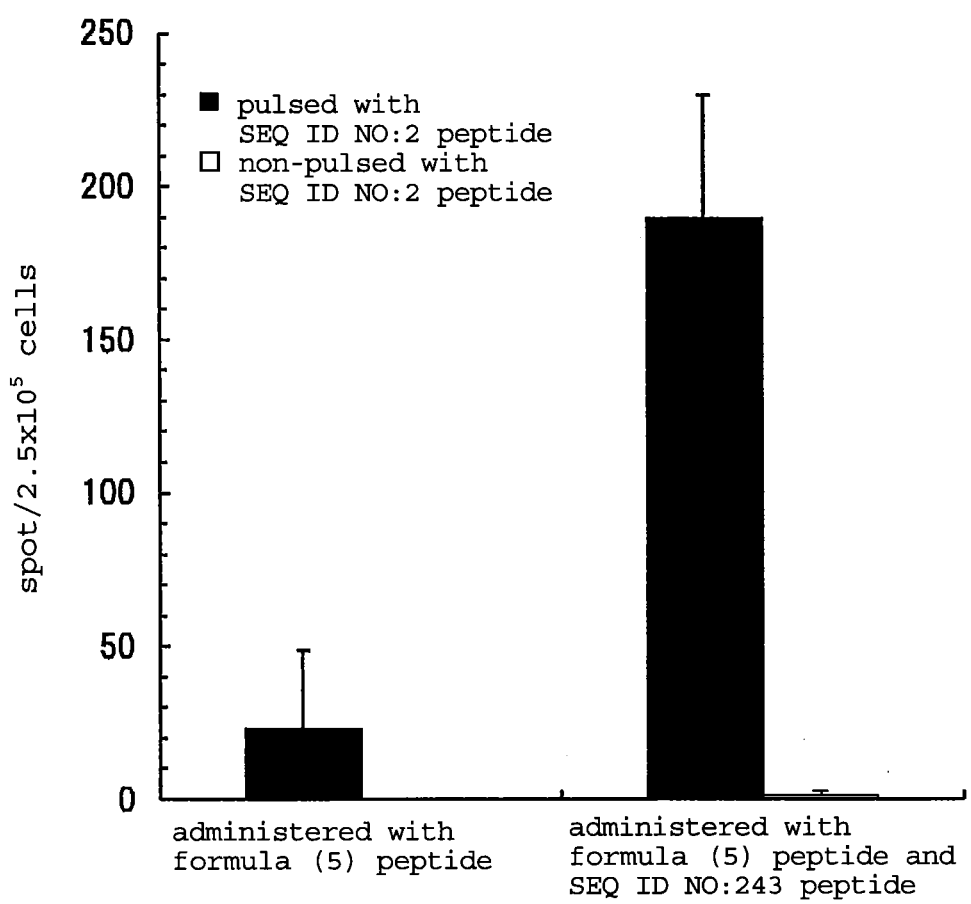
FIG. 27 is a Figure showing the test results of Experimental Example 18 as to the in vivo CTL induction ability of a cocktail vaccine of a compound represented by the formula (5) synthesized in Example 1 and the peptide shown by SEQ ID NO: 243 synthesized in Example 11 in the pulsed or non-pulsed state with peptide of SEQ ID NO: 2, by IFNγ ELISPOT assay using HLA-A0201 transgenic mouse.

The results of IFNγ ELISPOT assay using the HLA-A0201 transgenic mouse are shown in FIG. 27.

In FIG. 27, the vertical axis shows the number of cells that reacted in the plated cells. In FIG. 27, the black bar and the white bar show the results of culture of HLA-A0201 transgenic mouse-derived splenocytes in the presence or absence of the object peptide represented by SEQ ID NO: 2. That is, the difference in the values of the black bar and the white bar shows the number of the object, each peptide-specific CTL induced in the mouse in vivo by the administration of a cocktail vaccine containing a compound represented by the formula (5) and a helper peptide (SEQ ID NO: 243).

In FIG. 27, the value of the white bar is not detected. This means that the splenocytes of respective transgenic mice did not react in the absence of the object peptide. As a result of this test, IFNγ production specific to the object peptide shown by SEQ ID NO: 2 was detected in the splenocytes derived from HLA-A0201 transgenic mouse administered with a compound represented by the formula (5) alone, and a cocktail vaccine containing a helper peptide (SEQ ID NO: 243). In FIG. 27, the number of the IFNγ producing cells specific to the peptide shown by SEQ ID NO: 2, which was induced by the administration of a cocktail vaccine containing a helper peptide (SEQ ID NO: 243), was higher than the number of the peptide-specific IFNγ producing cells, which was induced by the administration of a compound represented by the formula (5) alone.

From the above, it was clarified that a cocktail vaccine containing a compound represented by the formula (5) and the peptide shown by SEQ ID NO: 243 can induce CTL specific to the peptides shown by SEQ ID NO: 2. In addition, many IFNγ-producing cells specific to the peptide shown by SEQ ID NO: 2 were found when a cocktail vaccine was administered as compared to the single administration of a compound represented by the formula (5). It was assumed that the induction of the cell reactive with the helper peptide shown by SEQ ID NO: 244 contained in the peptide shown by SEQ ID NO: 243 contained in the cocktail vaccine enhanced induction of CTL specific to the peptide shown by SEQ ID NO: 2. Therefore, it was clarified that a cocktail vaccine containing a compound represented by the formula (5) and the helper peptide can strongly induce CTL in the body of mouse as compared to the single administration of a compound represented by the formula (5).

As one embodiment of producing a vaccine containing two WT1 antigen peptides, a cocktail vaccine containing two different peptides as a single preparation can be mentioned. When producing a cocktail vaccine, the properties of the cancer antigen peptides to be mixed poses one problem. As shown in Table 60 and Table 66, production of a cocktail of two WT1 antigen peptides means processing of two peptides having different solubility, namely, property, into one preparation. In contrast, the conjugate of the present invention is a compound wherein two WT1 antigen peptides are bonded via a disulfide bond, and shows a single solubility, namely, property. This means that the conjugate of the present invention has single property and also has the property corresponding to the two WT1 antigen peptides, as shown in Experimental Example 2. In this aspect, it was shown that the conjugate of the present invention is a compound capable of inducing a response to the two WT1 antigen peptides without the need to consider an interaction between the two WT1 antigen peptides and the like, unlike cocktail vaccines.

Experimental Example 19

Evaluation of In Vivo CTL Induction Ability Using HLA-A2402 Transgenic Mouse after Filter Filtration The homodimer shown by SEQ ID NO: 4 formed via a disulfide bond and a compound represented by the formula (5) are dissolved in water for injection at 3-10 mg/mL. The pharmacological activity of each compound is evaluated using an HLA-A2402 transgenic mouse (C57BL/6CrHLA-A2402/e) with the CTL induction activity as an index. For administration to the HLA-A2402 transgenic mouse, the compound is dissolved in water for injection, sterilized by filtration using a low protein-binding filter (membrane filter of the grade aiming at sterilization treatment of injection) and mixed with incomplete Freund's adjuvant to give an emulsion.

The emulsified compound is intradermally administered to the tail root of an HLA-A2402 transgenic mouse. One week later, the mouse is euthanized with $CO_2$ gas, the spleen or inguinal lymph node is isolated, and splenocytes or or lymph node cells are prepared. IFNγ ELISPOT assay kit is used for the measurement of IFNγ production. On the previous day of cell preparation, an ELISPOT plate is treated with an anti-mouse IFNγ antibody, and blocked with RPMI1640 medium containing 10% FBS the next day. The prepared mouse-derived cells are plated on the blocked ELISPOT plate. Peptide (SEQ ID NO: 4) is dissolved in DMSO at 40 mg/mL, and further diluted with RPMI1640 medium containing 10% FBS to 40 μg/mL. The diluted peptide (SEQ ID NO: 4) is added to the HLA-A2402 transgenic mouse-derived splenocytes or lymph node cells at a final concentration of 10 μg/mL. The cells added with the peptide are cultivated for 16-20 hr at 37° C., 5% $CO_2$, whereby peptide re-stimulation in vitro is performed. After culture, the supernatant is removed, and the ELISPOT plate is allowed to develop color according to the attached protocol. The number of spots that developed color is measured by ImmunoSpot Analyzer (manufactured by C.T.L.).

INDUSTRIAL APPLICABILITY

The compound of the present invention is useful as an active ingredient of a cancer vaccine that efficiently induces CTL and is easy to produce. This application is based on a patent application Nos. 2013-072173 (filing date: Mar. 29, 2013) and 2013-158383 filed in Japan (filing date: Jul. 31, 2013), the whole contents of which are incorporated into this specification.

The invention claimed is:

1. A method of treating WT1 positive cancer, comprising: administering a therapeutically effective amount of a pharmaceutical composition to a WT1 positive cancer patient in need thereof, the pharmaceutical composition comprising a compound selected from the group consisting of

```
CRMFPNAPYL                                  (4)
|         and
CMTWNQMNL

CRMFPNAPYL,                                 (5)
|
CYTWNQMNL
``` wherein the bond between CR is a bond between the carbonyl group of C and the N-terminal amino group of R, and the bond between C and C is a disulfide bond, or a pharmaceutically acceptable salt thereof, and a pharmaceutically acceptable carrier.

2. The method of claim 1, wherein the pharmaceutical composition comprises the compound having the formula (5):

```
CRMFPNAPYL                                  (5)
|
CYTWNQMNL
``` or a pharmaceutically acceptable salt thereof.

3. The method of claim 1, wherein the pharmaceutical composition comprises the compound having the formula (5):

```
CRMFPNAPYL                                  (5)
|
CYTWNQMNL
``` and a peptide consisting of an amino acid sequence:

```
CNKRYFKLSHLQMHSRK.          (SEQ ID NO: 22)
```

4. The method of claim 1, wherein the pharmaceutical composition comprises the compound having the formula (5):

```
CRMFPNAPYL                                  (5)
|
CYTWNQMNL
``` and a peptide consisting of an amino acid sequence:

```
CNKRYFKLSHLQMHSRKHTG.       (SEQ ID NO: 24)
```

5. The method of claim 1, wherein the pharmaceutical composition comprises the compound having the formula (5):

```
CRMFPNAPYL                                  (5)
|
CYTWNQMNL
``` and a peptide consisting of an amino acid sequence:

```
CWAPVLDFAPPGASAYGSL.        (SEQ ID NO: 242)
```

6. The method of claim 1, wherein the pharmaceutical composition comprises the compound having the formula (5):

```
CRMFPNAPYL                                  (5)
|
CYTWNQMNL
``` and a peptide consisting of an amino acid sequence:

```
WAPVLDFAPPGASAYGSLC.        (SEQ ID NO: 243)
```

7. The method of claim 1, wherein the pharmaceutical composition comprises the compound having the formula (5):

```
CRMFPNAPYL                                  (5)
|
CYTWNQMNL
``` and
a peptide consisting of an amino acid sequence:

WAPVLDFAPPGASAYGSL.    (SEQ ID NO: 244)

8. The method of claim 1, wherein the WT1 positive cancer is one of leukemia, myelodysplastic syndrome, multiple myeloma, malignant lymphoma, gastric cancer, colorectal cancer, lung cancer, breast cancer, germ cell cancer, liver cancer, skin cancer, urinary bladder cancer, prostate cancer, uterine cancer, cervical cancer, ovarian cancer, and brain tumor.

9. The method of claim 1, wherein the pharmaceutical composition comprises a peptide consisting of an amino acid sequence:

CNKRYFKLSHLQMHSRK.    (SEQ ID NO: 22)

10. The method of claim 1, wherein the pharmaceutical composition comprises a peptide consisting of an amino acid sequence:

CNKRYFKLSHLQMHSRKHTG.    (SEQ ID NO: 24)

11. The method of claim 1, wherein the pharmaceutical composition comprises a peptide consisting of an amino acid sequence:

CWAPVLDFAPPGASAYGSL.    (SEQ ID NO: 242)

12. The method of claim 1, wherein the pharmaceutical composition comprises a peptide consisting of an amino acid sequence:

WAPVLDFAPPGASAYGSLC.    (SEQ ID NO: 243)

13. The method of claim 1, wherein the pharmaceutical composition comprises a peptide consisting of an amino acid sequence:

WAPVLDFAPPGASAYGSL.    (SEQ ID NO: 244)

14. The method of claim 1, wherein the pharmaceutical composition comprises the compound having the formula (4):

$$\begin{array}{c} \text{CRMFPNAPYL} \\ | \\ \text{CMTWNQMNL,} \end{array} \quad (4)$$

or a pharmaceutically acceptable salt thereof.

15. A method of inducing cytotoxic T cells against WT1 positive cancer, comprising:
administering an effective amount of a pharmaceutical composition to a subject, the pharmaceutical composition comprising
a compound selected from the group consisting of $$\begin{array}{c} \text{CRMFPNAPYL} \\ | \\ \text{CMTWNQMNL} \end{array} \quad (4)$$

and $$\begin{array}{c} \text{CRMFPNAPYL} \\ | \\ \text{CYTWNQMNL,} \end{array} \quad (5)$$

wherein the bond between CR is a bond between the carbonyl group of C and the N-terminal amino group of R, and the bond between C and C is a disulfide bond,
or a pharmaceutically acceptable salt thereof, and
a pharmaceutically acceptable carrier.

16. The method of claim 15, wherein the pharmaceutical composition comprises the compound having the formula (5):

$$\begin{array}{c} \text{CRMFPNAPYL} \\ | \\ \text{CYTWNQMNL} \end{array} \quad (5)$$

or a pharmaceutically acceptable salt thereof.

17. The method of claim 15, wherein the pharmaceutical composition comprises the compound having the formula (5):

$$\begin{array}{c} \text{CRMFPNAPYL} \\ | \\ \text{CYTWNQMNL} \end{array} \quad (5)$$

and
a peptide consisting of an amino acid sequence:

CNKRYFKLSHLQMHSRK.    (SEQ ID NO: 22)

18. The method of claim 15, wherein the pharmaceutical composition comprises the compound having the formula (5):

$$\begin{array}{c} \text{CRMFPNAPYL} \\ | \\ \text{CYTWNQMNL} \end{array} \quad (5)$$

and
a peptide consisting of an amino acid sequence:
CNKRYFKLSHLQMHSRKHTG (SEQ ID NO: 24).

19. The method of claim 10, wherein the pharmaceutical composition comprises the compound having the formula (5):

$$\begin{array}{c} \text{CRMFPNAPYL} \\ | \\ \text{CYTWNQMNL} \end{array} \quad (5)$$

and
a peptide consisting of an amino acid sequence:

CWAPVLDFAPPGASAYGSL.    (SEQ ID NO: 242)

20. The method of claim 15, wherein the pharmaceutical composition comprises the compound having the formula (5):

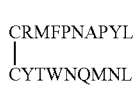
(5)

and
a peptide consisting of an amino acid sequence:

```
WAPVLDFAPPGASAYGSLC.    (SEQ ID NO: 243)
```

21. The method of claim 15, wherein the pharmaceutical composition comprises the compound having the formula (5):

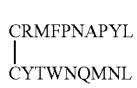
(5)

and
a peptide consisting of an amino acid sequence:

```
WAPVLDFAPPGASAYGSL.    (SEQ ID NO: 244)
```

22. The method of claim 15, wherein the WT1 positive cancer is one of leukemia, myelodysplastic syndrome, multiple myeloma, malignant lymphoma, gastric cancer, colorectal cancer, lung cancer, breast cancer, germ cell cancer, liver cancer, skin cancer, urinary bladder cancer, prostate cancer, uterine cancer, cervical cancer, ovarian cancer, and brain tumor.

23. The method of claim 15, wherein the pharmaceutical composition comprises a peptide consisting of an amino acid sequence:

```
CNKRYFKLSHLQMHSRK.    (SEQ ID NO: 22)
```

24. The method of claim 15, wherein the pharmaceutical composition comprises a peptide consisting of an amino acid sequence:

```
CNKRYFKLSHLQMHSRKHTG.    (SEQ ID NO: 24)
```

25. The method of claim 15, wherein the pharmaceutical composition comprises a peptide consisting of an amino acid sequence:

```
CWAPVLDFAPPGASAYGSL.    (SEQ ID NO: 242)
```

26. The method of claim 15, wherein the pharmaceutical composition comprises a peptide consisting of an amino acid sequence:

```
WAPVLDFAPPGASAYGSLC.    (SEQ ID NO: 243)
```

27. The method of claim 15, wherein the pharmaceutical composition comprises a peptide consisting of an amino acid sequence:

```
WAPVLDFAPPGASAYGSL.    (SEQ ID NO: 244)
```

28. The method of claim 15, wherein the pharmaceutical composition comprises the compound having the formula (4):

(4)

or a pharmaceutically acceptable salt thereof.

* * * * *

SEQUENCE LISTING

```
<160> NUMBER OF SEQ ID NOS: 244

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220
```

```
Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Arg Met Phe Pro Asn Ala Pro Tyr Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Cys Met Thr Trp Asn Gln Met Asn Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4
```

```
Cys Tyr Thr Trp Asn Gln Met Asn Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Ala Leu Leu Pro Ala Val Pro Ser Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Ser Leu Gly Glu Gln Gln Tyr Ser Val
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Arg Val Pro Gly Val Ala Pro Thr Leu
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 8

Lys Arg Tyr Phe Lys Leu Ser His Leu Gln Met His Ser Arg Lys His
1               5                   10                  15

<210> SEQ ID NO 9
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 9

Cys His Thr Pro Thr Asp Ser Cys Thr Gly Ser Gln Ala Leu Leu Leu
1               5                   10                  15

Arg Thr Pro Tyr Ser Ser Asp Asn Leu Tyr Gln Met Thr Ser Gln Leu
            20                  25                  30

<210> SEQ ID NO 10
<211> LENGTH: 22
<212> TYPE: PRT
<213> ORGANISM: Artificial Sequence
<220> FEATURE:
<223> OTHER INFORMATION: Synthetic Peptide
```

<400> SEQUENCE: 10

Pro Gly Cys Asn Lys Arg Tyr Phe Lys Leu Ser His Leu Gln Met His
1               5                   10                  15

Ser Arg Lys His Thr Gly
            20

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 11

Ser Gly Gln Ala Arg Met Phe Pro Asn Ala Pro Tyr Leu Pro Ser Cys
1               5                   10                  15

Leu Glu Ser

<210> SEQ ID NO 12
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 12

Ser Gly Gln Ala Tyr Met Phe Pro Asn Ala Pro Tyr Leu Pro Ser Cys
1               5                   10                  15

Leu Glu Ser

<210> SEQ ID NO 13
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 13

Cys Arg Met Phe Pro Asn Ala Pro Tyr Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Cys Cys Met Thr Trp Asn Gln Met Asn Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 15

Cys Cys Tyr Thr Trp Asn Gln Met Asn Leu
1               5                   10

```
<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 16

Cys Ala Leu Leu Pro Ala Val Pro Ser Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 17

Cys Ser Leu Gly Glu Gln Gln Tyr Ser Val
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18

Cys Arg Val Pro Gly Val Ala Pro Thr Leu
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 19

Ser Gly Gln Ala Arg Met Phe Pro Asn Ala Pro Tyr Leu Pro Ser Cys
1               5                   10                  15

<210> SEQ ID NO 20
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 20

Pro Gly Cys Asn Lys Arg Tyr Phe Lys Leu Ser His Leu Gln Met His
1               5                   10                  15

Ser Arg Lys

<210> SEQ ID NO 21
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 21

Pro Gly Cys Asn Lys Arg Tyr Phe Lys Leu Ser His Leu Gln Met His
1               5                   10                  15
```

Ser Arg Lys His
            20

<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 22

Cys Asn Lys Arg Tyr Phe Lys Leu Ser His Leu Gln Met His Ser Arg
1               5                   10                  15

Lys

<210> SEQ ID NO 23
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 23

Cys Asn Lys Arg Tyr Phe Lys Leu Ser His Leu Gln Met His Ser Arg
1               5                   10                  15

Lys His

<210> SEQ ID NO 24
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 24

Cys Asn Lys Arg Tyr Phe Lys Leu Ser His Leu Gln Met His Ser Arg
1               5                   10                  15

Lys His Thr Gly
            20

<210> SEQ ID NO 25
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 25

Ser Gly Gln Ala Tyr Met Phe Pro Asn Ala Pro Tyr Leu Pro Ser Cys
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26

Gly Ser Asp Val Arg Asp Leu Asn Ala
1               5

<210> SEQ ID NO 27
<211> LENGTH: 9
<212> TYPE: PRT

```
<213> ORGANISM: Artificial Sequence
<220> FEATURE:
<223> OTHER INFORMATION: Synthetic Peptide

<400> SEQUENCE: 27

Ser Asp Val Arg Asp Leu Asn Ala Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 28

Asp Val Arg Asp Leu Asn Ala Leu Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Arg Asp Leu Asn Ala Leu Leu Pro Ala
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Asp Leu Asn Ala Leu Leu Pro Ala Val
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 31

Ser Leu Gly Gly Gly Gly Gly Cys Ala
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Leu Gly Gly Gly Gly Gly Cys Ala Leu
1               5

<210> SEQ ID NO 33
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 33

Gly Gly Gly Gly Cys Ala Leu Pro Val
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 34

Gly Cys Ala Leu Pro Val Ser Gly Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 35

Cys Ala Leu Pro Val Ser Gly Ala Ala
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 36

Leu Pro Val Ser Gly Ala Ala Gln Trp
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 37

Ser Gly Ala Ala Gln Trp Ala Pro Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 38

Gly Ala Ala Gln Trp Ala Pro Val Leu
1               5

<210> SEQ ID NO 39
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 39

Ala Gln Trp Ala Pro Val Leu Asp Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 40

Gln Trp Ala Pro Val Leu Asp Phe Ala
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 41

Val Leu Asp Phe Ala Pro Pro Gly Ala
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 42

Leu Asp Phe Ala Pro Pro Gly Ala Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 43

Asp Phe Ala Pro Pro Gly Ala Ser Ala
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Phe Ala Pro Pro Gly Ala Ser Ala Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 45

Ala Tyr Gly Ser Leu Gly Gly Pro Ala
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 46

Pro Pro Pro Pro Pro His Ser Phe
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 47

Pro Pro Pro Pro Pro His Ser Phe Ile
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 48

Pro Pro Pro Pro His Ser Phe Ile Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 49

Ser Phe Ile Lys Gln Glu Pro Ser Trp
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 50

Lys Gln Glu Pro Ser Trp Gly Gly Ala
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 51

Gly Ala Glu Pro His Glu Glu Gln Cys
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 52

Ala Glu Pro His Glu Glu Gln Cys Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 53

Glu Pro His Glu Glu Gln Cys Leu Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 54

Pro His Glu Glu Gln Cys Leu Ser Ala
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 55

His Glu Glu Gln Cys Leu Ser Ala Phe
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 56

Glu Glu Gln Cys Leu Ser Ala Phe Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 57
```

Glu Gln Cys Leu Ser Ala Phe Thr Val
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 58

Cys Leu Ser Ala Phe Thr Val His Phe
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 59

Phe Thr Val His Phe Ser Gly Gln Phe
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 60

Thr Val His Phe Ser Gly Gln Phe Thr
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 61

Phe Ser Gly Gln Phe Thr Gly Thr Ala
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 62

Gly Gln Phe Thr Gly Thr Ala Gly Ala
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 63

```
Gln Phe Thr Gly Thr Ala Gly Ala Cys
1               5
```

<210> SEQ ID NO 64
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 64

```
Phe Thr Gly Thr Ala Gly Ala Cys Arg
1               5
```

<210> SEQ ID NO 65
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 65

```
Thr Gly Thr Ala Gly Ala Cys Arg Tyr
1               5
```

<210> SEQ ID NO 66
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 66

```
Ala Gly Ala Cys Arg Tyr Gly Pro Phe
1               5
```

<210> SEQ ID NO 67
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 67

```
Cys Arg Tyr Gly Pro Phe Gly Pro Pro
1               5
```

<210> SEQ ID NO 68
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 68

```
Gly Pro Phe Gly Pro Pro Pro Pro Ser
1               5
```

<210> SEQ ID NO 69
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 69

```
Ser Gln Ala Ser Ser Gly Gln Ala Arg
```

```
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 70

Gln Ala Ser Ser Gly Gln Ala Arg Met
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 71

Ala Ser Ser Gly Gln Ala Arg Met Phe
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 72

Gly Gln Ala Arg Met Phe Pro Asn Ala
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 73

Ala Arg Met Phe Pro Asn Ala Pro Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 74

Phe Pro Asn Ala Pro Tyr Leu Pro Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 75

Asn Ala Pro Tyr Leu Pro Ser Cys Leu
1               5
```

```
<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 76

Ser Cys Leu Glu Ser Gln Pro Ala Ile
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 77

Cys Leu Glu Ser Gln Pro Ala Ile Arg
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 78

Leu Glu Ser Gln Pro Ala Ile Arg Asn
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 79

Glu Ser Gln Pro Ala Ile Arg Asn Gln
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 80

Gln Pro Ala Ile Arg Asn Gln Gly Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 81

Ala Ile Arg Asn Gln Gly Tyr Ser Thr
1               5
```

<210> SEQ ID NO 82
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 82

Ile Arg Asn Gln Gly Tyr Ser Thr Val
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 83

Asn Gln Gly Tyr Ser Thr Val Thr Phe
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 84

Val Thr Phe Asp Gly Thr Pro Ser Tyr
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 85

Gly His Thr Pro Ser His His Ala Ala
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 86

Thr Pro Ser His His Ala Ala Gln Phe
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 87

Ser His His Ala Ala Gln Phe Pro Asn
1               5

```
<210> SEQ ID NO 88
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 88

Ala Ala Gln Phe Pro Asn His Ser Phe
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 89

Ala Gln Phe Pro Asn His Ser Phe Lys
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 90

His Ser Phe Lys His Glu Asp Pro Met
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 91

Lys His Glu Asp Pro Met Gly Gln Gln
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 92

Glu Asp Pro Met Gly Gln Gln Gly Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 93

Asp Pro Met Gly Gln Gln Gly Ser Leu
1               5

<210> SEQ ID NO 94
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 94

Gln Gly Ser Leu Gly Glu Gln Gln Tyr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 95

Gln Gln Tyr Ser Val Pro Pro Pro Val
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 96

Gln Tyr Ser Val Pro Pro Pro Val Tyr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 97

Ser Val Pro Pro Pro Val Tyr Gly Cys
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 98

Cys His Thr Pro Thr Asp Ser Cys Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 99

Thr Pro Thr Asp Ser Cys Thr Gly Ser
1               5

<210> SEQ ID NO 100
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 100

Thr Asp Ser Cys Thr Gly Ser Gln Ala
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 101

Asp Ser Cys Thr Gly Ser Gln Ala Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 102

Ser Cys Thr Gly Ser Gln Ala Leu Leu
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 103

Cys Thr Gly Ser Gln Ala Leu Leu Leu
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 104

Thr Gly Ser Gln Ala Leu Leu Leu Arg
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 105

Gly Ser Gln Ala Leu Leu Leu Arg Thr
1               5

<210> SEQ ID NO 106
<211> LENGTH: 9
<212> TYPE: PRT
```

```
<213> ORGANISM: Artificial Sequence
<220> FEATURE:
<223> OTHER INFORMATION: Synthetic Peptide

<400> SEQUENCE: 106

Gln Ala Leu Leu Leu Arg Thr Pro Tyr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 107

Leu Arg Thr Pro Tyr Ser Ser Asp Asn
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 108

Arg Thr Pro Tyr Ser Ser Asp Asn Leu
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 109

Thr Pro Tyr Ser Ser Asp Asn Leu Tyr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 110

Tyr Ser Ser Asp Asn Leu Tyr Gln Met
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 111

Ser Ser Asp Asn Leu Tyr Gln Met Thr
1               5

<210> SEQ ID NO 112
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 112

Ser Asp Asn Leu Tyr Gln Met Thr Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 113

Asn Leu Tyr Gln Met Thr Ser Gln Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 114

Tyr Gln Met Thr Ser Gln Leu Glu Cys
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 115

Gln Met Thr Ser Gln Leu Glu Cys Met
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 116

Thr Ser Gln Leu Glu Cys Met Thr Trp
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 117

Gln Leu Glu Cys Met Thr Trp Asn Gln
1               5

<210> SEQ ID NO 118
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 118

Leu Glu Cys Met Thr Trp Asn Gln Met
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 119

Asn Gln Met Asn Leu Gly Ala Thr Leu
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 120

Gln Met Asn Leu Gly Ala Thr Leu Lys
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 121

Asn Leu Gly Ala Thr Leu Lys Gly Val
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 122

Leu Gly Ala Thr Leu Lys Gly Val Ala
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 123

Gly Ala Thr Leu Lys Gly Val Ala Ala
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 124

Val Ala Ala Gly Ser Ser Ser Ser Val
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 125

Ala Ala Gly Ser Ser Ser Ser Val Lys
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 126

Ala Gly Ser Ser Ser Ser Val Lys Trp
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 127

Trp Thr Glu Gly Gln Ser Asn His Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 128

Thr Glu Gly Gln Ser Asn His Ser Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 129

Gly Gln Ser Asn His Ser Thr Gly Tyr
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 130

Thr Gly Tyr Glu Ser Asp Asn His Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 131

Gly Tyr Glu Ser Asp Asn His Thr Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 132

Glu Ser Asp Asn His Thr Thr Pro Ile
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 133

Ser Asp Asn His Thr Thr Pro Ile Leu
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 134

His Thr Thr Pro Ile Leu Cys Gly Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 135

Thr Pro Ile Leu Cys Gly Ala Gln Tyr
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 136
```

```
Pro Ile Leu Cys Gly Ala Gln Tyr Arg
1               5
```

<210> SEQ ID NO 137
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 137

```
Ile Leu Cys Gly Ala Gln Tyr Arg Ile
1               5
```

<210> SEQ ID NO 138
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 138

```
Gln Tyr Arg Ile His Thr His Gly Val
1               5
```

<210> SEQ ID NO 139
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 139

```
Tyr Arg Ile His Thr His Gly Val Phe
1               5
```

<210> SEQ ID NO 140
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 140

```
Arg Ile His Thr His Gly Val Phe Arg
1               5
```

<210> SEQ ID NO 141
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 141

```
His Thr His Gly Val Phe Arg Gly Ile
1               5
```

<210> SEQ ID NO 142
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 142

```
Gly Val Phe Arg Gly Ile Gln Asp Val
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 143

Val Phe Arg Gly Ile Gln Asp Val Arg
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 144

Phe Arg Gly Ile Gln Asp Val Arg Arg
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 145

Arg Gly Ile Gln Asp Val Arg Arg Val
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 146

Gln Asp Val Arg Arg Val Pro Gly Val
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 147

Asp Val Arg Arg Val Pro Gly Val Ala
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 148

Arg Arg Val Pro Gly Val Ala Pro Thr
```

```
<210> SEQ ID NO 149
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 149

Val Pro Gly Val Ala Pro Thr Leu Val
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 150

Val Ala Pro Thr Leu Val Arg Ser Ala
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 151

Thr Leu Val Arg Ser Ala Ser Glu Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 152

Arg Ser Ala Ser Glu Thr Ser Glu Lys
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 153

Ser Ala Ser Glu Thr Ser Glu Lys Arg
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 154

Ser Glu Thr Ser Glu Lys Arg Pro Phe
1               5
```

```
<210> SEQ ID NO 155
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 155

Glu Thr Ser Glu Lys Arg Pro Phe Met
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 156

Thr Ser Glu Lys Arg Pro Phe Met Cys
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 157

Ser Glu Lys Arg Pro Phe Met Cys Ala
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 158

Glu Lys Arg Pro Phe Met Cys Ala Tyr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 159

Met Cys Ala Tyr Pro Gly Cys Asn Lys
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 160

Cys Ala Tyr Pro Gly Cys Asn Lys Arg
1               5
```

<210> SEQ ID NO 161
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 161

Ala Tyr Pro Gly Cys Asn Lys Arg Tyr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 162

Tyr Pro Gly Cys Asn Lys Arg Tyr Phe
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 163

Gly Cys Asn Lys Arg Tyr Phe Lys Leu
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 164

Lys Arg Tyr Phe Lys Leu Ser His Leu
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 165

Tyr Phe Lys Leu Ser His Leu Gln Met
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 166

Leu Ser His Leu Gln Met His Ser Arg
1               5

```
<210> SEQ ID NO 167
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 167

Leu Gln Met His Ser Arg Lys His Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 168

His Ser Arg Lys His Thr Gly Glu Lys
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 169

Arg Lys His Thr Gly Glu Lys Pro Tyr
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 170

His Thr Gly Glu Lys Pro Tyr Gln Cys
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 171

Gly Glu Lys Pro Tyr Gln Cys Asp Phe
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 172

Lys Pro Tyr Gln Cys Asp Phe Lys Asp
1               5

<210> SEQ ID NO 173
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 173

Gln Cys Asp Phe Lys Asp Cys Glu Arg
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 174

Asp Phe Lys Asp Cys Glu Arg Arg Phe
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 175

Lys Asp Cys Glu Arg Arg Phe Ser Arg
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 176

Arg Arg Phe Ser Arg Ser Asp Gln Leu
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 177

Arg Phe Ser Arg Ser Asp Gln Leu Lys
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 178

Phe Ser Arg Ser Asp Gln Leu Lys Arg
1               5

<210> SEQ ID NO 179
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 179

Arg Ser Asp Gln Leu Lys Arg His Gln
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 180

Asp Gln Leu Lys Arg His Gln Arg Arg
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 181

Lys Arg His Gln Arg Arg His Thr Gly
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 182

Arg His Gln Arg Arg His Thr Gly Val
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 183

His Gln Arg Arg His Thr Gly Val Lys
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 184

Arg Arg His Thr Gly Val Lys Pro Phe
1               5

<210> SEQ ID NO 185
<211> LENGTH: 9
<212> TYPE: PRT
```

```
<213> ORGANISM: Artificial Sequence
<220> FEATURE:
<223> OTHER INFORMATION: Synthetic Peptide

<400> SEQUENCE: 185

Gly Val Lys Pro Phe Gln Cys Lys Thr
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 186

Phe Gln Cys Lys Thr Cys Gln Arg Lys
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 187

Gln Cys Lys Thr Cys Gln Arg Lys Phe
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 188

Lys Thr Cys Gln Arg Lys Phe Ser Arg
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 189

Thr Cys Gln Arg Lys Phe Ser Arg Ser
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 190

Gln Arg Lys Phe Ser Arg Ser Asp His
1               5

<210> SEQ ID NO 191
<211> LENGTH: 9
<212> TYPE: PRT
<213> ORGANISM: Artificial Sequence
```

<220> FEATURE:
<223> OTHER INFORMATION: Synthetic Peptide

<400> SEQUENCE: 191

Arg Lys Phe Ser Arg Ser Asp His Leu
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 192

Lys Phe Ser Arg Ser Asp His Leu Lys
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 193

Arg Ser Asp His Leu Lys Thr His Thr
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 194

Asp His Leu Lys Thr His Thr Arg Thr
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 195

His Thr Arg Thr His Thr Gly Lys Thr
1               5

<210> SEQ ID NO 196
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 196

Thr Gly Lys Thr Ser Glu Lys Pro Phe
1               5

<210> SEQ ID NO 197
<211> LENGTH: 9
<212> TYPE: PRT
<213> ORGANISM: Artificial Sequence
<220> FEATURE:

<223> OTHER INFORMATION: Synthetic Peptide

<400> SEQUENCE: 197

Lys Thr Ser Glu Lys Pro Phe Ser Cys
1               5

<210> SEQ ID NO 198
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 198

Thr Ser Glu Lys Pro Phe Ser Cys Arg
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 199

Ser Glu Lys Pro Phe Ser Cys Arg Trp
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 200

Lys Pro Phe Ser Cys Arg Trp Pro Ser
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 201

Ser Cys Arg Trp Pro Ser Cys Gln Lys
1               5

<210> SEQ ID NO 202
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 202

Cys Arg Trp Pro Ser Cys Gln Lys Lys
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 203

Arg Trp Pro Ser Cys Gln Lys Lys Phe
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 204

Trp Pro Ser Cys Gln Lys Lys Phe Ala
1               5

<210> SEQ ID NO 205
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 205

Pro Ser Cys Gln Lys Lys Phe Ala Arg
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 206

Ser Cys Gln Lys Lys Phe Ala Arg Ser
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 207

Lys Lys Phe Ala Arg Ser Asp Glu Leu
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 208

Lys Phe Ala Arg Ser Asp Glu Leu Val
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 209

Phe Ala Arg Ser Asp Glu Leu Val Arg
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 210

Ala Arg Ser Asp Glu Leu Val Arg His
1               5

<210> SEQ ID NO 211
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 211

Arg Ser Asp Glu Leu Val Arg His His
1               5

<210> SEQ ID NO 212
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 212

Ser Asp Glu Leu Val Arg His His Asn
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 213

Asp Glu Leu Val Arg His His Asn Met
1               5

<210> SEQ ID NO 214
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 214

Val Arg His His Asn Met His Gln Arg
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 215
```

```
Arg His His Asn Met His Gln Arg Asn
1               5
```

<210> SEQ ID NO 216
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 216

```
His His Asn Met His Gln Arg Asn Met
1               5
```

<210> SEQ ID NO 217
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 217

```
Asn Met His Gln Arg Asn Met Thr Lys
1               5
```

<210> SEQ ID NO 218
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 218

```
Met His Gln Arg Asn Met Thr Lys Leu
1               5
```

<210> SEQ ID NO 219
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 219

```
Cys Gln Lys Lys Phe Ala Arg Ser Asp Glu Leu Val Arg His His Asn
1               5                   10                  15
Met His Gln Arg Asn
            20
```

<210> SEQ ID NO 220
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 220

```
Gln Arg Asn Met Thr Lys Leu Gln Leu
1               5
```

<210> SEQ ID NO 221
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 221

Arg Asn Met Thr Lys Leu Gln Leu Ala
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 222

Asn Met Thr Lys Leu Gln Leu Ala Leu
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 223

Arg Tyr Phe Pro Asn Ala Pro Tyr Leu
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 224

Phe Met Phe Pro Asn Ala Pro Tyr Leu
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 225

Arg Leu Phe Pro Asn Ala Pro Tyr Leu
1               5

<210> SEQ ID NO 226
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 226

Arg Met Met Pro Asn Ala Pro Tyr Leu
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 227

Arg Met Phe Pro Asn Ala Pro Tyr Val
1               5

<210> SEQ ID NO 228
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 228

Tyr Met Phe Pro Asn Ala Pro Tyr Leu
1               5

<210> SEQ ID NO 229
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Ser or Ala

<400> SEQUENCE: 229

Xaa Met Thr Trp Asn Gln Met Asn Leu
1               5

<210> SEQ ID NO 230
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is selected from the group consisting of
      Ser, Ala, Abu, Arg, Lys, Orn, Cit, Leu, Phe and Asn

<400> SEQUENCE: 230

Xaa Tyr Thr Trp Asn Gln Met Asn Leu
1               5

<210> SEQ ID NO 231
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 231

Ala Tyr Leu Pro Ala Val Pro Ser Leu
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 232

Phe Leu Gly Glu Gln Gln Tyr Ser Val
1               5
```

<210> SEQ ID NO 233
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 233

Ser Met Gly Glu Gln Gln Tyr Ser Val
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 234

Ser Leu Met Glu Gln Gln Tyr Ser Val
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 235

Arg Tyr Pro Gly Val Ala Pro Thr Leu
1               5

<210> SEQ ID NO 236
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 236

Cys Leu Glu Ser Gln Pro Ala Ile Arg Asn
1               5                   10

<210> SEQ ID NO 237
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 237

Pro Ser Gln Ala Ser Ser Gly Gln Ala Arg Met Phe Pro Asn Ala Pro
1               5                   10                  15

Tyr Leu Pro Ser Cys Leu Glu
            20

<210> SEQ ID NO 238
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 238

Arg Met Phe Pro Asn Ala Pro Tyr Leu Cys Tyr Thr Trp Asn Gln Met

```
                   1               5                  10                  15

Asn Leu

<210> SEQ ID NO 239
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 239

Cys Tyr Thr Trp Asn Gln Met Asn Leu Arg Met Phe Pro Asn Ala Pro
1               5                  10                  15

Tyr Leu

<210> SEQ ID NO 240
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 240

Arg Met Phe Pro Asn Ala Pro Tyr Leu Gly Gly Gly Gly Gly Gly Cys
1               5                  10                  15

Tyr Thr Trp Asn Gln Met Asn Leu
            20

<210> SEQ ID NO 241
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 241

Cys Tyr Thr Trp Asn Gln Met Asn Leu Gly Gly Gly Gly Gly Gly Arg
1               5                  10                  15

Met Phe Pro Asn Ala Pro Tyr Leu
            20

<210> SEQ ID NO 242
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 242

Cys Trp Ala Pro Val Leu Asp Phe Ala Pro Pro Gly Ala Ser Ala Tyr
1               5                  10                  15

Gly Ser Leu

<210> SEQ ID NO 243
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 243

Trp Ala Pro Val Leu Asp Phe Ala Pro Pro Gly Ala Ser Ala Tyr Gly
1               5                  10                  15
```

```
Ser Leu Cys

<210> SEQ ID NO 244
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 244

Trp Ala Pro Val Leu Asp Phe Ala Pro Pro Gly Ala Ser Ala Tyr Gly
1               5                   10                  15

Ser Leu
```